(12) United States Patent
Flanagan et al.

(10) Patent No.: US 8,070,797 B2
(45) Date of Patent: Dec. 6, 2011

(54) MEDICAL DEVICE WITH A POROUS SURFACE FOR DELIVERY OF A THERAPEUTIC AGENT

(75) Inventors: Aiden Flanagan, Kilcolgan (IE); David McMorrow, Fort Lorenzo (IE); Anthony Malone, Oranmore (IE); Tim O'Connor, Claregalway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 262 days.

(21) Appl. No.: 12/072,666

(22) Filed: Feb. 27, 2008

(65) Prior Publication Data

US 2008/0243231 A1 Oct. 2, 2008

Related U.S. Application Data

(60) Provisional application No. 60/904,674, filed on Mar. 1, 2007.

(51) Int. Cl.
*A61F 2/06* (2006.01)
(52) U.S. Cl. ........ 623/1.42; 623/1.1; 623/1.15; 623/1.2; 623/1.39; 623/1.44; 623/1.46
(58) Field of Classification Search ................ 623/1.34, 623/1.38, 1.42–1.43, 1.46
See application file for complete search history.

(56) References Cited

U.S. PATENT DOCUMENTS

| | | |
|---|---|---|
| 3,751,283 A | 8/1973 | Dawson |
| 3,758,396 A | 9/1973 | Vieth et al. |
| 3,910,819 A | 10/1975 | Rembaum et al. |
| 3,948,254 A | 4/1976 | Zaffaroni |
| 3,952,334 A | 4/1976 | Bokros et al. |
| 3,970,445 A | 7/1976 | Gale et al. |
| 3,993,072 A | 11/1976 | Zaffaroni |
| 4,044,404 A | 8/1977 | Martin et al. |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |

(Continued)

FOREIGN PATENT DOCUMENTS

AT 232704 3/2003

(Continued)

OTHER PUBLICATIONS

Serruys et al., "The Effect of Variable Dose and Release Kinetics on Neointimal Hyperplasia Using a Novel Paclitaxel-Eluting Stent Platform," Journal of the American College of Cardiology, vol. 46, No. 2, pp. 253-260, Jul. 19, 2005.

(Continued)

*Primary Examiner* — David Isabella
*Assistant Examiner* — Jacqueline Woznicki
(74) *Attorney, Agent, or Firm* — Fish & Richardson P.C.

(57) ABSTRACT

The present invention is generally directed to implantable medical devices for delivering therapeutic agents to the body tissue of a patient and methods for making such medical devices. In particular, the present invention is directed to implantable medical devices, such as intravascular stents, having a surface that includes a plurality of cavities and a plurality of pores and a composition disposed in the pores and/or cavities, as well as, implantable medical devices, such as intravascular stents, having a surface that has a coating composition disposed on the surface, wherein the coating composition includes a plurality of cavities and a plurality of pores and another coating composition disposed in the pores and/or cavities.

50 Claims, 8 Drawing Sheets

U.S. PATENT DOCUMENTS

| | | |
|---|---|---|
| 4,321,311 A | 3/1982 | Strangman |
| 4,330,891 A | 5/1982 | Branemark et al. |
| 4,334,327 A | 6/1982 | Lyman et al. |
| 4,401,546 A | 8/1983 | Nakamura et al. |
| 4,407,695 A | 10/1983 | Deckman et al. |
| 4,475,972 A | 10/1984 | Wong |
| 4,565,744 A | 1/1986 | Walter et al. |
| 4,585,652 A | 4/1986 | Miller et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,733,665 A | 3/1988 | Palmaz |
| 4,738,740 A | 4/1988 | Pinchuk et al. |
| 4,743,252 A | 5/1988 | Martin et al. |
| 4,784,659 A | 11/1988 | Fleckenstein et al. |
| 4,800,882 A | 1/1989 | Gianturco |
| 4,842,505 A | 6/1989 | Annis et al. |
| 4,886,062 A | 12/1989 | Wiktor |
| 4,902,290 A | 2/1990 | Fleckenstein et al. |
| 4,954,126 A | 9/1990 | Wallsten |
| 4,976,692 A | 12/1990 | Atad |
| 4,994,071 A | 2/1991 | MacGregor |
| 5,061,275 A | 10/1991 | Wallsten et al. |
| 5,061,914 A | 10/1991 | Busch et al. |
| 5,073,365 A | 12/1991 | Katz et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,171,607 A | 12/1992 | Cumbo |
| 5,195,969 A | 3/1993 | Wang et al. |
| 5,205,921 A | 4/1993 | Shirkanzadeh |
| 5,219,611 A | 6/1993 | Giannelis et al. |
| 5,232,444 A | 8/1993 | Just et al. |
| 5,236,413 A | 8/1993 | Feiring |
| 5,250,242 A | 10/1993 | Nishio et al. |
| 5,270,086 A | 12/1993 | Hamlin |
| 5,279,292 A | 1/1994 | Baumann et al. |
| 5,290,585 A | 3/1994 | Elton |
| 5,302,414 A | 4/1994 | Alkhimov et al. |
| 5,304,121 A | 4/1994 | Sahatjian |
| 5,314,453 A | 5/1994 | Jeutter |
| 5,322,520 A | 6/1994 | Milder |
| 5,326,354 A | 7/1994 | Kwarteng |
| 5,348,553 A | 9/1994 | Whitney |
| 5,366,504 A | 11/1994 | Andersen et al. |
| 5,368,881 A | 11/1994 | Kelman et al. |
| 5,378,146 A | 1/1995 | Sterrett |
| 5,380,298 A | 1/1995 | Zabetakis et al. |
| 5,383,935 A | 1/1995 | Shirkhanzadeh |
| 5,397,307 A | 3/1995 | Goodin |
| 5,405,367 A | 4/1995 | Schulman et al. |
| 5,439,446 A | 8/1995 | Barry |
| 5,443,496 A | 8/1995 | Schwartz et al. |
| 5,447,724 A | 9/1995 | Helmus et al. |
| 5,449,373 A | 9/1995 | Pinchasik et al. |
| 5,449,382 A | 9/1995 | Dayton |
| 5,464,450 A | 11/1995 | Buscemi et al. |
| 5,464,650 A | 11/1995 | Berg et al. |
| 5,474,797 A | 12/1995 | Sioshansi et al. |
| 5,500,013 A | 3/1996 | Buscemi et al. |
| 5,527,337 A | 6/1996 | Stack et al. |
| 5,545,208 A | 8/1996 | Wolff et al. |
| 5,551,954 A | 9/1996 | Buscemi et al. |
| 5,569,463 A | 10/1996 | Helmus et al. |
| 5,578,075 A | 11/1996 | Dayton |
| 5,587,507 A | 12/1996 | Kohn et al. |
| 5,591,224 A | 1/1997 | Schwartz et al. |
| 5,603,556 A | 2/1997 | Klink |
| 5,605,696 A | 2/1997 | Eury et al. |
| 5,607,463 A | 3/1997 | Schwartz et al. |
| 5,607,467 A | 3/1997 | Froix |
| 5,609,629 A | 3/1997 | Fearnot et al. |
| 5,614,549 A | 3/1997 | Greenwald et al. |
| 5,624,411 A | 4/1997 | Tuch |
| 5,649,951 A | 7/1997 | Davidson |
| 5,649,977 A | 7/1997 | Campbell |
| 5,672,242 A | 9/1997 | Jen |
| 5,674,192 A | 10/1997 | Sahatjian et al. |
| 5,674,242 A | 10/1997 | Phan et al. |
| 5,679,440 A | 10/1997 | Kubota |
| 5,681,196 A | 10/1997 | Jin et al. |
| 5,690,670 A | 11/1997 | Davidson |
| 5,693,085 A | 12/1997 | Buirge et al. |
| 5,693,928 A | 12/1997 | Egitto et al. |
| 5,711,866 A | 1/1998 | Lashmore et al. |
| 5,733,924 A | 3/1998 | Kanda et al. |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,758,562 A | 6/1998 | Thompson |
| 5,761,775 A | 6/1998 | Legome et al. |
| 5,769,883 A | 6/1998 | Buscemi et al. |
| 5,772,864 A | 6/1998 | Moller et al. |
| 5,776,184 A | 7/1998 | Tuch |
| 5,780,807 A | 7/1998 | Saunders |
| 5,788,687 A | 8/1998 | Batich et al. |
| 5,788,979 A | 8/1998 | Alt et al. |
| 5,795,626 A | 8/1998 | Gabel et al. |
| 5,797,898 A | 8/1998 | Santini, Jr. et al. |
| 5,807,407 A | 9/1998 | England et al. |
| 5,817,046 A | 10/1998 | Glickman |
| 5,824,045 A | 10/1998 | Alt |
| 5,824,048 A | 10/1998 | Tuch |
| 5,824,049 A | 10/1998 | Ragheb et al. |
| 5,824,077 A | 10/1998 | Mayer |
| 5,830,480 A | 11/1998 | Ducheyne et al. |
| 5,837,313 A | 11/1998 | Ding et al. |
| 5,843,089 A | 12/1998 | Sahatjian et al. |
| 5,843,172 A | 12/1998 | Yan |
| 5,852,088 A | 12/1998 | Dismukes et al. |
| 5,858,556 A | 1/1999 | Eckert et al. |
| 5,873,904 A | 2/1999 | Ragheb et al. |
| 5,874,134 A | 2/1999 | Rao et al. |
| 5,879,697 A | 3/1999 | Ding et al. |
| 5,882,335 A | 3/1999 | Leone et al. |
| 5,888,591 A | 3/1999 | Gleason et al. |
| 5,891,108 A | 4/1999 | Leone et al. |
| 5,891,192 A | 4/1999 | Murayama et al. |
| 5,902,266 A | 5/1999 | Leone et al. |
| 5,922,021 A | 7/1999 | Jang |
| 5,928,247 A | 7/1999 | Barry et al. |
| 5,951,881 A | 9/1999 | Rogers et al. |
| 5,954,706 A | 9/1999 | Sahatjian |
| 5,962,136 A | 10/1999 | Dewez et al. |
| 5,968,091 A | 10/1999 | Pinchuk et al. |
| 5,968,092 A | 10/1999 | Buscemi et al. |
| 5,968,640 A | 10/1999 | Lubowitz et al. |
| 5,972,027 A | 10/1999 | Johnson |
| 5,977,204 A | 11/1999 | Boyan et al. |
| 5,980,564 A | 11/1999 | Stinson |
| 5,980,566 A | 11/1999 | Alt et al. |
| 6,013,591 A | 1/2000 | Ying et al. |
| 6,017,577 A | 1/2000 | Hostettler et al. |
| 6,022,812 A | 2/2000 | Smith et al. |
| 6,025,036 A | 2/2000 | McGill et al. |
| 6,034,295 A | 3/2000 | Rehberg et al. |
| 6,045,877 A | 4/2000 | Gleason et al. |
| 6,063,101 A | 5/2000 | Jacobsen et al. |
| 6,071,305 A | 6/2000 | Brown et al. |
| 6,074,135 A | 6/2000 | Tapphorn et al. |
| 6,096,070 A | 8/2000 | Ragheb et al. |
| 6,099,561 A | 8/2000 | Alt |
| 6,099,562 A | 8/2000 | Ding et al. |
| 6,106,473 A | 8/2000 | Violante et al. |
| 6,120,536 A | 9/2000 | Ding et al. |
| 6,120,660 A | 9/2000 | Chu et al. |
| 6,122,564 A | 9/2000 | Koch et al. |
| 6,139,573 A | 10/2000 | Sogard et al. |
| 6,139,913 A | 10/2000 | Van Steenkiste et al. |
| 6,153,252 A | 11/2000 | Hossainy et al. |
| 6,156,435 A | 12/2000 | Gleason et al. |
| 6,159,142 A | 12/2000 | Alt |

| Patent | Date | Inventor |
|---|---|---|
| 6,171,609 B1 | 1/2001 | Kunz |
| 6,174,329 B1 | 1/2001 | Callol et al. |
| 6,174,330 B1 | 1/2001 | Stinson |
| 6,180,184 B1 | 1/2001 | Gray et al. |
| 6,187,037 B1 | 2/2001 | Satz |
| 6,190,404 B1 | 2/2001 | Palmaz et al. |
| 6,193,761 B1 | 2/2001 | Treacy |
| 6,200,685 B1 | 3/2001 | Davidson |
| 6,203,536 B1 | 3/2001 | Berg et al. |
| 6,206,915 B1 * | 3/2001 | Fagan et al. ................ 623/1.42 |
| 6,206,916 B1 | 3/2001 | Furst |
| 6,210,715 B1 | 4/2001 | Starling et al. |
| 6,212,607 B1 | 4/2001 | Scheiner et al. |
| 6,214,042 B1 | 4/2001 | Jacobsen et al. |
| 6,217,607 B1 | 4/2001 | Alt |
| 6,231,600 B1 | 5/2001 | Zhong |
| 6,240,616 B1 * | 6/2001 | Yan ............................ 29/527.2 |
| 6,241,762 B1 | 6/2001 | Shanley |
| 6,245,104 B1 | 6/2001 | Alt |
| 6,249,952 B1 | 6/2001 | Ding |
| 6,251,136 B1 | 6/2001 | Guruwaiya et al. |
| 6,253,443 B1 | 7/2001 | Johnson |
| 6,254,632 B1 | 7/2001 | Wu et al. |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,280,411 B1 | 8/2001 | Lennox |
| 6,283,386 B1 | 9/2001 | Van Steenkiste et al. |
| 6,284,305 B1 | 9/2001 | Ding et al. |
| 6,287,331 B1 | 9/2001 | Heath |
| 6,287,332 B1 | 9/2001 | Bolz et al. |
| 6,287,628 B1 | 9/2001 | Hossainy et al. |
| 6,290,721 B1 | 9/2001 | Heath |
| 6,299,604 B1 | 10/2001 | Ragheb et al. |
| 6,306,144 B1 | 10/2001 | Sydney et al. |
| 6,315,708 B1 | 11/2001 | Salmon et al. |
| 6,315,794 B1 | 11/2001 | Richter |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,330 B1 | 12/2001 | Choy et al. |
| 6,335,029 B1 | 1/2002 | Kamath et al. |
| 6,337,076 B1 | 1/2002 | Studin |
| 6,342,507 B1 | 1/2002 | Naicker et al. |
| 6,348,960 B1 | 2/2002 | Etori et al. |
| 6,358,532 B2 | 3/2002 | Starling et al. |
| 6,358,556 B1 | 3/2002 | Ding et al. |
| 6,364,856 B1 | 4/2002 | Ding et al. |
| 6,367,412 B1 | 4/2002 | Ramaswamy et al. |
| 6,368,658 B1 | 4/2002 | Schwarz et al. |
| 6,379,383 B1 | 4/2002 | Palmaz et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,052 B2 | 5/2002 | Buirge et al. |
| 6,395,325 B1 | 5/2002 | Hedge et al. |
| 6,395,326 B1 | 5/2002 | Castro et al. |
| 6,398,806 B1 | 6/2002 | You |
| 6,413,271 B1 | 7/2002 | Hafeli et al. |
| 6,416,820 B1 | 7/2002 | Yamada et al. |
| 6,419,692 B1 | 7/2002 | Yang et al. |
| 6,436,133 B1 | 8/2002 | Furst et al. |
| 6,440,503 B1 | 8/2002 | Merdan et al. |
| 6,458,153 B1 | 10/2002 | Bailey et al. |
| 6,465,052 B1 | 10/2002 | Wu |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,418 B2 | 11/2002 | Li et al. |
| 6,488,715 B1 | 12/2002 | Pope et al. |
| 6,491,666 B1 | 12/2002 | Santini, Jr. et al. |
| 6,491,720 B1 | 12/2002 | Vallana et al. |
| 6,503,921 B2 | 1/2003 | Naicker et al. |
| 6,504,292 B1 | 1/2003 | Choi et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,514,289 B1 | 2/2003 | Pope et al. |
| 6,517,888 B1 | 2/2003 | Weber |
| 6,524,274 B1 | 2/2003 | Rosenthal et al. |
| 6,527,801 B1 | 3/2003 | Dutta |
| 6,527,938 B2 | 3/2003 | Bales et al. |
| 6,530,951 B1 | 3/2003 | Bates et al. |
| 6,537,310 B1 | 3/2003 | Palmaz et al. |
| 6,544,582 B1 | 4/2003 | Yoe |
| 6,545,097 B2 | 4/2003 | Pinchuk et al. |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,585,765 B1 | 7/2003 | Hossainy et al. |
| 6,599,558 B1 | 7/2003 | Al-Lamee et al. |
| 6,607,598 B2 | 8/2003 | Schwarz et al. |
| 6,613,083 B2 | 9/2003 | Alt |
| 6,613,432 B2 | 9/2003 | Zamora et al. |
| 6,616,765 B1 | 9/2003 | Castro et al. |
| 6,620,194 B2 | 9/2003 | Ding et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,656,162 B2 * | 12/2003 | Santini et al. ................ 604/191 |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,999 B1 | 1/2004 | Wang et al. |
| 6,676,987 B2 | 1/2004 | Zhong et al. |
| 6,676,989 B2 | 1/2004 | Kirkpatrick et al. |
| 6,689,803 B2 | 2/2004 | Hunter |
| 6,695,865 B2 | 2/2004 | Boyle et al. |
| 6,699,281 B2 | 3/2004 | Vallana et al. |
| 6,699,282 B1 | 3/2004 | Sceusa |
| 6,709,379 B1 * | 3/2004 | Brandau et al. ................ 600/3 |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,723,120 B2 | 4/2004 | Yan |
| 6,725,901 B1 | 4/2004 | Kramer et al. |
| 6,726,712 B1 | 4/2004 | Raeder-Devens et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,736,849 B2 | 5/2004 | Li et al. |
| 6,740,077 B1 | 5/2004 | Brandau et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,761,736 B1 | 7/2004 | Woo et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,780,424 B2 | 8/2004 | Claude |
| 6,780,491 B1 | 8/2004 | Cathey et al. |
| 6,783,543 B2 | 8/2004 | Jang |
| 6,790,228 B2 | 9/2004 | Hossainy et al. |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| 6,815,609 B1 | 11/2004 | Wang et al. |

| Patent No. | Date | Name |
|---|---|---|
| 6,820,676 B2 | 11/2004 | Palmaz et al. |
| 6,827,737 B2 | 12/2004 | Hill et al. |
| 6,830,598 B1 | 12/2004 | Sung |
| 6,833,004 B2 | 12/2004 | Ishii et al. |
| 6,846,323 B2 | 1/2005 | Yip et al. |
| 6,846,841 B2 | 1/2005 | Hunter et al. |
| 6,849,085 B2 | 2/2005 | Marton |
| 6,849,089 B2 | 2/2005 | Stoll |
| 6,852,122 B2 | 2/2005 | Rush |
| 6,861,088 B2 | 3/2005 | Weber et al. |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,896,697 B1 | 5/2005 | Yip et al. |
| 6,899,914 B2 | 5/2005 | Schaldach et al. |
| 6,904,658 B2 | 6/2005 | Hines |
| 6,908,622 B2 | 6/2005 | Barry et al. |
| 6,908,624 B2 | 6/2005 | Hossainy et al. |
| 6,913,617 B1 | 7/2005 | Reiss |
| 6,915,796 B2 | 7/2005 | Sung |
| 6,918,927 B2 | 7/2005 | Bates et al. |
| 6,918,929 B2 | 7/2005 | Udipi et al. |
| 6,923,829 B2 | 8/2005 | Boyle et al. |
| 6,924,004 B2 | 8/2005 | Rao et al. |
| 6,932,930 B2 | 8/2005 | DeSimone et al. |
| 6,936,066 B2 | 8/2005 | Palmaz et al. |
| 6,939,320 B2 | 9/2005 | Lennox |
| 6,951,053 B2 | 10/2005 | Padilla et al. |
| 6,953,560 B1 | 10/2005 | Castro et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,971,813 B2 | 12/2005 | Shekalim et al. |
| 6,973,718 B2 | 12/2005 | Sheppard, Jr. et al. |
| 6,979,346 B1 | 12/2005 | Hossainy et al. |
| 6,979,348 B2 | 12/2005 | Sundar |
| 6,984,404 B1 | 1/2006 | Talton et al. |
| 7,001,421 B2 | 2/2006 | Cheng et al. |
| 7,011,680 B2 | 3/2006 | Alt |
| 7,014,654 B2 | 3/2006 | Welsh et al. |
| 7,018,408 B2 | 3/2006 | Bailey et al. |
| 7,041,130 B2 | 5/2006 | Santini, Jr. et al. |
| 7,048,939 B2 | 5/2006 | Elkins et al. |
| 7,052,488 B2 | 5/2006 | Uhland |
| 7,056,338 B2 * | 6/2006 | Shanley et al. ............... 623/1.42 |
| 7,056,339 B2 | 6/2006 | Elkins et al. |
| 7,056,591 B1 | 6/2006 | Pacetti et al. |
| 7,060,051 B2 | 6/2006 | Palasis |
| 7,063,748 B2 | 6/2006 | Talton |
| 7,066,234 B2 | 6/2006 | Sawitowski |
| 7,077,859 B2 | 7/2006 | Sirhan et al. |
| 7,078,108 B2 | 7/2006 | Zhang et al. |
| 7,083,642 B2 | 8/2006 | Sirhan et al. |
| 7,087,661 B1 | 8/2006 | Alberte et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,144,840 B2 | 12/2006 | Yeung et al. |
| 7,160,592 B2 | 1/2007 | Rypacek et al. |
| 7,163,555 B2 * | 1/2007 | Dinh ............................. 623/1.42 |
| 7,163,715 B1 | 1/2007 | Kramer |
| 7,169,177 B2 | 1/2007 | Obara |
| 7,169,178 B1 | 1/2007 | Santos et al. |
| 694,436 A1 | 3/2007 | Atanasoska et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,244,272 B2 | 7/2007 | Dubson et al. |
| 7,247,166 B2 | 7/2007 | Pienknagura |
| 7,247,338 B2 | 7/2007 | Pui et al. |
| 7,261,735 B2 | 8/2007 | Llanos et al. |
| 7,261,752 B2 | 8/2007 | Sung |
| 7,273,493 B2 | 9/2007 | Ledergerber |
| 7,294,409 B2 | 11/2007 | Lye et al. |
| 7,311,727 B2 | 12/2007 | Mazumder et al. |
| 7,344,563 B2 | 3/2008 | Vallana et al. |
| 7,368,065 B2 | 5/2008 | Yang et al. |
| 7,393,589 B2 | 7/2008 | Aharonov et al. |
| 7,396,538 B2 | 7/2008 | Granada et al. |
| 7,402,173 B2 | 7/2008 | Scheuermann et al. |
| 7,416,558 B2 | 8/2008 | Yip et al. |
| 7,435,256 B2 | 10/2008 | Stenzel |
| 7,482,034 B2 | 1/2009 | Boulais |
| 7,494,950 B2 | 2/2009 | Armitage et al. |
| 7,497,876 B2 | 3/2009 | Tuke et al. |
| 7,547,445 B2 | 6/2009 | Chudzik et al. |
| 7,563,324 B1 | 7/2009 | Chen et al. |
| 7,575,593 B2 | 8/2009 | Rea et al. |
| 7,635,515 B1 | 12/2009 | Sherman |
| 7,638,156 B1 | 12/2009 | Hossainy et al. |
| 7,691,461 B1 | 4/2010 | Prabhu |
| 7,713,297 B2 | 5/2010 | Alt |
| 7,749,264 B2 | 7/2010 | Gregorich et al. |
| 7,758,636 B2 * | 7/2010 | Shanley et al. ............... 623/1.42 |
| 7,771,773 B2 | 8/2010 | Namavar |
| 7,837,726 B2 | 11/2010 | Von Oepen et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0014717 A1 | 8/2001 | Hossainy et al. |
| 2001/0014821 A1 | 8/2001 | Juman et al. |
| 2001/0027299 A1 | 10/2001 | Yang et al. |
| 2001/0029660 A1 | 10/2001 | Johnson |
| 2001/0032011 A1 | 10/2001 | Stanford |
| 2001/0032013 A1 | 10/2001 | Marton |
| 2001/0044651 A1 | 11/2001 | Steinke et al. |
| 2002/0000175 A1 | 1/2002 | Hintermaier et al. |
| 2002/0004060 A1 | 1/2002 | Heublein et al. |
| 2002/0007102 A1 | 1/2002 | Salmon et al. |
| 2002/0007209 A1 | 1/2002 | Scheerder et al. |
| 2002/0009604 A1 | 1/2002 | Zamora et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0038146 A1 | 3/2002 | Harry |
| 2002/0042039 A1 | 4/2002 | Kim et al. |
| 2002/0051730 A1 | 5/2002 | Bodnar et al. |
| 2002/0051846 A1 | 5/2002 | Kirkpatrick et al. |
| 2002/0052288 A1 | 5/2002 | Krell et al. |
| 2002/0065553 A1 | 5/2002 | Weber |
| 2002/0072734 A1 | 6/2002 | Liedtke et al. |
| 2002/0077520 A1 | 6/2002 | Segal et al. |
| 2002/0077693 A1 | 6/2002 | Barclay et al. |
| 2002/0087123 A1 | 7/2002 | Hossainy et al. |
| 2002/0091375 A1 | 7/2002 | Sahatjian et al. |
| 2002/0095871 A1 | 7/2002 | McArdle et al. |
| 2002/0098278 A1 | 7/2002 | Bates et al. |
| 2002/0099359 A1 | 7/2002 | Santini, Jr. et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0104599 A1 | 8/2002 | Tillotson et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133225 A1 | 9/2002 | Gordon |
| 2002/0138100 A1 | 9/2002 | Stoll et al. |
| 2002/0138136 A1 | 9/2002 | Chandresekaran et al. |
| 2002/0140137 A1 | 10/2002 | Sapieszko et al. |
| 2002/0142579 A1 | 10/2002 | Vincent et al. |
| 2002/0144757 A1 | 10/2002 | Craig et al. |
| 2002/0155212 A1 | 10/2002 | Hossainy |
| 2002/0165265 A1 | 11/2002 | Hunter et al. |
| 2002/0165600 A1 | 11/2002 | Banas et al. |

| | | | | | |
|---|---|---|---|---|---|
| 2002/0165607 A1 | 11/2002 | Alt | 2003/0236514 A1 | 12/2003 | Schwarz |
| 2002/0167118 A1 | 11/2002 | Billiet et al. | 2004/0000540 A1 | 1/2004 | Soboyejo et al. |
| 2002/0168466 A1 | 11/2002 | Tapphorn et al. | 2004/0002755 A1 | 1/2004 | Fischell et al. |
| 2002/0169493 A1 | 11/2002 | Widenhouse et al. | 2004/0006382 A1 | 1/2004 | Sohier |
| 2002/0178570 A1 | 12/2002 | Sogard et al. | 2004/0013873 A1 | 1/2004 | Wendorff et al. |
| 2002/0182241 A1 | 12/2002 | Borenstein et al. | 2004/0016651 A1 | 1/2004 | Windler |
| 2002/0183581 A1 | 12/2002 | Yoe et al. | 2004/0018296 A1 | 1/2004 | Castro et al. |
| 2002/0183682 A1 | 12/2002 | Darvish et al. | 2004/0019376 A1 | 1/2004 | Alt |
| 2002/0187260 A1 | 12/2002 | Sheppard, Jr. et al. | 2004/0022824 A1 | 2/2004 | Li et al. |
| 2002/0193336 A1 | 12/2002 | Elkins et al. | 2004/0026811 A1 | 2/2004 | Murphy et al. |
| 2002/0193869 A1 | 12/2002 | Dang | 2004/0028875 A1 | 2/2004 | Van Rijn et al. |
| 2002/0197178 A1 | 12/2002 | Yan | 2004/0029303 A1 | 2/2004 | Hart et al. |
| 2002/0198601 A1 | 12/2002 | Bales et al. | 2004/0029706 A1 | 2/2004 | Barrera et al. |
| 2003/0003160 A1 | 1/2003 | Pugh et al. | 2004/0030218 A1 | 2/2004 | Kocur et al. |
| 2003/0003220 A1 | 1/2003 | Zhong et al. | 2004/0030377 A1 | 2/2004 | Dubson et al. |
| 2003/0004563 A1 | 1/2003 | Jackson et al. | 2004/0039438 A1 | 2/2004 | Alt |
| 2003/0004564 A1 | 1/2003 | Elkins et al. | 2004/0039441 A1 | 2/2004 | Rowland et al. |
| 2003/0006250 A1 | 1/2003 | Tapphorn et al. | 2004/0044397 A1 | 3/2004 | Stinson |
| 2003/0009214 A1 | 1/2003 | Shanley | 2004/0047980 A1 | 3/2004 | Pacetti et al. |
| 2003/0009233 A1 | 1/2003 | Blinn et al. | 2004/0058858 A1 | 3/2004 | Hu |
| 2003/0018380 A1 | 1/2003 | Craig et al. | 2004/0059290 A1 | 3/2004 | Palasis |
| 2003/0018381 A1 | 1/2003 | Whitcher et al. | 2004/0059407 A1 | 3/2004 | Escamilla et al. |
| 2003/0021820 A1 | 1/2003 | Ahola et al. | 2004/0059409 A1 | 3/2004 | Stenzel |
| 2003/0023300 A1 | 1/2003 | Bailey et al. | 2004/0067301 A1 | 4/2004 | Ding |
| 2003/0028242 A1 | 2/2003 | Vallana et al. | 2004/0071861 A1 | 4/2004 | Mandrusov et al. |
| 2003/0028243 A1 | 2/2003 | Bates et al. | 2004/0073284 A1 | 4/2004 | Bates et al. |
| 2003/0032892 A1 | 2/2003 | Erlach et al. | 2004/0073298 A1 | 4/2004 | Hossainy |
| 2003/0033007 A1 | 2/2003 | Sirhan et al. | 2004/0078071 A1 | 4/2004 | Escamilla et al. |
| 2003/0044446 A1 | 3/2003 | Moro et al. | 2004/0086674 A1 | 5/2004 | Holman |
| 2003/0047028 A1 | 3/2003 | Kunitake et al. | 2004/0088038 A1 | 5/2004 | Dehnad et al. |
| 2003/0047505 A1 | 3/2003 | Grimes et al. | 2004/0088041 A1 | 5/2004 | Stanford |
| 2003/0050687 A1 | 3/2003 | Schwade et al. | 2004/0092653 A1 | 5/2004 | Ruberti et al. |
| 2003/0059640 A1 | 3/2003 | Marton et al. | 2004/0093071 A1 | 5/2004 | Jang |
| 2003/0060871 A1 | 3/2003 | Hill et al. | 2004/0093076 A1 | 5/2004 | White et al. |
| 2003/0060873 A1 | 3/2003 | Gertner et al. | 2004/0098089 A1 | 5/2004 | Weber |
| 2003/0060877 A1 | 3/2003 | Falotico et al. | 2004/0098119 A1 | 5/2004 | Wang |
| 2003/0064095 A1 | 4/2003 | Martin et al. | 2004/0102758 A1 | 5/2004 | Davila et al. |
| 2003/0069631 A1 | 4/2003 | Stoll | 2004/0106984 A1 | 6/2004 | Stinson |
| 2003/0074053 A1 | 4/2003 | Palmaz et al. | 2004/0106985 A1 | 6/2004 | Jang |
| 2003/0074075 A1 | 4/2003 | Thomas et al. | 2004/0106987 A1 | 6/2004 | Palasis et al. |
| 2003/0077200 A1 | 4/2003 | Craig et al. | 2004/0106994 A1 | 6/2004 | De Maeztus Martinez et al. |
| 2003/0083614 A1 | 5/2003 | Eisert | 2004/0111150 A1 | 6/2004 | Berg et al. |
| 2003/0083646 A1 | 5/2003 | Sirhan et al. | 2004/0116999 A1 | 6/2004 | Ledergerber |
| 2003/0083731 A1 | 5/2003 | Kramer et al. | 2004/0117005 A1 | 6/2004 | Gadde et al. |
| 2003/0087024 A1 | 5/2003 | Flanagan | 2004/0117008 A1 | 6/2004 | Wnendt et al. |
| 2003/0088307 A1 | 5/2003 | Shulze et al. | 2004/0122504 A1 | 6/2004 | Hogendijk |
| 2003/0088312 A1 | 5/2003 | Kopia et al. | 2004/0126566 A1 | 7/2004 | Axen et al. |
| 2003/0100865 A1 | 5/2003 | Santini, Jr. et al. | 2004/0133270 A1 | 7/2004 | Grandt |
| 2003/0104028 A1 | 6/2003 | Hossainy et al. | 2004/0134886 A1 | 7/2004 | Wagner et al. |
| 2003/0105511 A1 | 6/2003 | Welsh et al. | 2004/0142014 A1 | 7/2004 | Litvack et al. |
| 2003/0108659 A1 | 6/2003 | Bales et al. | 2004/0143317 A1 | 7/2004 | Stinson et al. |
| 2003/0114917 A1 | 6/2003 | Holloway et al. | 2004/0143321 A1 | 7/2004 | Litvack et al. |
| 2003/0114921 A1 | 6/2003 | Yoon | 2004/0148010 A1 | 7/2004 | Rush |
| 2003/0118649 A1 | 6/2003 | Gao et al. | 2004/0148015 A1 | 7/2004 | Lye et al. |
| 2003/0125803 A1 | 7/2003 | Vallana et al. | 2004/0158308 A1 | 8/2004 | Hogendijk et al. |
| 2003/0130206 A1 | 7/2003 | Koziak et al. | 2004/0167572 A1 | 8/2004 | Roth et al. |
| 2003/0130718 A1 | 7/2003 | Palmas et al. | 2004/0167612 A1 | 8/2004 | Grignani et al. |
| 2003/0138645 A1 | 7/2003 | Gleason et al. | 2004/0171978 A1 | 9/2004 | Shalaby |
| 2003/0139799 A1 | 7/2003 | Ley et al. | 2004/0172124 A1 | 9/2004 | Vallana et al. |
| 2003/0144728 A1 | 7/2003 | Scheuermann et al. | 2004/0178523 A1 | 9/2004 | Kim et al. |
| 2003/0150380 A1 | 8/2003 | Yoe | 2004/0181252 A1 | 9/2004 | Boyle et al. |
| 2003/0153901 A1 | 8/2003 | Herweck et al. | 2004/0181275 A1 | 9/2004 | Noble et al. |
| 2003/0153971 A1 | 8/2003 | Chandrasekaran | 2004/0181276 A1 | 9/2004 | Brown et al. |
| 2003/0158598 A1 | 8/2003 | Ashton et al. | 2004/0185168 A1 | 9/2004 | Weber et al. |
| 2003/0167878 A1 | 9/2003 | Al-Salim et al. | 2004/0191293 A1 | 9/2004 | Claude |
| 2003/0170605 A1 | 9/2003 | Long et al. | 2004/0191404 A1 | 9/2004 | Hossainy et al. |
| 2003/0181975 A1 | 9/2003 | Ishii et al. | 2004/0202692 A1 | 10/2004 | Shanley et al. |
| 2003/0185895 A1 | 10/2003 | Lanphere et al. | 2004/0204750 A1 | 10/2004 | Dinh |
| 2003/0185964 A1 | 10/2003 | Weber et al. | 2004/0211362 A1 | 10/2004 | Castro et al. |
| 2003/0190406 A1 | 10/2003 | Hossainy et al. | 2004/0215169 A1 | 10/2004 | Li |
| 2003/0195613 A1 | 10/2003 | Curcio et al. | 2004/0215313 A1 | 10/2004 | Cheng |
| 2003/0203991 A1 | 10/2003 | Schottman et al. | 2004/0219214 A1 | 11/2004 | Gravett et al. |
| 2003/0204168 A1 | 10/2003 | Bosma et al. | 2004/0220510 A1 | 11/2004 | Koullick et al. |
| 2003/0208256 A1 | 11/2003 | DiMatteo et al. | 2004/0220662 A1 | 11/2004 | Dang et al. |
| 2003/0211135 A1 | 11/2003 | Greenhalgh et al. | 2004/0224001 A1 | 11/2004 | Pacetti et al. |
| 2003/0216803 A1 | 11/2003 | Ledergerber | 2004/0225346 A1 | 11/2004 | Mazumder et al. |
| 2003/0219562 A1 | 11/2003 | Rypacek et al. | 2004/0225347 A1 | 11/2004 | Lang |
| 2003/0225450 A1 | 12/2003 | Shulze et al. | 2004/0228905 A1 | 11/2004 | Greenspan et al. |
| 2003/0236323 A1 | 12/2003 | Ratner et al. | 2004/0230176 A1 | 11/2004 | Shanahan et al. |

| Publication No. | Date | Inventor | | Publication No. | Date | Inventor | |
|---|---|---|---|---|---|---|---|
| 2004/0230290 A1 | 11/2004 | Weber et al. | | 2005/0186250 A1 | 8/2005 | Gertner et al. | |
| 2004/0230293 A1 | 11/2004 | Yip et al. | | 2005/0187608 A1 | 8/2005 | O'Hara | |
| 2004/0234737 A1 | 11/2004 | Pacetti | | 2005/0192657 A1 | 9/2005 | Colen et al. | |
| 2004/0234748 A1 | 11/2004 | Stenzel | | 2005/0192664 A1 | 9/2005 | Eisert | |
| 2004/0236399 A1 | 11/2004 | Sundar | | 2005/0196424 A1 | 9/2005 | Chappa | |
| 2004/0236415 A1 | 11/2004 | Thomas | | 2005/0196518 A1 | 9/2005 | Stenzel | |
| 2004/0236416 A1 | 11/2004 | Falotico | | 2005/0197687 A1 | 9/2005 | Molaei et al. | |
| 2004/0237282 A1 | 12/2004 | Hines | | 2005/0197689 A1 | 9/2005 | Molaei | |
| 2004/0242106 A1 | 12/2004 | Rabasco et al. | | 2005/0203606 A1 | 9/2005 | VanCamp | |
| 2004/0243217 A1 | 12/2004 | Andersen et al. | | 2005/0208098 A1 | 9/2005 | Castro et al. | |
| 2004/0243241 A1 | 12/2004 | Istephanous | | 2005/0208100 A1* | 9/2005 | Weber et al. | 424/426 |
| 2004/0247671 A1 | 12/2004 | Prescott et al. | | 2005/0209681 A1 | 9/2005 | Curcio et al. | |
| 2004/0249444 A1 | 12/2004 | Reiss | | 2005/0211680 A1 | 9/2005 | Li et al. | |
| 2004/0249449 A1 | 12/2004 | Shanley et al. | | 2005/0214951 A1 | 9/2005 | Nahm et al. | |
| 2004/0254635 A1 | 12/2004 | Shanley et al. | | 2005/0216074 A1 | 9/2005 | Sahatjian et al. | |
| 2004/0261702 A1 | 12/2004 | Grabowy et al. | | 2005/0220853 A1 | 10/2005 | Dao et al. | |
| 2005/0002865 A1 | 1/2005 | Klaveness et al. | | 2005/0221072 A1 | 10/2005 | Dubrow et al. | |
| 2005/0004663 A1 | 1/2005 | Llanos et al. | | 2005/0228477 A1 | 10/2005 | Grainger et al. | |
| 2005/0010275 A1 | 1/2005 | Sahatjian et al. | | 2005/0228491 A1 | 10/2005 | Snyder et al. | |
| 2005/0015142 A1 | 1/2005 | Austin et al. | | 2005/0232968 A1 | 10/2005 | Palmaz et al. | |
| 2005/0019265 A1 | 1/2005 | Hammer et al. | | 2005/0233965 A1 | 10/2005 | Schwartz et al. | |
| 2005/0019371 A1 | 1/2005 | Anderson et al. | | 2005/0244459 A1 | 11/2005 | DeWitt et al. | |
| 2005/0020614 A1 | 1/2005 | Prescott et al. | | 2005/0251245 A1 | 11/2005 | Sieradzki et al. | |
| 2005/0021127 A1 | 1/2005 | Kawula | | 2005/0251249 A1 | 11/2005 | Sahatjian et al. | |
| 2005/0021128 A1 | 1/2005 | Nakahama et al. | | 2005/0255707 A1 | 11/2005 | Hart et al. | |
| 2005/0027350 A1 | 2/2005 | Momma et al. | | 2005/0261760 A1 | 11/2005 | Weber | |
| 2005/0033411 A1* | 2/2005 | Wu et al. | 623/1.15 | 2005/0266039 A1 | 12/2005 | Weber | |
| 2005/0033412 A1 | 2/2005 | Wu et al. | | 2005/0266040 A1 | 12/2005 | Gerberding | |
| 2005/0033417 A1 | 2/2005 | Borges et al. | | 2005/0267561 A1 | 12/2005 | Jones et al. | |
| 2005/0037047 A1 | 2/2005 | Song | | 2005/0271703 A1 | 12/2005 | Anderson et al. | |
| 2005/0038498 A1 | 2/2005 | Dubrow et al. | | 2005/0271706 A1 | 12/2005 | Anderson et al. | |
| 2005/0038505 A1* | 2/2005 | Shulze et al. | 623/1.42 | 2005/0276837 A1 | 12/2005 | Anderson et al. | |
| 2005/0042288 A1 | 2/2005 | Koblish et al. | | 2005/0278016 A1 | 12/2005 | Welsh et al. | |
| 2005/0055080 A1 | 3/2005 | Istephanous et al. | | 2005/0278021 A1 | 12/2005 | Bates et al. | |
| 2005/0055085 A1 | 3/2005 | Rivron et al. | | 2005/0281863 A1 | 12/2005 | Anderson et al. | |
| 2005/0060020 A1 | 3/2005 | Jenson | | 2005/0285073 A1 | 12/2005 | Singh et al. | |
| 2005/0060021 A1 | 3/2005 | O'Brien et al. | | 2005/0287188 A1 | 12/2005 | Anderson et al. | |
| 2005/0069630 A1 | 3/2005 | Fox et al. | | 2006/0003884 A1 | 1/2006 | Stenzel | |
| 2005/0070989 A1 | 3/2005 | Lye et al. | | 2006/0013850 A1 | 1/2006 | Domb | |
| 2005/0070990 A1 | 3/2005 | Stinson | | 2006/0015175 A1 | 1/2006 | Palmaz et al. | |
| 2005/0070996 A1* | 3/2005 | Dinh et al. | 623/1.42 | 2006/0015361 A1 | 1/2006 | Sattler et al. | |
| 2005/0072544 A1 | 4/2005 | Palmaz et al. | | 2006/0020742 A1 | 1/2006 | Au et al. | |
| 2005/0074479 A1 | 4/2005 | Weber et al. | | 2006/0025848 A1 | 2/2006 | Weber et al. | |
| 2005/0074545 A1 | 4/2005 | Thomas | | 2006/0035026 A1 | 2/2006 | Atanassoska et al. | |
| 2005/0077305 A1 | 4/2005 | Guevara | | 2006/0038027 A1 | 2/2006 | O'Connor et al. | |
| 2005/0079199 A1 | 4/2005 | Heruth et al. | | 2006/0051397 A1 | 3/2006 | Maier et al. | |
| 2005/0079201 A1 | 4/2005 | Rathenow et al. | | 2006/0052744 A1 | 3/2006 | Weber | |
| 2005/0079356 A1 | 4/2005 | Rathenow et al. | | 2006/0052863 A1 | 3/2006 | Harder et al. | |
| 2005/0087520 A1 | 4/2005 | Wang et al. | | 2006/0052864 A1 | 3/2006 | Harder et al. | |
| 2005/0092615 A1 | 5/2005 | Birdsall et al. | | 2006/0062820 A1 | 3/2006 | Gertner et al. | |
| 2005/0096731 A1 | 5/2005 | Looi et al. | | 2006/0069427 A1 | 3/2006 | Savage et al. | |
| 2005/0100577 A1 | 5/2005 | Parker et al. | | 2006/0075044 A1 | 4/2006 | Fox et al. | |
| 2005/0100609 A1 | 5/2005 | Claude | | 2006/0075092 A1 | 4/2006 | Kidokoro | |
| 2005/0102025 A1 | 5/2005 | Laroche et al. | | 2006/0079863 A1 | 4/2006 | Burgmeier et al. | |
| 2005/0106212 A1 | 5/2005 | Gertner et al. | | 2006/0085062 A1 | 4/2006 | Lee et al. | |
| 2005/0107870 A1 | 5/2005 | Wang et al. | | 2006/0085065 A1 | 4/2006 | Krause et al. | |
| 2005/0110214 A1 | 5/2005 | Shank et al. | | 2006/0088561 A1 | 4/2006 | Eini et al. | |
| 2005/0113936 A1 | 5/2005 | Brustad et al. | | 2006/0088566 A1 | 4/2006 | Parsonage et al. | |
| 2005/0119723 A1 | 6/2005 | Peacock | | 2006/0088567 A1 | 4/2006 | Warner et al. | |
| 2005/0129727 A1 | 6/2005 | Weber et al. | | 2006/0088666 A1 | 4/2006 | Kobrin et al. | |
| 2005/0131509 A1 | 6/2005 | Atanassoska et al. | | 2006/0093643 A1 | 5/2006 | Stenzel | |
| 2005/0131521 A1 | 6/2005 | Marton | | 2006/0093646 A1* | 5/2006 | Cima et al. | 424/425 |
| 2005/0131522 A1 | 6/2005 | Stinson et al. | | 2006/0095123 A1 | 5/2006 | Flanagan | |
| 2005/0136090 A1 | 6/2005 | Falotico et al. | | 2006/0100696 A1 | 5/2006 | Atanasoska et al. | |
| 2005/0137677 A1 | 6/2005 | Rush | | 2006/0115512 A1 | 6/2006 | Peacock et al. | |
| 2005/0137679 A1 | 6/2005 | Changelian et al. | | 2006/0121080 A1 | 6/2006 | Lye et al. | |
| 2005/0137684 A1 | 6/2005 | Changelian et al. | | 2006/0122694 A1 | 6/2006 | Stinson et al. | |
| 2005/0149102 A1 | 7/2005 | Radisch et al. | | 2006/0122697 A1* | 6/2006 | Shanley et al. | 623/1.42 |
| 2005/0149170 A1 | 7/2005 | Tassel et al. | | 2006/0125144 A1 | 6/2006 | Weber et al. | |
| 2005/0159804 A1 | 7/2005 | Lad et al. | | 2006/0127442 A1 | 6/2006 | Helmus | |
| 2005/0159805 A1 | 7/2005 | Weber et al. | | 2006/0127443 A1 | 6/2006 | Helmus | |
| 2005/0160600 A1 | 7/2005 | Bien et al. | | 2006/0129215 A1 | 6/2006 | Helmus et al. | |
| 2005/0163954 A1 | 7/2005 | Shaw | | 2006/0129225 A1 | 6/2006 | Kopia et al. | |
| 2005/0165467 A1 | 7/2005 | Hunter et al. | | 2006/0136048 A1 | 6/2006 | Pacetti et al. | |
| 2005/0165468 A1 | 7/2005 | Marton | | 2006/0140867 A1 | 6/2006 | Helfer et al. | |
| 2005/0165476 A1 | 7/2005 | Furst et al. | | 2006/0141156 A1 | 6/2006 | Viel et al. | |
| 2005/0171595 A1 | 8/2005 | Feldman et al. | | 2006/0142853 A1 | 6/2006 | Wang et al. | |
| 2005/0180919 A1 | 8/2005 | Tedeschi | | 2006/0153729 A1 | 7/2006 | Stinson et al. | |
| 2005/0182478 A1 | 8/2005 | Holman et al. | | 2006/0155361 A1 | 7/2006 | Schomig et al. | |

| | | | | | | |
|---|---|---|---|---|---|---|
| 2006/0167543 A1 | 7/2006 | Bailey et al. | | 2007/0224116 A1 | 9/2007 | Chandrasekaran et al. |
| 2006/0171985 A1 | 8/2006 | Richard et al. | | 2007/0224224 A1 | 9/2007 | Cordeira Da Silva et al. |
| 2006/0178727 A1 | 8/2006 | Richter | | 2007/0224235 A1 | 9/2007 | Tenney et al. |
| 2006/0184235 A1 | 8/2006 | Rivron et al. | | 2007/0224244 A1 | 9/2007 | Weber et al. |
| 2006/0193886 A1 | 8/2006 | Owens et al. | | 2007/0244569 A1 | 10/2007 | Weber et al. |
| 2006/0193887 A1 | 8/2006 | Owens et al. | | 2007/0254091 A1 | 11/2007 | Fredrickson et al. |
| 2006/0193888 A1 | 8/2006 | Lye et al. | | 2007/0255392 A1 | 11/2007 | Johnson |
| 2006/0193889 A1 | 8/2006 | Spradlin et al. | | 2007/0264303 A1 | 11/2007 | Atanasoska et al. |
| 2006/0193890 A1 | 8/2006 | Owens et al. | | 2007/0269480 A1 | 11/2007 | Richard et al. |
| 2006/0199876 A1 | 9/2006 | Troczynski et al. | | 2007/0299509 A1 | 12/2007 | Ding |
| 2006/0200229 A1 | 9/2006 | Burgermeister et al. | | 2008/0003251 A1 | 1/2008 | Zhou |
| 2006/0200231 A1 | 9/2006 | O'Brien et al. | | 2008/0004691 A1 | 1/2008 | Weber et al. |
| 2006/0210595 A1 | 9/2006 | Singhvi et al. | | 2008/0008654 A1 | 1/2008 | Clarke et al. |
| 2006/0212109 A1 | 9/2006 | Sirhan et al. | | 2008/0038146 A1 | 2/2008 | Wachter et al. |
| 2006/0222679 A1 | 10/2006 | Shanley et al. | | 2008/0050413 A1 | 2/2008 | Horvers et al. |
| 2006/0222844 A1 | 10/2006 | Stinson | | 2008/0050415 A1 | 2/2008 | Atanasoska et al. |
| 2006/0224234 A1 | 10/2006 | Jayaraman | | 2008/0051881 A1 | 2/2008 | Feng et al. |
| 2006/0229711 A1 | 10/2006 | Yan et al. | | 2008/0057103 A1 | 3/2008 | Roorda |
| 2006/0229713 A1 * | 10/2006 | Shanley et al. ............... 623/1.42 | | 2008/0058921 A1 | 3/2008 | Lindquist |
| 2006/0229715 A1 | 10/2006 | Istephanous et al. | | 2008/0069854 A1 | 3/2008 | Xiao et al. |
| 2006/0230476 A1 | 10/2006 | Atanasoska et al. | | 2008/0071348 A1 | 3/2008 | Boismier et al. |
| 2006/0233941 A1 | 10/2006 | Olson | | 2008/0071349 A1 | 3/2008 | Atanasoska et al. |
| 2006/0251701 A1 | 11/2006 | Lynn et al. | | 2008/0071350 A1 | 3/2008 | Stinson |
| 2006/0263512 A1 | 11/2006 | Glocker | | 2008/0071351 A1 | 3/2008 | Flanagan et al. |
| 2006/0263515 A1 | 11/2006 | Rieck et al. | | 2008/0071352 A1 | 3/2008 | Weber et al. |
| 2006/0264138 A1 | 11/2006 | Sowinski et al. | | 2008/0071353 A1 | 3/2008 | Weber et al. |
| 2006/0271169 A1 | 11/2006 | Lye et al. | | 2008/0071355 A1 | 3/2008 | Weber et al. |
| 2006/0275554 A1 | 12/2006 | Zhao et al. | | 2008/0071358 A1 | 3/2008 | Weber et al. |
| 2006/0276877 A1 | 12/2006 | Owens et al. | | 2008/0086199 A1 | 4/2008 | Dave et al. |
| 2006/0276878 A1 | 12/2006 | Owens et al. | | 2008/0086201 A1 | 4/2008 | Weber et al. |
| 2006/0276879 A1 | 12/2006 | Lye et al. | | 2008/0097577 A1 | 4/2008 | Atanasoska et al. |
| 2006/0276884 A1 | 12/2006 | Lye et al. | | 2008/0107890 A1 | 5/2008 | Bureau et al. |
| 2006/0276885 A1 | 12/2006 | Lye et al. | | 2008/0124373 A1 | 5/2008 | Xiao et al. |
| 2006/0276910 A1 | 12/2006 | Weber | | 2008/0140186 A1 | 6/2008 | Grignani et al. |
| 2006/0280770 A1 | 12/2006 | Hossainy et al. | | 2008/0145400 A1 | 6/2008 | Weber et al. |
| 2006/0292388 A1 | 12/2006 | Palumbo et al. | | 2008/0147177 A1 | 6/2008 | Scheuermann et al. |
| 2007/0003589 A1 | 1/2007 | Astafieva et al. | | 2008/0152929 A1 | 6/2008 | Zhao |
| 2007/0003817 A1 | 1/2007 | Umeda et al. | | 2008/0160259 A1 | 7/2008 | Nielson et al. |
| 2007/0032858 A1 | 2/2007 | Santos et al. | | 2008/0171929 A1 | 7/2008 | Katims |
| 2007/0032864 A1 | 2/2007 | Furst et al. | | 2008/0188836 A1 | 8/2008 | Weber et al. |
| 2007/0036905 A1 | 2/2007 | Kramer | | 2008/0241218 A1 | 10/2008 | McMorrow et al. |
| 2007/0038176 A1 | 2/2007 | Weber et al. | | 2008/0243231 A1 | 10/2008 | Flanagan et al. |
| 2007/0038289 A1 | 2/2007 | Nishide et al. | | 2008/0243240 A1 | 10/2008 | Doty et al. |
| 2007/0048452 A1 | 3/2007 | Feng et al. | | 2008/0249600 A1 | 10/2008 | Atanasoska et al. |
| 2007/0052497 A1 | 3/2007 | Tada | | 2008/0249615 A1 | 10/2008 | Weber |
| 2007/0055349 A1 | 3/2007 | Santos et al. | | 2008/0255508 A1 | 10/2008 | Wang |
| 2007/0055354 A1 | 3/2007 | Santos et al. | | 2008/0255657 A1 | 10/2008 | Gregorich et al. |
| 2007/0059435 A1 | 3/2007 | Santos et al. | | 2008/0262607 A1 | 10/2008 | Fricke |
| 2007/0065418 A1 | 3/2007 | Vallana et al. | | 2008/0275543 A1 | 11/2008 | Lenz et al. |
| 2007/0071789 A1 | 3/2007 | Pantelidis et al. | | 2008/0288048 A1 | 11/2008 | Rolando et al. |
| 2007/0072978 A1 | 3/2007 | Zoromski et al. | | 2008/0290467 A1 | 11/2008 | Shue et al. |
| 2007/0073385 A1 | 3/2007 | Schaeffer et al. | | 2008/0294236 A1 | 11/2008 | Anand et al. |
| 2007/0073390 A1 | 3/2007 | Lee | | 2008/0294246 A1 | 11/2008 | Scheuermann et al. |
| 2007/0106347 A1 | 5/2007 | Lin | | 2008/0306584 A1 | 12/2008 | Kramer-Brown |
| 2007/0110888 A1 | 5/2007 | Radhakrishnan et al. | | 2009/0012603 A1 | 1/2009 | Xu et al. |
| 2007/0112421 A1 | 5/2007 | O'Brien | | 2009/0018639 A1 | 1/2009 | Kuehling |
| 2007/0123973 A1 | 5/2007 | Roth et al. | | 2009/0018642 A1 | 1/2009 | Benco |
| 2007/0128245 A1 | 6/2007 | Rosenberg et al. | | 2009/0018644 A1 | 1/2009 | Weber et al. |
| 2007/0129789 A1 | 6/2007 | Cottone et al. | | 2009/0018647 A1 | 1/2009 | Benco et al. |
| 2007/0134288 A1 | 6/2007 | Parsonage et al. | | 2009/0028785 A1 | 1/2009 | Clarke |
| 2007/0135908 A1 | 6/2007 | Zhao | | 2009/0030504 A1 | 1/2009 | Weber et al. |
| 2007/0148251 A1 | 6/2007 | Hossainy et al. | | 2009/0076588 A1 | 3/2009 | Weber |
| 2007/0151093 A1 | 7/2007 | Curcio et al. | | 2009/0076595 A1 | 3/2009 | Lindquist et al. |
| 2007/0154513 A1 | 7/2007 | Atanasoska et al. | | 2009/0081450 A1 | 3/2009 | Ascher et al. |
| 2007/0156231 A1 | 7/2007 | Weber | | 2009/0112310 A1 | 4/2009 | Zhang |
| 2007/0173923 A1 | 7/2007 | Savage et al. | | 2009/0118809 A1 | 5/2009 | Scheuermann et al. |
| 2007/0181433 A1 | 8/2007 | Birdsall et al. | | 2009/0118812 A1 | 5/2009 | Kokate et al. |
| 2007/0190104 A1 | 8/2007 | Kamath et al. | | 2009/0118813 A1 | 5/2009 | Scheuermann et al. |
| 2007/0191923 A1 | 8/2007 | Weber et al. | | 2009/0118814 A1 | 5/2009 | Schoenle et al. |
| 2007/0191928 A1 | 8/2007 | Rolando et al. | | 2009/0118815 A1 | 5/2009 | Arcand et al. |
| 2007/0191931 A1 | 8/2007 | Weber et al. | | 2009/0118818 A1 | 5/2009 | Foss et al. |
| 2007/0191943 A1 | 8/2007 | Shrivastava et al. | | 2009/0118820 A1 | 5/2009 | Gregorich et al. |
| 2007/0198081 A1 | 8/2007 | Castro et al. | | 2009/0118821 A1 | 5/2009 | Scheuermann et al. |
| 2007/0202466 A1 | 8/2007 | Schwarz et al. | | 2009/0118822 A1 | 5/2009 | Holman et al. |
| 2007/0207186 A1 | 9/2007 | Scanlon et al. | | 2009/0118823 A1 | 5/2009 | Atanasoska et al. |
| 2007/0208412 A1 | 9/2007 | Elmaleh | | 2009/0123517 A1 | 5/2009 | Flanagan et al. |
| 2007/0212547 A1 | 9/2007 | Fredrickson et al. | | 2009/0123521 A1 | 5/2009 | Weber et al. |
| 2007/0213827 A1 | 9/2007 | Arramon | | 2009/0138077 A1 | 5/2009 | Weber et al. |
| 2007/0219626 A1 | 9/2007 | Rolando et al. | | 2009/0149942 A1 | 6/2009 | Edelman et al. |

| | | |
|---|---|---|
| 2009/0157165 A1 | 6/2009 | Miller et al. |
| 2009/0157166 A1 | 6/2009 | Singhal et al. |
| 2009/0157172 A1* | 6/2009 | Kokate et al. ............... 623/1.43 |
| 2009/0177273 A1 | 7/2009 | Piveteau et al. |
| 2009/0186068 A1 | 7/2009 | Miller et al. |
| 2009/0192593 A1* | 7/2009 | Meyer et al. ............... 623/1.42 |
| 2009/0202610 A1 | 8/2009 | Wilson |
| 2009/0208428 A1 | 8/2009 | Hill et al. |
| 2009/0220612 A1 | 9/2009 | Perera |
| 2009/0259300 A1 | 10/2009 | Dorogy, Jr. et al. |
| 2009/0264975 A1 | 10/2009 | Flanagan et al. |
| 2009/0281613 A1 | 11/2009 | Atanasoska et al. |
| 2009/0287301 A1 | 11/2009 | Weber |
| 2009/0306765 A1 | 12/2009 | Weber |
| 2009/0317766 A1 | 12/2009 | Heidenau et al. |
| 2010/0008970 A1 | 1/2010 | O'Brien et al. |
| 2010/0030326 A1 | 2/2010 | Radhakrishnan et al. |
| 2010/0042206 A1 | 2/2010 | Yadav et al. |
| 2010/0057197 A1 | 3/2010 | Weber et al. |
| 2010/0070022 A1 | 3/2010 | Kuehling |
| 2010/0070026 A1 | 3/2010 | Ito et al. |
| 2010/0131050 A1 | 5/2010 | Zhao |

FOREIGN PATENT DOCUMENTS

| | | |
|---|---|---|
| AT | 288234 | 2/2005 |
| AU | 4825696 | 10/1996 |
| AU | 5588896 | 12/1996 |
| AU | 5266698 | 6/1998 |
| AU | 6663298 | 9/1998 |
| AU | 716005 | 2/2000 |
| AU | 5686499 | 3/2000 |
| AU | 2587100 | 5/2000 |
| AU | 2153600 | 6/2000 |
| AU | 1616201 | 5/2001 |
| AU | 737252 | 8/2001 |
| AU | 2317701 | 8/2001 |
| AU | 5215401 | 9/2001 |
| AU | 5890401 | 12/2001 |
| AU | 3597401 | 6/2002 |
| AU | 2002353068 | 3/2003 |
| AU | 2002365875 | 6/2003 |
| AU | 2003220153 | 9/2003 |
| AU | 2003250913 | 1/2004 |
| AU | 770395 | 2/2004 |
| AU | 2003249017 | 2/2004 |
| AU | 2003256499 | 2/2004 |
| AU | 771367 | 3/2004 |
| AU | 2003271633 | 4/2004 |
| AU | 2003272710 | 4/2004 |
| AU | 2003285195 | 6/2004 |
| AU | 2003287633 | 6/2004 |
| AU | 2003290675 | 6/2004 |
| AU | 2003290676 | 6/2004 |
| AU | 2003291470 | 6/2004 |
| AU | 2003295419 | 6/2004 |
| AU | 2003295535 | 6/2004 |
| AU | 2003295763 | 6/2004 |
| AU | 2004202073 | 6/2004 |
| AU | 2003300323 | 7/2004 |
| AU | 2004213021 | 9/2004 |
| AU | 2003293557 | 1/2005 |
| AU | 780539 | 3/2005 |
| BR | 8701135 | 1/1988 |
| BR | 207321 | 2/2004 |
| BR | 16957 | 6/2004 |
| BR | 316065 | 9/2005 |
| BR | 316102 | 9/2005 |
| CA | 1283505 | 4/1991 |
| CA | 2172187 | 10/1996 |
| CA | 2178541 | 12/1996 |
| CA | 2234787 | 10/1998 |
| CA | 2235031 | 10/1998 |
| CA | 2238837 | 2/1999 |
| CA | 2340652 | 3/2000 |
| CA | 2392006 | 5/2001 |
| CA | 2337565 | 8/2001 |
| CA | 2409862 | 11/2001 |
| CA | 2353197 | 1/2002 |
| CA | 2429356 | 8/2002 |
| CA | 2435306 | 8/2002 |
| CA | 2436241 | 8/2002 |
| CA | 2438095 | 8/2002 |
| CA | 2460334 | 3/2003 |
| CA | 2425665 | 4/2003 |
| CA | 2465704 | 4/2003 |
| CA | 2464906 | 5/2003 |
| CA | 2468677 | 6/2003 |
| CA | 2469744 | 6/2003 |
| CA | 2484383 | 1/2004 |
| CA | 2497602 | 4/2004 |
| CA | 2499976 | 4/2004 |
| CA | 2503625 | 5/2004 |
| CA | 2504524 | 5/2004 |
| CA | 2505576 | 5/2004 |
| CA | 2513721 | 5/2004 |
| CA | 2505080 | 6/2004 |
| CA | 2506622 | 6/2004 |
| CA | 2455670 | 7/2004 |
| CA | 2508247 | 7/2004 |
| CA | 2458172 | 8/2004 |
| CA | 2467797 | 11/2004 |
| CA | 2258898 | 1/2005 |
| CA | 2308177 | 1/2005 |
| CA | 2475968 | 1/2005 |
| CA | 2489668 | 6/2005 |
| CA | 2490170 | 6/2005 |
| CA | 2474367 | 1/2006 |
| CA | 2374090 | 5/2007 |
| CA | 2282748 | 11/2007 |
| CA | 2336650 | 1/2008 |
| CA | 2304325 | 5/2008 |
| CN | 1430491 | 7/2003 |
| CN | 1547490 | 11/2004 |
| CN | 1575154 | 2/2005 |
| CN | 1585627 | 2/2005 |
| CN | 1669537 | 9/2005 |
| DE | 3516411 | 11/1986 |
| DE | 3608158 | 11/1987 |
| DE | 19916086 | 10/1999 |
| DE | 19855421 | 5/2000 |
| DE | 19916315 | 9/2000 |
| DE | 9422438 | 4/2002 |
| DE | 1096902 | 5/2002 |
| DE | 10064596 | 6/2002 |
| DE | 10107339 | 9/2002 |
| DE | 69712063 | 10/2002 |
| DE | 10127011 | 12/2002 |
| DE | 10150995 | 4/2003 |
| DE | 69807634 | 5/2003 |
| DE | 69431457 | 6/2003 |
| DE | 10200387 | 8/2003 |
| DE | 69719161 | 10/2003 |
| DE | 02704283 | 4/2004 |
| DE | 60106962 | 4/2005 |
| DE | 60018318 | 12/2005 |
| DE | 69732439 | 1/2006 |
| DE | 69828798 | 1/2006 |
| DE | 102004044738 | 3/2006 |
| DE | 69830605 | 5/2006 |
| DE | 102005010100 | 9/2006 |
| DE | 602005001867 | 5/2008 |
| DE | 69829015 | 3/2009 |
| DK | 127987 | 9/1987 |
| DK | 914092 | 8/2002 |
| EP | 0222853 | 5/1987 |
| EP | 129147 | 1/1990 |
| EP | 734721 | 10/1996 |
| EP | 650604 | 9/1998 |
| EP | 865762 | 9/1998 |
| EP | 875217 | 11/1998 |
| EP | 633840 | 11/1999 |
| EP | 953320 | 11/1999 |
| EP | 971644 | 1/2000 |
| EP | 982041 | 3/2000 |
| EP | 1105169 | 6/2001 |
| EP | 1124594 | 8/2001 |
| EP | 1127582 | 8/2001 |
| EP | 1131127 | 9/2001 |

| | | | | | |
|---|---|---|---|---|---|
| EP | 1132058 | 9/2001 | EP | 1621603 | 2/2006 |
| EP | 1150738 | 11/2001 | EP | 1218665 | 5/2006 |
| EP | 1172074 | 1/2002 | EP | 1222941 | 5/2006 |
| EP | 1181943 | 2/2002 | EP | 1359867 | 5/2006 |
| EP | 914092 | 4/2002 | EP | 1656961 | 5/2006 |
| EP | 1216665 | 6/2002 | EP | 1277449 | 6/2006 |
| EP | 747069 | 9/2002 | EP | 836839 | 7/2006 |
| EP | 0920342 | 9/2002 | EP | 1684817 | 8/2006 |
| EP | 1242130 | 9/2002 | EP | 1687042 | 8/2006 |
| EP | 0623354 | 10/2002 | EP | 907339 | 11/2006 |
| EP | 0806211 | 10/2002 | EP | 1359865 | 11/2006 |
| EP | 1275352 | 1/2003 | EP | 1214108 | 1/2007 |
| EP | 850604 | 2/2003 | EP | 1416885 | 1/2007 |
| EP | 1280512 | 2/2003 | EP | 1441667 | 1/2007 |
| EP | 1280568 | 2/2003 | EP | 1192957 | 2/2007 |
| EP | 1280569 | 2/2003 | EP | 1236447 | 2/2007 |
| EP | 1294309 | 3/2003 | EP | 1764116 | 3/2007 |
| EP | 824900 | 4/2003 | EP | 1185215 | 4/2007 |
| EP | 1308179 | 5/2003 | EP | 1442757 | 4/2007 |
| EP | 1310242 | 5/2003 | EP | 1786363 | 5/2007 |
| EP | 1314405 | 5/2003 | EP | 1787602 | 5/2007 |
| EP | 1316323 | 6/2003 | EP | 1788973 | 5/2007 |
| EP | 1339448 | 9/2003 | EP | 1796754 | 6/2007 |
| EP | 1347791 | 10/2003 | EP | 1330273 | 7/2007 |
| EP | 1347792 | 10/2003 | EP | 900060 | 8/2007 |
| EP | 1348402 | 10/2003 | EP | 1355588 | 8/2007 |
| EP | 1348405 | 10/2003 | EP | 1355589 | 8/2007 |
| EP | 1359864 | 11/2003 | EP | 1561436 | 8/2007 |
| EP | 1365710 | 12/2003 | EP | 1863408 | 12/2007 |
| EP | 1379290 | 1/2004 | EP | 1071490 | 1/2008 |
| EP | 902666 | 2/2004 | EP | 1096902 | 1/2008 |
| EP | 1460972 | 2/2004 | EP | 895762 | 2/2008 |
| EP | 815806 | 3/2004 | EP | 916317 | 2/2008 |
| EP | 1400219 | 3/2004 | EP | 1891988 | 2/2008 |
| EP | 950386 | 4/2004 | EP | 1402849 | 4/2008 |
| EP | 1461165 | 4/2004 | EP | 1466634 | 7/2008 |
| EP | 1416884 | 5/2004 | EP | 1572032 | 7/2008 |
| EP | 1424957 | 6/2004 | EP | 1527754 | 8/2008 |
| EP | 1429816 | 6/2004 | EP | 1968662 | 9/2008 |
| EP | 1448116 | 8/2004 | EP | 1980223 | 10/2008 |
| EP | 1448118 | 8/2004 | EP | 1988943 | 11/2008 |
| EP | 1449545 | 8/2004 | EP | 1490125 | 1/2009 |
| EP | 1449546 | 8/2004 | EP | 1829626 | 2/2009 |
| EP | 1254674 | 9/2004 | EP | 1229901 | 3/2009 |
| EP | 1453557 | 9/2004 | EP | 1128785 | 4/2009 |
| EP | 1457214 | 9/2004 | EP | 2051750 | 4/2009 |
| EP | 975340 | 10/2004 | EP | 1427353 | 5/2009 |
| EP | 1319416 | 11/2004 | ES | 2169012 | 7/2002 |
| EP | 1476882 | 11/2004 | FR | 2867059 | 9/2005 |
| EP | 1479402 | 11/2004 | GB | 2397233 | 7/2004 |
| EP | 1482867 | 12/2004 | JP | 361652 | 11/1988 |
| EP | 1011529 | 1/2005 | JP | 7002180 | 1/1995 |
| EP | 0875218 | 2/2005 | JP | 3673973 | 2/1996 |
| EP | 1181903 | 2/2005 | JP | 3249383 | 10/1996 |
| EP | 1504775 | 2/2005 | JP | 10295824 | 11/1998 |
| EP | 1042997 | 3/2005 | JP | 11188109 | 7/1999 |
| EP | 1754684 | 3/2005 | JP | 20000312721 | 11/2000 |
| EP | 1520594 | 4/2005 | JP | 2001098308 | 4/2001 |
| EP | 1521603 | 4/2005 | JP | 2001522640 | 11/2001 |
| EP | 1028672 | 6/2005 | JP | 2002065862 | 3/2002 |
| EP | 1539041 | 6/2005 | JP | 2002519139 | 7/2002 |
| EP | 1543798 | 6/2005 | JP | 2002523147 | 7/2002 |
| EP | 1550472 | 6/2005 | JP | 2003024449 | 1/2003 |
| EP | 1328213 | 7/2005 | JP | 2003521274 | 7/2003 |
| EP | 1551569 | 7/2005 | JP | 2003290361 | 10/2003 |
| EP | 1554992 | 7/2005 | JP | 2003533333 | 11/2003 |
| EP | 1560613 | 8/2005 | JP | 2004500925 | 1/2004 |
| EP | 1562519 | 8/2005 | JP | 2004522559 | 7/2004 |
| EP | 1562654 | 8/2005 | JP | 2004223264 | 8/2004 |
| EP | 1570808 | 9/2005 | JP | 2004275748 | 10/2004 |
| EP | 1575631 | 9/2005 | JP | 2004267750 | 11/2004 |
| EP | 1575638 | 9/2005 | JP | 2004305753 | 11/2004 |
| EP | 1575642 | 9/2005 | JP | 2005501654 | 1/2005 |
| EP | 900059 | 10/2005 | JP | 2005502426 | 1/2005 |
| EP | 1581147 | 10/2005 | JP | 2005040584 | 2/2005 |
| EP | 1586286 | 10/2005 | JP | 2005503184 | 2/2005 |
| EP | 1254673 | 11/2005 | JP | 2005503240 | 2/2005 |
| EP | 1261297 | 11/2005 | JP | 2005507285 | 3/2005 |
| EP | 927006 | 1/2006 | JP | 2005511139 | 4/2005 |

| | | | | | | |
|---|---|---|---|---|---|---|
| JP | 2005511242 | 4/2005 | | WO | WO03/035131 | 5/2003 |
| JP | 2005131364 | 5/2005 | | WO | WO03/037220 | 5/2003 |
| JP | 2005152526 | 6/2005 | | WO | WO03/037221 | 5/2003 |
| JP | 2005152527 | 6/2005 | | WO | WO03/037223 | 5/2003 |
| JP | 2005199054 | 7/2005 | | WO | WO03/037398 | 5/2003 |
| JP | 2005199058 | 7/2005 | | WO | WO03/039407 | 5/2003 |
| JP | 2008516726 | 5/2008 | | WO | WO03/045582 | 6/2003 |
| KR | 2002/0066996 | 8/2002 | | WO | WO03/047463 | 6/2003 |
| KR | 2004/0066409 | 7/2004 | | WO | WO03/051233 | 6/2003 |
| KR | 2005/0117361 | 12/2005 | | WO | WO03/055414 | 7/2003 |
| NZ | 331388 | 1/2000 | | WO | WO03/061755 | 7/2003 |
| SU | 393044 | 12/1973 | | WO | WO03/072287 | 9/2003 |
| WO | WO86/06617 | 11/1986 | | WO | WO03/077802 | 9/2003 |
| WO | WO93/06792 | 4/1993 | | WO | WO03/083181 | 10/2003 |
| WO | WO93/07934 | 4/1993 | | WO | WO03/094774 | 11/2003 |
| WO | WO93/16656 | 9/1993 | | WO | WO2004/004602 | 1/2004 |
| WO | WO94/16646 | 8/1994 | | WO | WO2004/004603 | 1/2004 |
| WO | WO95/03083 | 2/1995 | | WO | WO2004/006491 | 1/2004 |
| WO | WO96/04952 | 2/1996 | | WO | WO2004/006807 | 1/2004 |
| WO | WO96/09086 | 3/1996 | | WO | WO2004/006976 | 1/2004 |
| WO | WO96/32907 | 10/1996 | | WO | WO2004/006983 | 1/2004 |
| WO | WO97/41916 | 11/1997 | | WO | WO2004/010900 | 2/2004 |
| WO | WO98/17331 | 4/1998 | | WO | WO2004/014554 | 2/2004 |
| WO | WO98/18408 | 5/1998 | | WO | WO2004/026177 | 4/2004 |
| WO | WO98/23228 | 6/1998 | | WO | WO2004/028347 | 4/2004 |
| WO | WO98/36784 | 8/1998 | | WO | WO2004/028587 | 4/2004 |
| WO | WO98/38946 | 9/1998 | | WO | WO2004/043292 | 5/2004 |
| WO | WO98/38947 | 9/1998 | | WO | WO2004/043298 | 5/2004 |
| WO | WO98/40033 | 9/1998 | | WO | WO2004/043300 | 5/2004 |
| WO | WO98/57680 | 12/1998 | | WO | WO2004/043509 | 5/2004 |
| WO | WO99/16386 | 4/1999 | | WO | WO2004/043511 | 5/2004 |
| WO | WO99/23977 | 5/1999 | | WO | WO2004/045464 | 6/2004 |
| WO | WO99/42631 | 8/1999 | | WO | WO2004/045668 | 6/2004 |
| WO | WO99/49928 | 10/1999 | | WO | WO2004/058100 | 7/2004 |
| WO | WO99/52471 | 10/1999 | | WO | WO2004/060428 | 7/2004 |
| WO | WO99/62432 | 12/1999 | | WO | WO2004/064911 | 8/2004 |
| WO | WO00/01322 | 1/2000 | | WO | WO2004/071548 | 8/2004 |
| WO | WO00/10622 | 3/2000 | | WO | WO2004/072104 | 8/2004 |
| WO | WO00/25841 | 5/2000 | | WO | WO2004/073768 | 9/2004 |
| WO | WO00/27303 | 5/2000 | | WO | WO2004/080579 | 9/2004 |
| WO | WO00/30710 | 6/2000 | | WO | WO2004/087251 | 10/2004 |
| WO | WO00/48660 | 8/2000 | | WO | WO2004/096176 | 11/2004 |
| WO | WO00/64506 | 11/2000 | | WO | WO2004/105639 | 12/2004 |
| WO | WO01/35928 | 5/2001 | | WO | WO2004/108021 | 12/2004 |
| WO | WO01/41827 | 6/2001 | | WO | WO2004/108186 | 12/2004 |
| WO | WO01/45862 | 6/2001 | | WO | WO2004/108346 | 12/2004 |
| WO | WO01/45763 | 7/2001 | | WO | WO2004/110302 | 12/2004 |
| WO | WO01/66036 | 9/2001 | | WO | WO2005/004754 | 1/2005 |
| WO | WO01/80920 | 11/2001 | | WO | WO2005/006325 | 1/2005 |
| WO | WO01/87263 | 11/2001 | | WO | WO2005/011529 | 2/2005 |
| WO | WO01/87342 | 11/2001 | | WO | WO2005/014892 | 2/2005 |
| WO | WO01/87374 | 11/2001 | | WO | WO2005/027794 | 3/2005 |
| WO | WO01/89417 | 11/2001 | | WO | WO2005/032456 | 4/2005 |
| WO | WO01/89420 | 11/2001 | | WO | WO2005/034806 | 4/2005 |
| WO | WO02/26162 | 4/2002 | | WO | WO2005/042049 | 5/2005 |
| WO | WO02/30487 | 4/2002 | | WO | WO2005/044361 | 5/2005 |
| WO | WO02/38827 | 5/2002 | | WO | WO2005/049520 | 6/2005 |
| WO | WO02/42521 | 5/2002 | | WO | WO2005/051450 | 6/2005 |
| WO | WO02/43796 | 6/2002 | | WO | WO2005/053766 | 6/2005 |
| WO | WO02/47581 | 6/2002 | | WO | WO2005/063318 | 7/2005 |
| WO | WO02/58753 | 8/2002 | | WO | WO2005/072437 | 8/2005 |
| WO | WO02/60349 | 8/2002 | | WO | WO2005/082277 | 9/2005 |
| WO | WO02/60350 | 8/2002 | | WO | WO2005/082283 | 9/2005 |
| SU | WO02/60506 | 8/2002 | | WO | WO2005/086733 | 9/2005 |
| WO | WO02/64019 | 8/2002 | | WO | WO2005/089825 | 9/2005 |
| WO | WO02/65947 | 8/2002 | | WO | WO2005/091834 | 10/2005 |
| WO | WO02/69848 | 9/2002 | | WO | WO2005/099621 | 10/2005 |
| WO | WO02/74431 | 9/2002 | | WO | WO2005/099626 | 10/2005 |
| WO | WO02/76525 | 10/2002 | | WO | WO2005/110285 | 11/2005 |
| WO | WO02/78668 | 10/2002 | | WO | WO2005/115276 | 12/2005 |
| WO | WO02/83039 | 10/2002 | | WO | WO2005/115496 | 12/2005 |
| WO | WO02/85253 | 10/2002 | | WO | WO2005/117752 | 12/2005 |
| WO | WO02/85424 | 10/2002 | | WO | WO2006/014969 | 2/2006 |
| WO | WO02/85532 | 10/2002 | | WO | WO2006/015161 | 2/2006 |
| WO | WO02/96389 | 12/2002 | | WO | WO2006/020742 | 2/2006 |
| WO | WO03/009779 | 2/2003 | | WO | WO2006/029364 | 3/2006 |
| WO | WO03/022178 | 3/2003 | | WO | WO2006/029708 | 3/2006 |
| WO | WO03/024357 | 3/2003 | | WO | WO2006/036801 | 4/2006 |
| WO | WO03/026713 | 4/2003 | | WO | WO2006/055237 | 5/2006 |

| | | |
|---|---|---|
| WO | WO2006/061598 | 6/2006 |
| WO | WO2006/063157 | 6/2006 |
| WO | WO2006/063158 | 6/2006 |
| WO | WO2006/083418 | 8/2006 |
| WO | WO2006/104644 | 10/2006 |
| WO | WO2006/104976 | 10/2006 |
| WO | WO2006/105256 | 10/2006 |
| WO | WO2006/107677 | 10/2006 |
| WO | WO2006/116752 | 11/2006 |
| WO | WO2006/124365 | 11/2006 |
| WO | WO2007/016961 | 2/2007 |
| WO | WO2007/034167 | 3/2007 |
| WO | WO2007/070666 | 6/2007 |
| WO | WO2007/095167 | 8/2007 |
| WO | WO2007/124137 | 11/2007 |
| WO | WO2007/126768 | 11/2007 |
| WO | WO2007/130786 | 11/2007 |
| WO | WO2007/133520 | 11/2007 |
| WO | WO2007/143433 | 12/2007 |
| WO | WO2007/145961 | 12/2007 |
| WO | WO2007/147246 | 12/2007 |
| WO | WO2008/002586 | 1/2008 |
| WO | WO2008/002778 | 1/2008 |
| WO | WO2008/024149 | 2/2008 |
| WO | WO2008/024477 | 2/2008 |
| WO | WO2008/024669 | 2/2008 |
| WO | WO2008/033711 | 3/2008 |
| WO | WO2008/034048 | 3/2008 |
| WO | WO2008/036549 | 3/2008 |
| WO | WO2008/039319 | 4/2008 |
| WO | WO2008/045184 | 4/2008 |
| WO | WO2008/057991 | 5/2008 |
| WO | WO2008/061017 | 5/2008 |
| WO | WO2008/063539 | 5/2008 |
| WO | WO2008/082698 | 7/2008 |
| WO | WO2008/106223 | 9/2008 |
| WO | WO2008/108987 | 9/2008 |
| WO | WO2008/124513 | 10/2008 |
| WO | WO2008/124519 | 10/2008 |
| WO | WO2008/140482 | 11/2008 |
| WO | WO2008/147848 | 12/2008 |
| WO | WO2008/147853 | 12/2008 |
| WO | WO2009/009627 | 1/2009 |
| WO | WO2009/009628 | 1/2009 |
| WO | WO2009/012353 | 1/2009 |
| WO | WO2009/014692 | 1/2009 |
| WO | WO2009/014696 | 1/2009 |
| WO | WO2009/020520 | 2/2009 |
| WO | WO2009/059081 | 5/2009 |
| WO | WO2009/059085 | 5/2009 |
| WO | WO2009/059086 | 5/2009 |
| WO | WO2009/059098 | 5/2009 |
| WO | WO2009/059129 | 5/2009 |
| WO | WO2009/059141 | 5/2009 |
| WO | WO2009/059146 | 5/2009 |
| WO | WO2009/059165 | 5/2009 |
| WO | WO2009/059166 | 5/2009 |
| WO | WO2009/059180 | 5/2009 |
| WO | WO2009/059196 | 5/2009 |
| WO | WO2009/089382 | 7/2009 |
| WO | WO2009/091384 | 7/2009 |
| WO | WO2009/094270 | 7/2009 |
| WO | WO2009/126766 | 10/2009 |
| ZA | 9710342 | 6/1998 |

OTHER PUBLICATIONS

"Cyclic voltammetry"—from Wikipedia, (http://en.wikipedia.org/wiki/Cyclic_voltammetry), pp. 1-3, (downloaded [2007]).
"Electrophoretic deposition"—from Wikipedia, (http://en.wikipedia.org/wiki/electrophoretic_deposition), pp. 1-8, (downloaded [2007]).
"Impressive Progress in Interventional Cardiology—From 1st Balloon Inflation to First Bioabsorbable Stent," Medical News Today, pp. 1-2, May 15, 2006, (http://www.medicalnewstoday.com/articles/43313.php).
"JOMED Starts Clinical Studies on Tacrolimus-Eluting Coronary Stents," Jomed Press Release, 2 pages, Jan. 14, 2002.
"Nano PLD," PVD Products, Inc. Wilmington, MA, pp. 1-2, (2003).
"Sputtering," Wikipedia.com, (http://en.wikipedia.org/wiki/Sputtering), pp. 1-5, (downloaded [2009]).
"Ultraviolet-Ozone Surface Treatment," Three Bond Technical News #17, pp. 1-10, Issued Mar. 20, 1987, (http://www.threebond.co.jp/en/technical/technicalnews/pdf/tech17.pdf).
Abbott et al., "Voltammetric and impedance studies of the electropolishing of type 316 stainless steel in a choline chloride based ionic liquid," Electrochimica Acta, vol. 51, pp. 4420-4425, (2006).
Abstract: "Edelstahlfreier stent aus niobium mit iridiumoxyd (IrOx)-beschichtung: Erste Ergebnisse der LUSTY-studie", (Stainless steel-free Stent out of niobium with iridiumoxyd (IrOx)-coating: Initial results of the LUSTY-study), Annual Meeting of the German Society for Cardiology, Apr. 24-26, 2003.
Adanur et al., "Nanocomposite Fiber Based Web and Membrane Formation and Characterization," Journal of Industrial Textiles, vol. 36, No. 4, pp. 311-327, Apr. 2007.
Advincula et al., "Surface modification of surface sol-gel derived titanium oxide films by self-assembled monolayers (SAMs) and non-specific protein adsorption studies," Colloids and Surfaces B: Biointerfaces, vol. 42, pp. 29-43, (2005).
Akhras, "Bare metal stent, lunar IrOx2 coated or drug-eluting stent for patients with CAD?", PowerPoint presentation, pp. 1-20, Oct., 2006.
Akhras, Comparison of Iridiumoxide Coated Stent with Paclitaxel-Eluting Stent and a Bare Metal Stent in Patients With Coronary Artery Disease; Abstract, 1 page, Oct. 2006.
Al-Lamee, "Programmable Elution Profile Coating for Drug-Eluting Stents," Medical Device Technology: Materials, pp. 12-15, Mar. 2005.
Amanatides et al., "Electrical and optical properties of CH4/H2 RF plasmas for diamond-like thin film deposition," Diamond & Related materials, vol. 14, pp. 292-295, (2005).
Amberg et al., "Silver Deposition on Temperature Sensitive Substrates by Means of an Inverted Cylindrical Magnetron," Poster, 1 page, 2003.
Anders, "Ion Plating and Beyond: Pushing the Limits of Energetic Deposition," Vacuum Technology & Coating, pp. 41-46, Dec. 2002.
Andersson et al., "Influence of Systematically Varied Nanoscale Topography on the Morphology of Epithelial Cells," IEEE Transactions on Nanobioscience, vol. 2, No. 2, pp. 49-57, Jun. 2003.
Andersson et al., "Nanoscale features influence epithelial cell morphology and cytokine production," Biomaterials, 2003. vol. 24, No. 20, pp. 3427-3436, (2003).
Annis et al., "An Elastomeric Vascular Prosthesis," Transactions—American Society for Artificial Internal Organs. vol. XXIV, pp. 209-214, (1978).
Ansell et al., "X-Ray Rhotoelectron Spectroscopic Studies of Tin Electrodes after Polarization in Sodium Hydroxide Solution," Journal of Electrochemical Society: Electrochemical Science and Technology, vol. 124, No. 9, pp. 1360-1364, Sep. 1977.
Antunes et al., "Characterization of Corrosion Products Formed on Steels in The First Months of Atmospheric Exposure", Materia, vol. 8, No. 1, pp. 27-34, (2003).
Armani et al., "Microfabrication Technology for Polycaprolactone, a Biodegradable Polymer," Journal of Micromechanics and Microengineering, vol. 10, pp. 80-84, (2000).
Arnold et al., "Activation of Integrin Function by Nanopatterned Adhesive Interface," ChemPhysChem, vol. 5, pp. 383-388, (2004).
Ashfold et al., "Pulsed laser ablation and deposition of thin films," Chem. Soc. Rev., vol. 33, pp. 23-31, (2004).
Asoh et al., "Conditions for Fabrication of Ideally Ordered Anodic Porous Alumina Using Pretextured A1," Journal of the Electrochemical Society, vol. 148, pp. B152-B156, (2001).
Atanasoska et al., "XPS Studies on Conducting Polymers: Polypyrrole Films Doped with Perchlorate and Polymeric Anions," Chemistry Materials vol. 4, pp. 988-994, (1992).
Aughenbaugh et al., "Silica sol-gel for the controlled release of antibiotics. II. The effect of synthesis parameters on the in vitro release kinetics of vancomycin," Journal of Biomedical Materials Research, vol. 57, No. 3, pp. 321-326, Dec. 5, 2001.

Awad et al., "Deposition of duplex A12O3/TiN coatings on aluminum alloys for tribological applications using a combined microplasma oxidation (MPO) and arc ion plating (AIP)," Wear, vol. 260, pp. 215-222, (2006).

AxynTec product review, AxynTec Dunnschichttechnik GmbH (www.axyntec.de), pp. 1-8, (2002).

Ayon et al., "Drug loading of nonopouros TiO2 films," Institute of Physics Publishing, Biomedical Materials, vol. 1, pp. L11-L15, (2006).

Azom, "Porous Coatings for Improved Implant Life—Total Hip Replacements," pp. 1-7, [downloaded Sep. 1, 2005], (http://www.azom.com/Details.asp?ArticleID=1900).

Bak et al., "Electrodeposition of polymer next to the three-phase boundary," Electrochemisty Communications, vol. 7, pp. 1098-1104, (2005).

Balamuguran et al., "Bioactive Sol-Gel Hydroxyapatite Surface for Biomedical Applications-In Vitro Study," Trends in Biomaterials & Artificial Organs, vol. 16, No. 1, pp. 18-20, (2002).

Balas et al., "Formation of Bone-Like Apatite on Organic Polymers Treated with a Silane-Coupling Agent and a Titania Solution," Biomaterials, vol. 27, pp. 1704-1710, (2006).

Balaur et al., "Tailoring the wettability of TiO2 nanotube layers," Electrochemistry Communications, vol. 7, pp. 1066-1070, (2005).

Banks et al., "Femtosecond Laser-Induced Forward Transfer (LIFT): A Technique for Versatile Micro-Printing Applications," European Conference on Lasers and Electro-Optics and the International Quantum Electronics Conference, 1 page, Jun. 17-22, 2007.

Banks et al., "Nano-droplets Deposited in Microarrays by Femtosecond Ti: Saphire Laser-Induced Forward Transfer," Optoelectronics Reaserch Centre, University of Southhampton, Applied Physics Letters, vol. 89, Issue 19, pp. 1-12, (2006).

Barbucci et al, Micro and nano-structured surfaces,: Journal Of Materials Science: Materials In Medicine, vol. 14, No. 8, pp. 721-725, (2003).

Bates et al. "Description of research activites: Block copolymers," Organization for Minnesota Nanotechnology Institute, University of Minnesota, pp. 1-2, (2002).

Bayoumi et al., "Formation of self-organized titania nano-tubes by dealloying and anodic oxidation," Electrochemistry Communications, vol. 8, pp. 38-44, (2006).

Békési et al., "Efficient Submicron Processing of Metals with Femtosecond UV Pulses," Applied Physics A, vol. 76, pp. 355-357 (2003).

Benson, "Drug Delivery Technology and Access," Polygenetics, Inc., pp. 1-10, Oct. 2005.

Benson, "Highly Porous Polymers," American Laboratory, pp. 1-14, Apr. 2003.

Berg et al., "Controlled Drug Release from Porous Polyelectrolyte Multilayers," Biomacromolecules, vol. 7, pp. 357-364, (2006).

Berkland et al., "Controlling surface nano-structure using flow-limited field-injection electrostatic spraying (FFESS) of poly(D,L-lactide-co-glycolide)," Biomaterials, vol. 25, pp. 5649-5658, (2004).

Berry et al., "The fibroblast response to tubes exhibiting internal nanotopography," Biomaterials, vol. 26, No. 24, pp. 4985-4992, (2005).

Biederman et al. "Plasma Polymer-Metal Composite Films," Plasma Deposition, Treatment and Etching of Polymers, pp. 269-320, (1990).

Bock et al., "Anion and water involvement in hydrous Ir oxide redox reactions in acidic solutions," Journal of Electroanalytical Chemistry, vol. 475, pp. 20-27, (1999).

Bolle et al., "Characterization of submicrometer periodic structures produced on polymer surfaces with low-fluence ultraviolet laser radiation," Journal of Applied Physics, vol. 73, No. 7, pp. 3516-3524, Apr. 1, 1993.

Bolzán et al., "The Potentiodynamic behaviour of iridium electrodes in aqueous 3.7 M H2SO4 in the 293-195 K Range," Journal of Electroanalytical Chemistry, vol. 461, pp. 40-51, (1999).

Boulmedais et la., "Controlled Electrodissolution of Polyelectrolyte Multilayers: A Platform Technology Towards the Surface-Initiated Delivery of Drugs," Advanced Functional Materials, vol. 63, pp. 63-70, (2006).

Boura et al., "Endothelial cell—interactions with polyelectrolyte multilayer films," Biomaterials, vol. 26. pages 4568-4575, (2005).

Bradley et al., "Visuotopic Mapping Through a Multichannel Stimulating Implant in Primate V1," Journal of Neurophysiology, vol. 93, pp. 1659-1670, (2005).

Bretagnol et al., "Functional Micropatterning Surface by Combination of Plasma Polymerization and Lift-Off Process," Plasma Process and Polymers, vol. 3, pp. 30-38, Nov. 14, 2005.

Bretagnol et al., "Surface Functionalization and Patterning Techniques to Design Interfaces for Biomedical and Biosensor Applications," Plasma Processes and Polymers, vol. 3, pp. 443-455, (2006).

Brody et al., "Characterization Nanoscale topography of the Aortic Heart Valve Basement Membrane for Tissue Engineering Heart Valve Scaffold Design," Tissue Engineering, vol. 12, No. 2, pp. 413-421, Nov. 2, 2006.

Bruckner et al., "Metal plasma immersion ion implantation and deposition (MPIIID): chromium on magnesium," Surface and Coatings Technology vol. 103-104, pp. 227-230, (1998).

Brunetti et al., "Oxide/hydroxide films on tin. Part I: Kinetic aspects of the electroformation and electroreductions of the films," Journal of Electroanalytical Chemisty, pp. 1-7, (2007).

Bu et al., "Preparation of nanocrystalline TiO2 porour films from terpineol-ethanol-PEG system," Journal of Materials Science, vol. 41, pp. 2067-2073, (2006).

Bu et al., "Synthesis of TiO2 Porous Thin Films by Polythylene Glycol Templating and Chemistry of the Process," Journal of the European Ceramic Society, vol. 25, pp. 673-679 (2005).

Burmeister et al., "Colloid Monolayers as Versatile Lithographic Masks," Langmuir, vol. 13, pp. 2983-2987, (1997).

Buster et al., "Crystal habits of the Magnesium Hydroxide mineral Brucite within Coral Skeletons," American Geophysical Union Annual Meeting, Abstract and Poster, pp. 1-3, (2006).

Buttiglieri et al., "Endothelization and adherence of leucocytes to nanostructured surfaces," Biomaterials, vol. 24, pp. 2731-2738, (2003).

Calcagno et al., "Structural modification of polymer films by ion irradiation," Nuclear Instruments and Methods in Physics Research, vol. B65, pp. 413-422, (1992).

Carp et al., "Photoinduced Reactivity of Titanium Dioxide," Progress in Solid State Chemistry, vol. 32, pp. 33-177, (2004).

Caruso, "Nanoscale Particle Modifications via Sequential Electrostatic Assembly," Colloids and Colloid Assemblies: Synthesis, Modification, Organization and Utilization of Colloid Particles, pp. 266-269, Mar. 19, 2004.

Cassak, "RT: Bucking the Trend in Bioabsorbable Stents", Windhover Information Inc., In Vivo Jun., pp. 1-14, 2008.

Catledge et al, "Structure and Mechanical Properties of Functionally-Graded Nanostructured Metalloceramic Coatings," Mat. Res. Soc. Symp. Proc. vol. 778, ppU7.8.1 -U7.8.6, (2003).

Catledge et al., "Structural and mechanical properties of nanostructured metalloceramic coatings on cobalt chrome alloys," Applied Physics LEtters, vol. 82, No. 10, pp. 1625-1627, Mar. 10, 2003.

Caves et al., "The evolving impact of microfabrication and nanotechnology on stent design," Journal of Vascular Surgery, pp. 1363-1368, Dec. 2006.

Caves et al., "The evolving impact of microfabrication and nanotechnology on stent design," Journal of Vascular Surgury, vol. 44, pp. 1363-1368, (2006).

Cernigoj et al., "Photocatalytically Active TiO2 Thin Films Produced by Surfactant-Assistant Sol-Gel Processing," Thin Solid Films, vol. 495, pp. 327-332, (2006).

Ceruti et al., "Preparation, characterization, cytotoxicity and pharmacokinetics of liposomes containing water-soluble prodrugs of paclitaxel," Journal of Controlled Release, vol. 63, pp. 141-153, (2000).

Champagne et al., "Nanometer-scale scanning sensors fabricated using stencil lithography," Applied Physics Letters, vol. 82, No. 7, pp. 1111-1113, Feb. 17, 2003.

Chandra et al., "Biodegradable Polymers," Progress in Polymer Science, vol. 23, pp. 1273-1335, (1998).

Chang et al., "Preparation and Characterization of Nanostructured Tin Oxide Films by Electrochemical Deposition," Electrochemical and Solid-State Letters, vol. 5, No. 8, pp. C71-C74, (2002).

Chen et al., "Blood compatiblity and sp3/sp2 contents of diamond-like carbon (DLC) synthesized by plasma immersion ion implantation-deposition," Surface and Coatings Technology, vol. 156, pp. 289-294, (2002).

Chen et al., "Fabrication of micro-field emitters on ceramic substrates," Microelectronic Engineering, vol. 84, pp. 94-100, (2007).

Chen et al., "Behavior of Cultured Human Umbilical Vein Endothelial Cells on Titanium Oxie Films Fabricated by Plasma Immersion Ion Implantation and Deposition," Surface & Coatings Technology, vol. 186, pp. 270-276, (2004).

Cheng et al., "Anatase Coating on NiTi Via a Low-Temperature Sol-Gel Route for Improving Corrosion Resistance," Scripta Materialia, vol. 51, pp. 1041-1045, (2004).

Cho et al., "A Novel Route to Three-Dimensionally Ordered Macroporous Polymers by Electron Irradiation of Polymer Colloids" Advanced Materials, vol. 17, No. 1, pp. 120-125, Jan. 6, 2005.

Cho et al., "Influence of Silica on Shape Memory Effect and Mechanical Properties of Polyurethane-Silica Hybrid," European Polymer Journal, vol. 40, pp. 1343-1348, (2004).

Cho et al., "Preparation and Characterization of Iridium Oxide Thin Films Grown by DC Reactive Sputtering," Japanese Journal of Applied Physics, vol. 36, Part 1, No. 3B, pp. 1722-1727, Mar. 1997.

Choi et al., "Synthesis and Characterization of Diamond-Like Carbon Protective AR Coating," Journal of the Korean Physical Society, vol. 45, p. S864, Dec. 2004.

Chougnet et al., "Substrates do influence the ordering of mesoporous thin films," Journal of Materials Chemistry, vol. 15, pp. 3340-3345, (2005).

Chougnet et al., "The Influence of the Nature of the Substrate on the Ordering of Mesoporous Thin Films," Thin Solid Films, vol. 495, pp. 40-44, (2006).

Chow et al., "Nanostructured Films and Coating by Evaporation, Sputtering, Thermal Spraying, Electro and Electroless Deposition," Handbook of Nanophase and Nanostructured Materials, vol. 1, Chapter 9, pp. 246-272, (2003).

Chow et al., "Preliminary Evaluation of Kem for Fabrication," Proceedings of the 12th General Meeting of Jowog 31, Livermore, CA, University of California, pp. 1-7, (1996).

Chronakis, "Novel nanocomposites and nanoceramics based on polymer nanofibers using electrospinning process—A review," Journal of Materials Processing Technology, vol. 167, pp. 283-293, (2005).

Chu, "Recent developments and applications of plasma immersion ion implantation," Journal of Vacuum Science Technology, vol. B22, No. 1, pp. 289-296, Jan./Feb. 2004.

Chuang et al., "Titanium Oxide and Polyaniline Core-Shell Nanocomposites," Synthetic Metals, vol. 152, pp. 361-364, (2005).

Chung et al., "Roles of discontinuities in bio-inspired adhesive pads," Journal of the Rolyal Society: Interface, vol. 2, pp. 55-61, Feb. 8, 2005.

Clark, "Micropatterning Cell Adhesiveness", Immobilized Biomolecules in Analysis, Oxford University Press, pp. 95-111, (1998).

Clevy et al., "Micromanipulation and Micro-Assembly Systems," IEEE/RAS International Advanced Robotics Program, IARP'06, Paris, France, pp. 1-6, (2006).

Colina et al., "DNA deposition through laser induced forward transfer," Biosensors and Bioelectronics, vol. 20, pp. 1638-1642, (2005).

Costanzo et al., "Model-Based Simulations to Engineer Nanoporous Thin Films," LPCM Research, Pennsylvania State University, pp. 1-3, (2004), (http://lpcm.esm.psu.edu/~tjy107/research.htm).

Course: C-103, "An Introduction to Physical Vapor Deposition (PVD) Processes," Society of Vacuum Coaters, SVC Education Programs: course description and syllabus, pp. 1-4, Apr. 19, 2008.

Course: C-208, "Sputter Deposition in Manufacturing" Society of Vacuum Coaters, SVC Education Programs: course description and syllabus, pp. 1-5, Apr. 22, 2008.

Csete et al., "The existence of sub-micrometer micromechanical modulation generated by polarized UV laser illumination on polymer surfaces," Materials Science and Engineering C, vol. 23, pp. 939-944, (2003).

Csete et al., "The role of original surface roughness in laser-induced periodic surface structure formation process on poly-carbonate films," Thin Solid Films, vol. 453-454, pp. 114-120, (2004).

Curtis et al. "Cells react to nanoscale order and symmetry in their surroundings," IEEE Transactions on Nanobioscience, vol. 3, No. 1, pp. 61-65, Mar. 2004.

Curtis et al., "Nantotechniques and approaches in biotechnology," Trends in Biotechnology, vol. 19, No. 3, pp. 97-101, Mar. 2001.

Curtis et al., "New Depths in Cell Behaviour: Reactions of Cells to Nanotopography," Biochem, Soc, Symp, vol. 65, pp. 15-26, (1999).

Curtis et al., "New depths in cell behaviour: Reactions of cells to nanotopography," Biochemical Society Symposium, No. 65, pp. 15-26 (1997).

Curtis et al., "Topographical Controls of Cells," Biomaterials, vol. 18, pp. 1573-1583, (1997).

Curtis, "Tutorial on the biology of nanotopography," IEEE Transactions on Nanobioscience, vol. 3, No. 4, pp. 293-295, Dec. 2004.

Cyster et al., "The effect of surface chemistry and nanotopography of titanium nitride (TiN) films on 3T3-L1 fibroblasts," Journal of Biomedical Materials Research: A., vol. 67, No. 1, pp. 138-147, Oct. 2003.

Cyster et al., "The effect of surface chemistry and nanotopography of titanium nitride (TiN) films on primary hippocampal neurones," Biomaterials, vol. 25, pp. 97-107, (2004).

da Cruz et al., "Preparation, structure and electrochemistry of a polypyrrole hybrid film with [Pd(dmit)2]2-, bis(1,3-dithiole-2-thione-4,5-dithiolate)palladate(II)," Electrochimica Acta, vol. 52, pp. 1899-1909, (2007).

Dalby et al., "In vitro reaction of endothelial cells to polymer demixed nanotopography," Biomaterials, vol. 23, No. 14, pp. 2945-2954, (2002).

Dalby, "Topographically induced direct cell mechanotransduction," Medical Engineering & Physics, vol. 27, No. 9, pp. 730-742, (2005).

Damen et al., "Paclitaxel Esters of Malic Acid as Prodrugs with Improved Water Solubility," Bioorganic & Medicinal Chemistry, vol. 8, pp. 427-432, (2000).

D'Aquino, "Good Drug Therapy: It's Not Just the Molecule—It's the Delivery," CEP Magazine, (www.cepmagazine.org), 3 pages, Feb. 2004.

Datta et al., "Fundamental aspects and applicatio of electrochemical microfabrication," Electrochimica Acta, vol. 45, pp. 2535-2558, (2000).

Daxini et al., "Micropatterned polymer surface inprove retention of endothelial cells exposed to flow-induced shear stress," Biorheology, vol. 43, pp. 45-55, (2006).

De Aza et al., "Crack growth resistance of alumina, zirconia and zirconia toughened alumina ceramics for joint prostheses," Biomaterials, vol. 23, No. 3, pp. 937-945, Feb. 2002.

Deakin et al., "De-alloying of type 316 stainless steel in hot, concentrated sodium hydroxide solution," Corrosion Science, vol. 46, pp. 2117-2133, (2004).

Debiotech, "Debiostar, an Innovative Solution for Sustained Drug Delivery," pp. 1-4, Copyright 2001, (http://www.debiotech.com/products/drugdd/stent_page_1.html).

Debiotech, "Debiostent: An Innovatice Ceramic Coating for Implantable Medical Devices," pp. 12, [first downloaded on Sep. 1, 2005], (http://www.debiotech.com/products/drugdd/stent_page 1.html).

Debiotech, "Debiostent: Polymer free drug eluting coating," Jun. 14, 2007, pp. 1-2, (www.debiotech.com/products/dmggd/stent_page_1.html).

Debiotech, "Debiotech Obtains Exclusive Rights to an Innovative Drug Eluting Stent Technology," Press release, 1 page, Mar. 7, 2003.

Demisse, "Computational Investigation of Conducting Polythiophenes and Substituted Polythiophenes," A Thesis Submitted to the School of Graduate Studies of Addis Ababa University, Ethiopia, pp. 1-86, Jun. 2007.

Deniau et al., "Study of the polymers obtained by electroreduction of methacrylonitrile," Journal of Electroanalytical Chemistry, vol. 505, pp. 33-43, (2001).

Desai et al., "Characterization of micromachined silicon membranes for immunoisolation and bioseparation applications," Journal of Membrane Science, vol. 159, pp. 221-231, (1999).

Desai et al., "Use of Microfabricated 'Nanopore' Membranes as a Rate-Limiting Barrier to Diffusion of Small and Large Molecules: Possible Role in Drug Delivery" BioMEMs and Nanotechnology World, pp. 1-2, (2001).

Desai, Integrating Cells with Microsystems: Application in Tissue Engineering and Cell-Based Delivery, PowerPoint presentation, pp. 1-41, May 10, 2002.

Di Mario et al., "Drug-eluting bioabsorbable magnesium stent," Journal of Interventional Cardiology, vol. 17, Issue 6, pp. 1-5, Dec. 2004.

Di Mario et al., "Moonlight: A controlled registry of an iridium oxide-coated stent with angographic follow-up," International Journal of Cardiology, vol. 95, pp. 329-331, (2004).

Di Mario, The Moonlight Study: Multicenter Objective Observational Lunar Iridium Oxide Intimal Growth Trial, PowerPoint presentation, pp. 1-10, (2002).

Dibra et al., "Influence of the stent surface topology on the outcomes of patients undergoing coronary stenting: A randomized double-blind controlled trial", Catheterization and Cardiovascular Interventions, vol. 65, pp. 374-380, (2005).

Dittmar et al., "Nanostructured Smart Drug Delivery Coatings," European Cells and Materials, vol. 31, Supplement 2, p. 73, (2007).

Dong et al., "Preparation of Submicron Polypyrrole/Poly(methly methacrylate) Coaxial Fibers and conversion to Polypyrrole Tubes and Carbon Tubes," Langmuir, vol. 22, pp. 11384-11387, (2006).

Doraiswamy et al., "Excimer laser forward transfer of mammalian cells using a novel triazene absorbing layer," Applied Surface Science, vol. 252, pp. 4743-4747, (2006).

DTI Technology Group: Materials-Coating, "Kinetic spray coating method," www.delphi.com, 1 page, Jul. 2004.

Dumas et al., "Characterization of magnesium fluoride thin films produced by argon ion beam-assisted deposition," Thin Solid Films, vol. 382, pp. 61-68, (2001).

Duncan et al., "Polymer-drug conjugates, PDEPT and PELT: basic principals for design and transfer from laboratory to clinic," Journal of Controlled Release, vol. 74, pp. 135-146, (2001).

Duncan, "The Dawning Era of Polymer Therapeutics," Nature Reviews: Drug Discovery, vol. 2, pp. 347-360, May 2003.

Dutta et al., "Self-Organization of Colloidal Nanoparticles," Encyclopedia of Nanoscience and Nanotechnology, vol. 9, pp. 617-640, (2003).

Duwez et al., "Mechanochemistry: targeted delivery of single molecules," Nature Nanotechnology, vol. 1, pp. 122-125, (2006).

EAG Technical Note, "Functional Sites on Non-polymeric Materials: Gas Plasma Treatment and Surface Analysis," Evans Analytical Group, pp. 1-2, (2003).

Eberli et al., "The Lunar Coronary Stent System," Handbook of coronary stents, 4th edition, Chapter 17, 11 pages, (Martin Dunitz Ltd 2002).

Eesley et al., "Thermal properties of kinetics spray Al-SiC metal-matrix composite," Journal of Materials Research, vol. 18, No. 4, pp. 855-860, Apr. 2003.

Egerhazi et al., "Thickness distribution of carbon nitride films grown by inverse-pulsed laster deposition," Applied Surface Science, vol. 247, pp. 182-187, (2005).

Electropolymerization, (http://intel.ucc.ie/sensors/Electropolym.htm), pp. 1-2, (downloaded [2007]).

Erlebacher et al., "Evolution of nonoporosity in dealloying," Nature, vol. 410, pp. 450-453, Mar. 22, 2001.

Esrom et al., "New approach of a laser-induced forward transfer for deposition of patterned thin metal films," Applied Surface Science, vol. 86, pp. 202-207, (1995).

Faupel et al., "Microstructure of pulsed laser deposited ceramic-metal and polymer-metal nanocomposite thin films," Applied Physics A, vol. 79, pp. 1233-1235 (2004).

Faust et al., "Biofunctionalised Biocompatible Titania Coatings for Implants," Euro Ceramics VIII, Key Engineering Materials, vol. 206, No. 2, pp. 1547-1550, (2006).

Fernandez-Pradas et al., "Laser-induced forward transfer of biomolecules," Thin Solid Films, vol. 453-454, pp. 27-30, (2004).

Ferraz et al., "Influence of nanoporesize on platelet adhesion and activation," Journal of Materials Science: Materials in Medicine, vol. 19, pp. 3115-3121, (2008).

Figallo et al., "Micropatterned Biopolymer 3D Scaffold for Static and Dynamic Culture of Human Fibroblasts," Biotechnology Progress, vol. 23, pp. 210-216, (2007).

Flemming et al., "Effects of synthetic micro- and nano-structured surfaces on cell behavior," Biomaterials, vol. 20, No. 6, pp. 573-588, (1999).

Fogarassy et al., "Laser-induced forward transfer: A new approach for the deposition of high Tc superconducting thin films," Journal of Materials Research, vol. 4, No. 5, pp. 1082-1086, Sep./Oct. 1989.

Fonseca et al., "Paclitaxel-loaded PLGA nanoparticles: preparation, physicochemical characterization and in vitro anti-tumoral activity," Journal of Controlled Release, vol. 83 pp. 273-286, (2002).

Forty, "Corrosion micromorphology of noble metal alloys and depletion gilding," Nature, vol. 282, pp. 597-598, Dec. 6, 1979.

Frechet, "Functional Polymers: from Plastic Electronics to Polymer-Assisted Therapeutics," Progress in Polymer Science, vol. 30, pp. 844-857, (2005).

Free Online Dictionary, "Aperture," definition, [first viewed Oct. 9, 2009].

Freitas et al., "Nimesulide PLA microsphere as a potential sustained release system for the treatment of inflammatory diseases," International Journal of Pharmaceutics, Vo. 295, pp. 201-211, (2005).

Freitas, "Nanomedicine, vol. I: Basic Capabilities," Landes Bioscience, pp. 87, 90, 255 and 265, (1999).

Friedrich et al., "Developing Interdisciplinary Undergraduate and Graduate Courses Through the Integration of Recent Research Results into the Curricula," (http://www.ineer.org/Events/ICEE1997/Proceedings/paper326.htm), 10 pages, [first downloaded Mar. 10, 2005.].

Fu et al., "Effects of mesh-assisted carbon plasma immersion ion implantation on the surface propoerties of insulating silicon carbide ceramics," Journal of Vacuum Science Technology, vol. A22, No. 2, pp. 356-360, Mar./Apr. 2004.

Fu et al., "Influence of thickness and dielectric properties on implantation efficacy in plasma immersion ion implantation of insulators," Journal of Applied Physics, vol. 95, No. 7, pp. 3319-3323, Apr. 1, 2004.

Fujisawa et al., "A novel textured surface for blood-contact," Biomaterials, vol. 20, pp. 955-962, (1999).

Fulton, "Ion-Assisted Filtered Cathodic Arc Deposition (IFCAD) System for Volume. Production of Thin-Film Coatings," Society of Vacuum Coaters, 42nd Annual Technical Conference Proceedings, (1999).

Gabel et al., "Solid-State Spray Forming of Aluminum Near-Net Shapes," Journal of Metals, vol. 49, No. 8, pp. 31-33, (1997).

Gabel, "Low Temperature Metal Coating Method," Lawrence Livermore National Laboratory, p. 1-4, Apr. 3, 2000.

Gadegaard et al., "Tubes with Controllable Internal Nanotopography," Advanced Materials, vol. 16, No. 20, pp. 1857-1860, Oct. 18, 2004.

Galinski et al., "Ionic liquids as electrolytes," Electrochimica Acta, vol. 51, 5567-5580, (2006).

Gao, "Chemical Vapor Deposition," Handbook of Nanophase and Nanostructured Materials, vol. 1: Synthesis, Chapter 5, (2003).

Geretovszky et al., "Correlation of compositional and structural changes during pulsed laser deposition of tantalum oxide films," Thin Solid Films, vol. 453-454, pp. 245-250, (2004).

Gillanders et al., "A Composite Sol-Gel/Fluoropolymer Matrix for Dissolved Oxygen Optical Sensing," Journal of Photochemistry and Photobiology a: Chemistry, vol. 163, pp. 193-199, (2004).

Glocker et al., "AC Reactive Sputtering with Inverted Cylindrical Magnetrons," Society of Vacuum Coaters, 43rd Annual Technical Conference Proceedings—Denver, pp. 81-85, Apr. 15-20, 2000.

Glocker et al., "Recent developments in inverted cylindrical magnetron sputtering," PowerPoint presentation, pp. 1-21, (2001).

Glocker et al., "Recent developments in inverted cylindrical magnetron sputtering," Surface and Coatings Technology, vol. 146-147, pp. 457-462, (2001).

Goddard et al., "Polymer surface modification for the attachmend of bioactive compounds," Progress in Polymer Science, vol. 32, pp. 698-725, (2007).

Goh et al., "Nanostructuring Titania by Embossing with Polymer Molds Made from Anodic Alumina Templates," Nano Letters, vol. 5, No. 8, pp. 1545-1559, (2005).

Gollwitzer et al., "Titania Coating as Local "Drug" Delivery System with Antibacterial and Biocompatible Properties," 1 page, (2003).

Gong et al., "Controlled molecular release using nanopourous alumina capsules," Biomedical Microdevices, vol. 5, No. 1, pp. 75-80, Mar. 2003.

Gong et al., "Titanium oxide nanotube arrays prepared by anodic oxidation," Journal of Material Research, vol. 16, No. 12, pp. 3331-3334, (2001).

Goodison et al., "CD44 cell adhesion molecules," Journal of Clinical Pathology: Molecular Pathology, vol. 52, pp. 189-196, (1999).

Goodman et al., "Three-dimensional extracellular matrix textured biomaterials," Biomaterials, vol. 17, pp. 2087-295, (1996).

Gorb et al., "Biological microtribology: anisotropy in frictional forces of orthopteran attachment pads reflects the unitrastructure of a highly deformable material," Proceeding of the Royal Society, London series B, vol. 267, pp. 1239-1244, (2000).

Gotszalk et al., "Diagnostics of micro- and nanostructure using the scanning probe microscopy," Journal of Telecommunications and Information Technology, pp. 41-46, (2005).

Granqvist et al., "Biodegradable and bioactive hybrid organic-inorganic Peg-siloxane fibers: Preparation and Characterization," Colloid Polymer Science, vol. 282, pp. 495-501, (2004).

Greeley et al., "Electrochemical dissolution of surface alloys in acids: Thermodynamic trends from first-principles calculations," Electrochimica Acta, ol. 52, pp. 5829-5836, (2007).

Green et al., "XPS Characterisation of Surface Modified Ni-Ti Shape Memory Alloy," Materials Science and Engineering, vol. A224, pp. 21-26, (1997).

Gressel-Michel et al., "From a Microwave Flash-Synthesized TiO2 Colloidal Suspension to TiO2 Thin Films," Journal of Colloid and Interface Science, vol. 285, pp. 674-679, (2005).

Groth et al., "Layer-by-Layer Deposition of Polyelectrolytes—A Versatile Tool for the in Vivo Repair of Blood Vessels," Angewandte Chemie, International Edition, vol. 43, pp. 926-928, (2004).

Grubmuller, "What happens if the Room at the Bottom Runs Out? A Close Look at Small Water Pores," PNAS, Vol. 100, No. 13, pp. 7421-7422, Jun. 24, 2003.

Gu et al., "Biomimetic titanium dioxide film with structural color and extremely stable hydrophilicity," Applied Physics Letters, vol. 85, No. 21, pp. 5067-5069 (2004).

Guangliang et al., "The effects of current density on the phase composition and microstructure properties of micro-arc oxidation coating," Journal of Alloys and Compounds, vol. 345, pp. 169200, (2002).

Guo et al., "Formation of oxygen bubbles and its influence on current efficiency in micro-arc oxidation process of AZ91D magnesium alloy," Thin Solid Films, vol. 485, pp. 53-58, (2005).

Guo et al., "Growth of ceramic coatings on AZ91D magnesium alloys by micro-arc oxidation in aluminate-fluoride solutions and evalucation of corrosion resistance," Applied Surface Science, Col. 246, pp. 229-238, (2005).

Guo et al., "Investigation of corrosion behaviors of Mg-6Gd-3Y-0.4Zr alloy in NaC1 aqueous solutions," Electrochimica Acta, vol. 52, pp. 2570-2579, (2007).

Guo et al., "Sol gel derived photocatalytic porous TiO2 thin films," Surface & Coatings Technology, vol. 198, pp. 24-29, (2005).

GVD Corporation, "Nanocoatings for a New Era," pp. 1-3, [first downloaded Nov. 12, 2003].

Haag et al., "Polymer Therapeutics: Concepts and Applications," Angewandte Chemie, vol. 45, pp. 1198-1215, (2006).

Haberland et al., "Filling of micron-sized contact holes with copper by energetic cluster impact," Journal of Vacuum Science Technology A, vol. 12, No. 5, pp. 2925-2930, Sep./Oct. 1994.

Haery et al., "Drug-eluting stents: the beginning of the end of restenosis?," Cleveland Clinic Journal of Medicine, vol. 71, No. 10, pp. 815-824, (2004).

Hahn et al., "A novel approach for the formation of Mg(OH)2/MgO nanowhiskers on magnesium: Rapid anodization in chloride containing solutions", Electrochemistry Communications, vol. 10, pp. 288-292, (2008).

Halme et al., "Spray Deposition and Compression of TiO2 Nanoparticle Films for Dye-Sensitized Solar Cells on Plastic Substrates," Solar Energy Materials & Solar Cells, vol. 90, pp. 887-899, (2006).

Hamley et al., "Nanostructure fabrication using block copolymers," Nanotechnology, vol. 14, pp. R39-R54, (2003).

Han et al., "Electron injection enhancement by diamond-like carbon film in organic electroluminescence devices," Thin Solid Films, vol. 420-421, pp. 190-194, (2002).

Han et al., "Pourous nanocrystalline titania films by plasma electrolytic oxidation," Surface and Coatings Technology, vol. 154, pp. 314-318, (2002).

Han et al., "Structure and in vitro bioactivity of titania-based films by micro-arc oxidation," Surface and Coatings Technology, vol. 168, pp. 249-258, (2003).

Han et al., "Synthesis of nanocrystalline titaniaa films by micro-arc oxidation," Materials Letters, vol. 56, pp. 744-747, (2002).

Hanley et al., "The growth and modification of materials via ion-surface processing," Surface Science, vol. 500, pp. 500-522, (2002).

Harris et al., "Fabrication of Perforated Thin Films with Helical and Chevron Pore Shapes," Electrochemical and Solid-State Letters, vol. 4, pp. C39-C42, (2004).

Harvard Nanopore, "Ion Beam Sculpting: Material Science—Fabricating Nanopores and Other Nanoscale Feature," pp. 1-5, [first downloaded Jul. 2, 2003], (http://www.mcb.harvard.edu.branton/projects-IonBeam/htm).

Hattori et al., "Photoreactivity of Sol-Gel TiO2 Films Formed on Soda-Lime Glass Substrates: Effect of SiO2 Underlayer Containing Fluorine," Langmuir, vol. 15, pp. 5422-5425, (1999).

Hau et al., "Surface-chemistry technology for microfluidics," Journal of Micromechanics and Microengineering, vol. 13, pp. 272-278, (2003).

Hausleiter et al., "Prvention of restenosis by a novel drug-eluting stent system with a dose-adjustable, polymer-free, on-site stent coating," European Heart Journal, vol. 26, pp. 1475-1481, (2005).

He et al., "Electrochemical Fabrication of Metal Nanowires," Encyclopedia of Nanoscience and Nanotechnology, vol. X, pp. 1-18, (2003).

He et al., "Optical properties of diamond-like carbon synthesized by plasma immersion ion processing," Journal of Vacuum Science Technology, vol. B17, No. 2, pp. 822-827, Mar./Apr. 1999.

Heidenau et al., "Structured Porous Titania as a Coating for Implant Materials," Key Eng Mater. vol. 192-195, pp. 87-90, (2001).

Heinig et al., "Modeling and Simulation of Ion Beam Systhesis of Nanoclusters," 6 pages, [first downloaded Jan. 3, 2000], (http://www.fz-rossendorf.de/pls/rois/Cms?pOId=10960&pFunc=Print&pLang=de).

Helmersson et al., "Ionized physical vapor deposition (IPVD): A review of technology and applications," Thin Solid Films, vol. 513, pp. 1-24, (2006).

Helmus et al. "Surface Analysis of a Series of Copolymers of L-Glutamic Acid and L-Leucine," Journal of Colloid and Interface Science, vol. 89, No. 2, pp. 567-570, (1982).

Helmus et al., "Plasma Interaction on Block Copolymers as Determined by Platelet Adhesion," Biomaterials: Interfacial Phenomena and Applications: Chapter 7, pp. 80-93, (1981).

Helmus et al., "The Effect of Surface Charge on Arterial Thrombosis," Journal of Biomedical Materials Research, vol. 18, pp. 165-183, (1984).

Hentze et al., "Porous polymers and resins for biotechnological and biomedical applications," Reviews in Molecular Biology, vol. 90, pp. 27-53, (2002).

Hoa et al., "Preparation of porous meterials with ordered hole structure," Advances in Colloid and Interface Science, vol. 121, pp. 9-23, (2006).

Hoffman, "Non-Fouling Surface Technologies," Journal of Biomaterials Science, Polymer Edition, vol. 10, No. 10, pp. 1011-1014, (1999).

Hoglund, "Controllable Degradation Product Migration From Biomedical Polyester-ethers," KTH Chemical Science and Engineering, Stockholm, pp. 1-52, May 24, 2007.

Holland et al., "Synthesis of Macroporous Minerals with Highly Ordered Three-Dimensional Arrays of Spheroidal Voids," Science, vol. 281, pp. 538-540, Jul. 24, 1998.

Hong et al., "The super-hydrophilicities of Bi-TiO2, V-TiO2, and Bi-V-TiO2 nano-sized particles and their benzene photodecompositions with H2O addition," Materials Letters, vol. 60, pp. 1296-1305, (2006).

Hopp et al., "Absorbing film assisted laser induced forward transfer of fungi (*Trichoderma conidia*)," Journal of Applied Physics, vol. 96, No. 6, pp. 3478-3481, Sep. 15, 2004.

Houbertz, "Laser interaction in sol-gel based materials—3-D lithography for photonic applications," Applied Surface Science, vol. 247, pp. 504-512, (2005).

Houdayer et al., "Preparation of new antimony(0)/polyaniline nanocomposites by a one-pot solution phase method," Materials Letter, vol. 61, pp. 171-176, (2007).

Hrudey et al., "Organic Alq3 Nanostructures Fabricated with Glancing Angle Depostion," Vacuum Technology & Coating, pp. 1-6, May 2006.

Hsiao et al., "Soluble aromatic polyamides bearing asymmetrical diaryl ether groups," Polymer, vol. 45, pp. 7877-7885, (2004).

Hu et al., "Cyclic voltammetric deposition of hydrous ruthenium oxide for electrochemical capacitors: effects of codeposting iridium oxide," Electrochimica Acta, vol. 45, pp. 2684-2696, (2000).

Hu et al., "Voltammetric investigation of platinum oxides II. Efect of hydration on the reduction behavior," Electrochimica Acta, vol. 45, pp. 3063-3068, (2000).

Hüppauff et al., "Valency and Structure of Iridium in Anodic Iridium Oxide Films," Journal of Electrochemical Society, vol. 140, No. 3, pp. 598-602, Mar. 1993.

Hurley et al., "Nanopatterning of Alkynes on Hydrogen-Terminated Silicon Surfaces by Scanning Probe-Induced Cathodic Eletrografting," Journal of American Chemistry Society, vol. 125, pp. 11334-11339, (2003).

Hussain et al., "Atomic force microscope study of three-dimensional nanostructure sidewalls," Nanotechnology, vol. 18, pp. 1-8, (2007).

Ichinose et al., "A surface sol-gel process of TiO2 and other metal oxide films with molecular precision," Chem. Mater. vol. 9, pp. 1296-1298, (1997).

Ichinose et al., "Ultrathin composite films: an indispensable resource for nanotechnolo ," Riken Review, No. 37, pp. 34-37, Jul. 2001.

Ignatova et al., "Combination of Electrografting and Aton-Transfer Radical Polymerization for Making the Stainless Steel Surface Antibacterial and Protein Antiadhesive," Langmuir, vol. 22, pp. 255-262, (2006).

Imai et al., "Preparation of Porous Anatase Coatings from Sol-Gel-Derived Titanium Dioxide and Titanium Dioxide-Silica by Water-Vapor Exposure," Journal of American Ceramics Society, vol. 82, No. 9, pp. 2301-2304, (1999).

Inflow Dynamics starts "LUSTY" Study, Company Press Release: First clinical trial with Niobium stents, (www.tctmd.com/industry-news/one.html?news_id=3364), 1 page, Jun. 25, 2002.

Inoue et al., "Corrosion rate of magnesium and its alloys in buffered chloride solutions," Corrosion Science, vol. 44, pp. 603-610, (2002).

Inovati, "Award Winning—Environmentally-Safe, High-Quality, Metal Spray Process," Press Release, pp. 1-6, (2002), (http://www.inovati.com/papers/KM-PressRelease.doc).

Inovati, "Inovati to Develop Green Metal Coating Technology" Press Release, 1 page, [first downloaded Sep. 1, 2005], (http://www.inovati.com/papers/bmdopr.html).

Inovati, "Low temperature, high-speed sprays make novel coatings," 1 page, [first downloaded on Mar. 18, 2003], (http://www.inovati.com/papers/ampmar01.html).

Introduction to the Metal Printing Process: Future manufacturing equipment of advanced materials and complex geometrical shapes, (www.mpp.no/intro/intro.htm), pp. 1-2, downloaded Mar. 18, 2002.

Irhayem et al., "Glucose Detection Based on Electrochemically Formed Ir Oxide Films," Journal of Electroanalytical Chemistry, vol. 538-539, pp. 153-164, (2002).

Irvine et al., Nanoscale clustering of Rgd peptides at surfaces using Comb polymers. 1. Synthesis and characterization of Comb thin films, Biomacromolecules, vol. 2, No. 1, pp. 85-94, Spring 2001.

Irvine et al., "Nanoscale clustering of RGD peptides at surfaces using comb polymers. 2. Surface segregation of comb polymers in polylactide," Biomacromolecules, vol. 2, No. 2, pp. 545-556, Summer 2001.

Ishizawa et al., "Characterization of thin hydroxyapatite layers formed on anodic titanium oxide films containing Ca and P by hydrothermal treatment," Journal of Biomedical Materials Research, vol. 29, pp. 1071-1079, (1995).

Ishizawa et al., "Histomorphometric evaluaction of the thin hydroxyapatite layer formed through anodization followed by hydrothermal treatment," Journal of Biomedical Materials Research, vol. 35, pp. 199-206, (1997).

Isoflux Inc., "Isoflux specializes in vacuum coating equipment and coating process," http://www.isofluxinc.com/about.shtml, 1 page, Jul. 2009.

Iurhayem et al. "Glucose detection based on electrochemically formed Ir oxide films," Journal of Electroanalytical Chemistry, vol. 539-539, pp. 153-164, (2002).

Jensen et al., "Low-temperature preparation of nanocrystalline anatase films through a sol-gel rout," Journal of Sol-Gel Science and Technology, vol. 39, pp. 229-233, (2006).

Jewell et al., "Multilayered polyelectolyte films promote the direct and localized delivery of Dna to cells," Journal of Controlled Release, vol. 106, pp. 214-223, (2005).

JMAR LLLC, "Collimated Plasma Lithography (CPL)," 1 page, [first downloaded Jul. 2, 2003], (http://www.jmar.com/co451.html).

Johnson, "What's an Ionic Liquid?," The Electrochemical Society: Interface, pp. 38-41, Spring 2007.

Juodkazis et al., "Alternative view of anodic surface oxidation of nobel metals," Electrochimica Acta, vol. 51, pp. 6159-6164, (2006).

Kamei et al., "Hydrophobic drawings on hydrophilic surfaces of single crystalline titanium dioxide: surface wettability control by mechanochemical treatment," Surface Science Letters, vol. 463 pp. L609-L612, (2000).

Kanda et al., "Characterization of Hard Diamond-Like Carbon Films Formed by Ar Gas Cluster Ion Beam-Assisted Fullerene Deposition," Japanese Journal of Applied Physics, vol. 41, Part 1, No. 6B, pp. 4295-4298, Jun. 2002.

Kang et al., "Controlled drug release using nanoporous anodic aluminum oxide on stent," Thin Solid Films, vol. 515, pp. 5184-5187, (2007).

Kaplan, "Cold Gass Plasma and Silanes," Presented at the 4th International Symposium on Silanes and Other Coupling Agents, Jul. 11-13, 2003.

Karuppuchamy et al., "Cathodic Electrodeposition of Oxide Semiconductor Thin Films and their Application to Dye-Sensitized Solar Cells," Solid State Ionics, vol. 151, pp. 19-27, (2002).

Karuppuchamy et al., "Photoinduced Hydrophilicity of Titanium Dioxide Thin Films Prepared by Cathodic Electrode position," Vacuum, vol. 80, pp. 494-498, (2006).

Karuppuchamy et al., "Super-hydrophilic amorphous titanium dioxide thin film deposited by cathodic electrodeposition," Materials Chemisty and Physics, vol. 93, pp. 251-254, (2005).

Karuri et al., "Biological length scale topography enhances cell-substratum adhesion of human corneal epithelial cells," Journal of Cell Science, vol. 117, No. 15, pp. 3153-3164, (2004).

Kasemo et al., "Implant surfaces and interface processes," Adv. Dent. Res. vol. 13, pp. 8-20 Jun. 1999.

Kasemo, "Biological surface science," Surface Science, vol. 500, pp. 656-677, (2002).

Kato et al., "N-succinyl-chitosan as a drug carrier: water-insoluble and water-soluble conjugates," Biomaterials, vol. 25, pp. 907-915, (2004).

Katsumata et at., "Effect of Microstructure on Photoinduced Hydrophilicity of Transparent Anatase Thin Films," Surface Science, vol. 579, pp. 123-130, (2005).

Katz, "Developments in Medical Polymers for Biomaterials Applications," Medical Device Link, pp. 1-9, Jan. 2001, (http://www.devicelink.com/mddi/archive/01/01/003.html).

Kean et al. "The Analysis of Coatings Produced by Accelerated Nanoparticles," Mantis Deposition Ltd., Presentaction at Nsti Nano Tech 2006, Boston, May 7th-11th, pp. 1-4, 2006.

Kesapragada et al., "Two-component nanopillar arrays grown by Glancing Angle Deposition," Thin Solid Films, vol. 494, pp. 234-239, (2006).

Kesler etal., "Enhanced Strength of Endothelial Attachment on Polyester Elastomer and Polytetrafluoroethylene graft Surfaces with Fibronectin Substrate," Journal of Vascular Surgery, vol. 3, No. 1, pp. 58-64, (1986).

Kesting, "Synthetic Polymeric Membranes—A Structural Perspective", Chapters 6-7, pp. 225-286, Oct. 1985.

Kickelbick, "Concepts for the incorporation of inorganic building blocks into organic polymers on a nanoscale," Progress in Polymer Science, vol. 28, pp. 81-114, (2003).

Kidambi et al., "Selective Depositions on Polyelectrolyte Multilayers: Self-Assembled Monolayers on m-dPEG Acid as Molecular Template," Journal of the American Chemistry Society, vol. 82, No. 9, pp. 4697-4703, (2004).

Kilian et al., "Plasma transglutaminase factor XIII induces microvessel ingrowth into biodegradable hydroxyapatite implants in rats," Biomaterials, vol. 26, pp. 1819-1827, (2005).

Kim et al. "Porous ZrO2 bone scaffold coated with hydroxyapatite with fluorapatite intermediate layer," Biomaterials, vol. 24, pp. 3277-3284, (2003).

Kim et al., "Adhesion of RF bias-sputtered Cr thin films onto photosensitivepolyimide substrates," IEEE, International Symposium on Eelectrical Materials and Pakaging, pp. 202-207, (2001).

Kim et al., "Fabrication of WC-Co coatings by cold spray deposition," Surface & Coatings Technology, vol. 191, pp. 335-340, (2005).

Kim et al., "Hollow Silica Spheres of Controlled Size and Porosity by Sol-Gel Processing," Journal of Americal Ceramic Society, vol. 74, No!. 8, pp. 1987-1992, (1991).

Kim et al., "Proton conducting polydimethylsiloxane/metal oxide hybrid membranes added with phosphotungstic acid(Ii)," Electrochimica Acta, vol. 49, pp. 3429-3433, (2004).

Kim et al., "Fabrication and Characterization of TiO2 Thin Film Prepared by a Layer-By-Layer Self-Assembly Method," Thin Solid Films, vol. 499, pp. 83-89, (2006).

Kitagawa et al., "Near-Edge X-Ray Absorption Fine Structure Study for Optimization of Hard Diamond-Like Carbon Film Formation with Ar Cluster Ion Beam," Japanese Journal of Applied Physics, vol. 42, pp. 3971-3975, (2003).

Kitagawa et al., Optimum Incident Angle of Ar Cluster Ion Beam for Superhard Carbon Film Deposition, Japanese Journal of Applied Physics, vol. 43, No. 6B, pp. 3955-3958, (2004).

Kittaka et al., "The Structure of Water Monolayers on a Hydroxylated Chromium Oxide Surface," Adsorption, vol. 11, pp. 103-107, (2005).

Kleinertz et al., "LUSTY Studie: Lunar STF Study," PowerPoint presentation, pp. 1-24, Sep. 4, 2004.

Kleisner et al., "A system based on metal alkyl species that forms chemically bound organic overlays on hydroxylated planar surfaces," Thin Solid Films, vol. 381, pp. 10-14, (2001).

Kogure et al., "Microstructure of nemalite, fibrous iron-bearing brucite", Mineralogical Journal, vol. 20, No. 3, pp. 127-133, Jul. 1998.

Kohli et al., "Arrays of lipid bilayers and liposomes on patterned polyelectrolyte templates," Journal of Colloid and Interface Science, vol. 301, pp. 461-469, (2006).

Kokubo et al., "Novel bioactive materials with different mechanical properties," Biomaterials, vol. 24, pp. 2161-2175, (2003).

Kommireddy et al., "Layer-by-Layer Assembly of TiO2 Nanoparticles for Stable Hydrophilic Biocompatible Coatings" Journal of Nanoscience and Nanotechnology, vol. 5, pp. 1081-1087, (2005).

Kondyurin et al., "Plasma Immersion ion implantation of polyethylene," Vacuum, vol. 64, pp. 105-111, (2002).

Kong et al., "Polyelectrolyte-functionalized multiwalled carbon nanotubes: preparation, characterization and layer-by-layer self-assembly," Polymer, vol. 46, pp. 2472-2485, (2005).

Konig et al., "Nanoprocessing with nanojoule near-infrared femtosecond laser pulses," Medical Laser Application, vol. 20, pp. 169-184, (2005).

Konishi et al., "Morphology Control of Dy-Ni Alloy Films by Electrochemical Displantation," Electrochemical and Solid-State Letters, vol. 5, No. 12, pp. B37-B39, (2002).

Koo et al., "Co-regulation of cell adhesion by nanoscale RGD organization and mechanical stimulus," Journal of Cellular Science, vol. 115, Part 7, pp. 1423-1433, Apr. 1, 2002.

Kopanski et al., "Scanning Kelvin Force Microscopy For Characterizing Nanostructures in Atmosphere," Characterization and Metrology for Nanoelectronics: 2007 International Conference on Frontiers of Characterization and Metrology. American Institute of Physics Conference Proceedings, vol. 931, pp. 530-534, Septem 26, 2007.

Kostov et al., "Two Dimensional Computer Simulation of Plasma Immersion Ion Implantation," Brazilian Journal of Physics, vol. 34, No. 4B, pp. 1689-1695, Dec. 2004.

Kötz et al., "XPS Studies of Oxygen Evolution on Ruand RuO2 Anodes," Journal of Electrochemical Society: Electrochemical Science and Technology, pp. 825-829, Apr. 1983.

Kowalski et al., "Corrosion protection of steel by bi-layered polypyrrole doped with molybdophosphate and naphthalenedisulfonate anions," Corrosion Science, Vo. 49, pp. 1635-1644, ( 2007).

Kraft et al., "Thin films from fast clusters: golden TiN layers on a room temperature substrate" Surface and Coatings Technology 158-159, pp. 131-135, (2002).

Krumeich et al., "HyFraSurf-Advanced Surface Technology for Superior Electrode Performance," European Cells and Materials, vol. 1, Suppl. 1, p. 43, (2001).

Kumar et al., "Influence of electric field type on the assembly of single walled carbon nanotubes," Chemical Physics Letters, vol. 383, pp. 235-239, (2004).

Kumar et al., "Polyanhydrides: an overview," Advanced Drug Delivery Reviews, vol. 54, pp. 889-910, (2002).

Kunitake et al., "Molecular imprinting in ultrathin titania gel films via surface sol-gel process," Analytica Chimica Acta, vol. 504, pp. 1-6, (2004).

Kurth et al., "Multilayers on Solid Planar Substrates: From Structure to Function," Multilayer Thin Films: Sequential Assembly of Nanocomposite Materials, Chapter 14, pp. 393-426, Mar. 7, 2003.

Kutsenko et al., "Structural changes in Mg alloy induced by plasma immersion ion implantation of Ag," Acta Materialia, vol. 52, pp. 4329-4335, (2004).

Kutz, "Biomaterials to Promote Tissue Regeneration," in Standard Handbook of Biomedical Engineering and Design, ISBN 0-07-135637-1, pp. 16.13-16.29, (2003).

Kvastek et al., "Electochemical properties of hydrous rithenium oxide films formed and measured at different potentials," Journal of Electroanalytical Chemistry, vol. 511, pp. 65-78, (2001).

Lakard et al., "Adhesion and proliferation of cells on new polymers modified biomaterials," Bioelectrochemistry, vol. 62, pp. 19-27, (2004).

Lakatos-Varsanyi et al., "Cyclic voltammetry measurements of different single-, bi- and multilayer TiN and single layer CrN coatings on low-carbon-steel substrates," Corrosion Science, vol. 41, pp. 1585-1598, (1999).

Lamaka et al., "TiOx self-assembled networks prepared by templating approach as nanostructured reservoirs for self-healing anticorrosion pre-treatments," Electrochemistry Comunications, vol. 8, pp. 421-428, (2006).

Lamer et al., "The Challenge of Plasma Processing—Its Diversity," Presented at the ASM Materials and Processes for Medical Devices Conference, Aug. 25-27, 2004.

Laser-Induced Forward Transfer (LIFT): Paul Scherrer Institut, (http://materials.web.psi.ch/Research/Thin_Films/Methods/LIFT.htm), pp. 1-2, downloaded Dec. 7, 2006.

Lau et al., "Hot-wire chemical vapor deposition (Hwcvd) of fluorocarbon and organosilicon thin films," Thin Solid Films, vol. 395, pp. 288-291, (2001).

LaVan et al., Small-scale systems for in vivo drug delivery, Nature Biotechnology, vol. 21, No. 10, pp. 1184-1191, Oct. 2003.

Leary-Swan et al., "Fabrication and evaluation of nanoporous alumina membranes for osteoblast culture," Journal of Biomedical Materials Research: Part A, vol. 72A, pp. 288-295, (2005).

Lee et al., "A Template-Based Electrochemical Method for the Synthesis of Multisegmented Metallic Nanotubes," Angewandte Chemie, vol. 44, pp. 6050-6054, (2005).

Lee et al., "Biocompatibility and Charge Injection Property of Iridium Film Formed by Ion Beam ty Assisted Deposition," Biomaterials, vol. 24, pp. 2225-2231, (2003).

Lee et al., "Structural characterization of porous low-k thin films prepared by different techniques using x-ray porosimetry," Journal Of Applied Physics, vol. 95, No. 5, Mar. 1, 2004.

Lee et al., "A study on electrophoretic deposition of Ni nanoparticles on pitted Ni alloy 600 with surface fractality", Journal of Colloid and Interface Science, vol. 308, pp. 413-420, (2007).

Lefaux et al., "Polyelectrolyte Spin Assembly: Influence of Ionic Strenght on the Growth of Multilayered Thin Films," Journal of Polymer Science Part B: Polymer Physics, vol. 42, pp. 3654-3666, (2004).

Lei et al., "Fabrication of Highly Ordered Nanoparticle Arrays Using Thin Porous Alumina Masks," Advanced Materials for Micro- and Nano-Systems (AMMNS), pp. 1-6, Jan. 2001.

Leng et al., "Mechanical properties and platelet adhesion behavior of diamond-like carbon films synthesized by pulsed vacuum arc plasma deposition," Surface Science, vol. 531, pp. 177-184, (2003).

Lenza et al., "In vitro release kinetics of proteins from bioactive foams," Journal of Biomedical Materials Research: A, vol. 67, No. 1, pp. 121-129, Oct. 2003.

Leoni et al., "Characterization of Nanoporous Membranes for immunoisolation: Diffusion Properties and Tissue Effects," Biomedical Microdevices, vol. 4, No. 2, pp. 131-139, (2002).

Leoni et al., "Nanoporous Platforms for Cellular Sensing and Delivery," Sensors, 51(2), pp. 111-120, (2002).

Leung et al., "Fabrication of photonic band gap crystal using microtransfer molded templates," Journal of Applied Physics, vol. 93, No. 10, pp. 5866-5870, May 15, 2003.

Lewis et al., "Silicon nonopillars formed with gold colloidal partical masking," Journal of Vacuum Science Technology B, vol. 16, No. 6, pp. 2938-2941, Nov/Dec 1998.

Li et al., "A simple approach to fabricate amorphous silicon pattern on single crystal silicon," Tribology International, Vol. 40, pp. 360-364, (2007).

Li et al., "Bioactive Hydroxyapatite Composite Coating Prepared by SOL-Gel Process," Journal of Sol-Gel Science and Technology, vol. 7, pp. 27-34, (1996).

Li et al., "Fabrication and Microstructuring of Hexagonally Ordered Two-Dimensional Nanopore Arrays in Anodic Alumina," Advanced Materials, vol. 11, pp. 483-487, (1999).

Li et al., "Hexagonal pore arrays with a 50-420 nm interpore distance formed by self-organization in anodic alumina," Journal of Applied Physics, vol. 84, No. 11, pp. 6023-6026, Dec. 1, 1998.

Li et al., "Improved biological performance of Ti implants due to surface modification by micro-arc oxidation," Biomaterials, vol. 25, pp. 2867-2875, (2004).

Li et al., "On the growth of highly ordered pores in anodized aluminum oxide," Chem. Mater., vol. 10, pp. 2470-2480, (1999).

Li et al., "pH-compensation effect of bioactive inorganic fillers on the degradation of PLGA," Composites Science and Technology, vol. 65, pp. 2226-2232, (2005).

Li et al., "Polycrystalline nanopore arrays with haxagonal ordering on aluminum," Journal of Vacuum Science Technology: A, vol. 17, pp. 1428-1431, (1999).

Li et al., "A novel method for preparing surface-modified Mg(Oh)2 nanocrystallines," Materials Science and Engineering A, 452-453, pp. 302-305, (2007).

Li, "Poly(L-glutamic acid)-anticancer drug conjugates," Advanced Drug Delivery Reviews, vol. 54, pp. 695-713, (2002).

Liaw et al., "Process Monitoring of Plasma Electrolytic Oxidation," presented at the 16th World Conference on Nondestructive Testing, Montreal, Canada, pp. 1-7, Aug. 30-Sep. 3, 2004.

Liebling et al., "Optical Properties of Fibrous Brucite from Asbestos, Quebec", American Mineralogist, vol. 57, pp. 857-864, (1972).

Lim et al., "Systematic variation in osteoblast adhesion and phenotype with substratum surface characteristics," Journal of Biomedical Materials and Research, vol. 68A, No. 3, pp. 504-511, (2004).

Lim et al., "UV-Driven Reversible Switching of a Roselike Vanadium Oxide Film between Superhydrophobicity and Superhydrophilicity," Journal of American Chemical Society, vol. 129, pp. 4126-4129, Mar. 15, 2007.

Lin et al., "PWA-doped PEG/SiO2 proton-conducting hybrid membranes for fuel cell applications," Journal of Membrane Science, vol. 254, pp. 197-205, (2005).

Lindstrom et al., "A New Method for Manufacturing Nanostructured Electrodes on Glass Substrates," Solar Energy Materials & Solar Cells, vol. 73, pp. 91-101 (2002).

Lippert et al., "Chemical and Spectroscopic Aspects of Polymer Ablation: Special Features and Novel Directions," Chemical Reviews, vol. 103, pp. 453-485, (2003).

Liu et al., "A metal plasma source ion implantation and deposition system," American Institute of Physics, Review of Scientific Instruments, vol. 70, No. 3, pp. 1816-1820, Mar. 1999.

Liu et al., "Electrodeposition of Polypyrrole Films on Aluminum from Tartrate Aqueous Solution," Journal of Brazilian Chemical Society, vol. 18, No. 1, pp. 143-152, (2007).

Liu et al., "Surface modification of titanium, titanium alloys, and related materials for biomedical applications," Materials Science and Engineering R, vol. 47, pp. 49-121, (2004).

Lu et al., "Fabricating Conducting Polymer Electrochromic Devices Using Ionic Liquids," Journal of the Electrochemical Society, vol. 151, No. 2, pp. H33-H39, (2004).

Lu et al., "Micro and nano-fabrication of biodegradable polymers for drug delivery," Advanced Drug Delivery Reviews, vol. 56, pp. 1621-1633, (2004).

Lv et al., "Controlled growth of three morphological structures of magnesium hydroxide nanoparticles by wet precipitation method," Journal of Crystal Growth, vol. 267, pp. 676-684, (2004).

Lv et al., "Controlled synthesis of magnesium hydroxide nanoparticles with different morphological structures and related properties in flame retardant ethyolene-vinyl acetate blends", Nanotechnology, vol. 15, pp. 1576-1581, (2004).

Lv et al., "In situ synthesis of nanolamellas of hydrophobic magnesium hydroxide", Colloids and Surfaces A: Physicochemical and Engineering Aspects, vol. 296, pp. 97-103, (2007).

Maeda et al., "Effect of Silica Addition on Crystallinity and Photo-Induced Hydrophilicity of Titania-Silica Mixed Films Prepared by Sol-Gel Process," Thin Solid Films, vol. 483, pp. 102-106, (2005).

Maehara et al., "Buildup of Multilayer Structures of Organic-Inorganic Hybrid Ultra Thin Films by Wet Process," Thin Solid Films, vol. 438-439, pp. 65-69, (2003).

Maheshwari et al., "Cell adhesion and motility depend on nanoscale RGD clustering," Journal of Cell Science, vol. 113, Part 10, pp. 1677-1686, May 2000.

Maitz et al., "Blood Compatibility of Titanium Oxides with Various Crystal Structure and Element Doping," Journal of Biomaterials Applications, vol. 17, pp. 303-319, Apr. 2003.

Manna et al., "Microstructural Evalution of Laser Surface Alloying of Titanium with Iridium," Scripta Materialia, vol. 37, No. 5, pp. 561-568, (1997).

Manoharan et al., "Ordered macroporous rutile titanium dioxide by emulsion templating," Proceedings of SPIE, vol. 3937, pp. 44-50, (2000).

Mantis Deposition Ltd., "Nanocluster Deposition," Thame, Oxforshire, United Kingdom, pp. 1-2, [downloaded on Feb. 2, 2007], (http://www.mantisdeposition.corninanocluster.html).

Martin et al., "Microfabricated Drug Delivery Systems: Concepts to Improve Clinical Benefit," Biomedical Microdevices, vol. 3, No. 2, pp. 97-107, Jun. 2001.

Martin, "Pulsed Laser Deposition and Plasma Plume Investigations," Andor Technology, Ltd. pp. 1-3, (2003).

Masuda et al., "Highly ordered nanochannel-array architecture in anodic alumina," Applied Physics Letters, vol. 71, pp. 2770-2772, (1997).

Matijević, "Colloid Chemical Aspects of Corrosion of Metals", Pure & Applied Chemisty, vol. 52, pp. 1179-1193, (1980).

Mattox, "Introduction: Physical Vapor Deposition (PVD) Processes," Vacuum Technology & Coating, pp. 60-63, Jul. 2002.

Mattox, "The History of Vacuum Coating Technology: Part V," Vacuum Technology & Coating, pp. 32-37, Oct. 2002.

Mattox, "The History of Vacuum Coating Technology: Part VI," Vacuum Technology & Coating, pp. 52-59, Oct. 2002.

Mauritz Group Homepage, "Sol-Gel Chemistry and Technology," (htty://www.psrc.usin.edu/mauritz/solgel.html), pp. 1-10, (downloaded [2006]).

McGuigan et al., "The influence of biomaterials on endothelial cell thrombogenicity," Biomaterials, vol. 28, pp. 2547-2571, (2007).

McNally et at., "Cathodic Electrodeposition of Cobalt Oxide Films Using Polyelectrolytes," Materials Chemistry and Physics, vol. 91, pp. 391-398, (2005).

Meijer et al., "Laser Machining by short and ultrashort pulses, state of the art and new opportunities in the age of the photons," Annals of CIRP 2002: Manufacturing Technology, vol. 51, No. 2, pp., 531-550, (2002).

Meletis et al., "Electrolytic plasma processing for cleaning and metal-coating of steel surfaces," Surface and Coatings Technology, vol. 150, pp. 246-256, (2002).

Merriam-Webster's Dictionary Website: For definition of Strut, 1 page,[first cited Jul. 21, 2010], (http://www.merriam-webster.com/dictionary/strut).

MicroFab Technologies Inc. "MicroFab: Biomedical Applications—Stents," pp. 1-4, [first downloaded Mar. 23, 2007], (http://www.microfab.com/technology/biomedical/Stents.html).

Mikhaylova et al., "Nanowire formation by electrodeposition in modified nanoporous polycrystalline anodic alumina templates," Mat. Res. Soc. Symp. Proc., vol. 704, pp. w6.34.1-W6.34.6, (2002).

Miller et al., "Endothelial and vascular smooth muscle cell function on poly(lactic-co-glycolic acid) with nano-structured surface features," Biomaterials, vol. 25, No. 1, pp. 53-61, (2004).

Miller et al., "Mechanism(s) of increased vascular cell adhesion on nanostructured poly(lactic-coglycolic acid) films," Journal of Biomedical Materials Research A, vol. 73, No. 4, pp. 476-484, (2005).

MIV Therapeutics, "Hydroxyapatite Coating," pp. 1-4, [first downloaded Jun. 25, 2003], (http://www.mivtherapeutics.com/technology/hap/).

Mobedi et al., "Studying the Degradation of Poly(L-lactide) in Presence of Magnesium Hydroxide", Iranian Polymer Journal, vol. 15, No. 1, pp. 31-39, (2006).

Mu et al., "A novel controlled release formulation for the anticancer drug paclitaxel (Taxol): PLGA nanoparticles containing vitamin E TPGS," Journal of Controlled Release, vol. 86, pp. 33-48, (2003).

Mu et al., "Vitamin E TPGS used as emulsifier in the solvent evaporation/extraction technique for fabrication of polymeric nanospheres O for controlled release of paclitaxel (Taxol)", Journal of Controlled Release, vol. 80, pp. 129-144, (2002).

Muller et al., "Solid lipid nanoparticles (S:N) for controlled drug delivery: a review of the state of the art," European Journal of Pharmaceutics and Biopharmaceutics, vol. 50, pp. 161-177, (2000).

Munchow et al., "Poly[(oligoethylene glycol) Dihydroxytitanate] as Organic-Inorganic Polymer-Electrolytes," Electrochimica Acta, vol. 45, pp. 1211-1221, (2000).

Murray et al., "Electrosynthesis of novel photochemically active inherently conducting polymers using an ionic liquid electrolyte," Electrochimica Acta, vol. 51, pp. 2471-2476, (2006).

Naganuma et al., "Preparation of Sol-Gel Derived Titanium Oxide Thin Films Using Vacuum Ultraviolet irradiation with a Xenon Excimer Lamp," Japanese Journal of Applied Physics, vol. 43, No. 9A, pp. 6315-6318, (2004).

Nair et al., "Biodegradable polymers as biomaterials", Progress in Polymer Science, vol. 32, pp. 732-798, (2007).

Nakajima et al., "Effect of Vacuum Ultraviolet Light Illumination on the Crystallization of Sol-Gel-Derived Titanium Dioxide Precursor Films," Surface & Coatings Technology, vol. 192, pp. 112-116, (2005).

Nakayama et al., "Fabrication of drug-eluting covered stents with micropores and differential coating of heparin and FK506," Cardiovascular Radiation Medicine, vol. 4, pp. 77-82, (2003).

NanoBiotech News, vol. 2, No. 26, pp. 1-9, Jun. 30, 2004.

Nanoparticle coatings: Application note, "Antimicrobial Coatings," MANTIS Deposition Ltd, pp. 1-2, (2006).

Nanu, "Nanostructured TiO2-CuInS2 based solar cells," Symposium D, Thin Film and Nano-Structured Materials for Photovoltaics, E-MRS Spring Meeting 2003, pp. 1-2, Jun. 10-13, 2003.

NASA Glenn Research Center, "Fast Three-Dimensional Method of Modeling Atomic Oxygen Undercutting of Protected Polymers," pp. 1-6, [first downloaded on Jul. 3, 2003], (http://www.grc.nasa.gov/WWW/epbranch/suurtxt/surfaceabs.htm).

Neves et al., "The morphology, mechanical properties and ageing behavior of porous injection molded starch-based blends for tissue engineering scafolding," Materials Science and Engineering, vol. C25, pp. 195-200, (2005).

Newman et al., "Alloy Corrosion," MRS Bulletin, pp. 24-28, Jul. 1999.

Ngaruiya et al., "Structure formation upon reactive direct current magnetron sputtering of transition metal oxide films," Applied Physics Letters, vol. 85, No. 5, pp. 748-750, Aug. 2, 2004.

Ngaruiya et al., "The reactive DC-Magnetron Sputtering Process,", pp. 1-5, (circa 2004).

Nicoll et al., "In vitro release kinetics of biologically active transforming growth factor-beta 1 from a novel porous glass carrier," Biomaterials, vol. 18, Issue 12, pp. 853-859, (1997).

Nicoll et al., "Nanotechnology and Biomaterials—Drugs, Drug Delivery Systems, Quantum Dots and Disease Treatment," Azom.com, pp. 1-5, [first downloaded Mar. 22, 2004], (http://www.azom.com/details.asp?ArticleID=1853).

Nie et al., "Deposition of layered bioceramic hydroxyapatite/TiO2 coatings on titanium alloys using a hybrid technique of micro-arc oxidation and electrophoresis," Surface Coatings Technology, vol. 125, pp. 407-414, (2000).

Nishio et al., "Preparation and properties of electrochromic iridium oxide thin film by sol-gel process," Thin Solid Films, vol. 350, pp. 96-100, (1999).

Noguera et al., "3D fine scale ceramic components formed by ink-jet prototyping process," Journal of the European Ceramic Society, vol. 25, pp. 2055-2059, (2005).

O'Brien et al., "Passivation of Nitinol Wire for Vascular Implants-A Demonstration of the Benefits," Biomaterials, vol. 23, pp. 1739-1748, (2002).

Oh et al., "Microstructural characterization of biomedical titanium oxide film fabricated by electrochemical method," Surface & Coatings Technology, vol. 198, pp. 247-252, (2005).

Orloff et al., "Biodegradable implant strategies for inhibition of restenosis," Advanced Drug Delivery Reviews, vol. 24, pp. 3-9, (1997).

Oxford Applied Research, "Nanocluster Deposition Systems—Nanodep60," 1 p., [first downloaded Nov. 3, 2006], (http://www.oaresearch.co.uk.nanodep60.htm).

Paik et al., "Micromachining of mesoporous oxide films for microelectromechanical system structures," Journal of Materials Research, vol. 17, pp. 2121-2129, (2002).

Palasis et al., "Analysis of Adenoviral Transport Mechanisms in the Vessel Wall and Optimization of Gene Transfer Using Local Delivery Catheters," Human Gene Therapy, vol. 11, pp. 237-246, Jan. 20, 2000.

Palasis et al., "Site-Specific Drug Delivery from Hydrogel Coated Angioplasty Catheters," Proceedings of the International Symposium on Controlled Release: Bioactive Materials, vol. 24, pp. 825-826, (1997).

Palmaz et al., "Influence of surface topography on endothelialization of intravascular metallic material," Journal of Vascular and Interventional Radiology, vol. 10, No. 4, pp. 439-444, (1999).

Pang et al., "Electrodeposition of composite hydroxyapatite-chitosan films," Materials Chemistry and Physics, vol. 94, pp. 245-251, (2005).

Pang et al., "Electropolymerization of high quality electrochromic poly(3-alkyl-thiophene)s via a room termperature ionic liquid," Electrochimica Acta, vol. 52, pp. 6172-6177, (2007).

Park et al., "Multilayer Transfer Printing for Polyelectrolyte Multilayer Patterning. Direct Transfer of Layer-by-Layer Assembled Micropatterned Thin Films," Advanced Materials, vol. 16, No. 6, pp. 520-525, Mar. 18, 2004.

Park et al., "Novel Phenylethynyl Imide Silanes as Coupling Agents for Titanium Alloy," The 22nd Annual Meeting of the Adhesion Society, pp. 1-5, Feb. 21-24, 1999.

Park et al., "Cathodic electrodeposition of RuO2 thin films from Ru(III)C13 solution", Materials Chemistry and Physics, vol. 87, pp. 59-66, (2004).

Park et al., "Microstructural change and precipitation hardeningin melt-spun Mg-X-Ca alloys," Science and Technology of Advanced Materials, vol. 2, pp. 73-78, (2001).

Pathan et al., "A chemical route to room-temperature synthesis of nanocrystalline TiO2 thin films," Applied Surface Science, vol. 246, pp. 72-76, (2005).

Pelletier et al., "Plasma-based ion implantation and deposition: A review for physics, technology, and applications," Lawrence Berkeley and National Laboratory, pp. 1-68, May 16, 2005.

Peng et al., "Role of polymers in improving the results of stenting in coronary arteries," Biomaterials, vol. 17, No. 7, pp. 658-694 (1996).

Perlman et al., "Evidence for rapid onset of apoptosis in medial smooth muscle cells after balloon injury," Circulation, vol. 95, No. 4, pp. 981-987, Feb. 18, 1997.

Pharmaceutical Science Technology, Chapter 6: Electropolymerization, pp. 24-28, (2007).

Piazza et al., "Protective diamond-like carbon coatings for future optical storage disks," Diamond & Related Materials, vol. 14, pp. 994-999, (2005).

Pitt et al., "Attachment of hyaluronan to metallic surfaces," Journal of Biomedical Materials Research, vol. 68A, pp. 95-106, (2004).

Polygenetics, "Advanced Drug Delivery," [first downloaded on May 4, 2007], 5 pages, (http://www.polygenetics.com/drug_delivery.htm).

Ponte et al., "Porosity determination of nickel coatings on copper by anodic voltammetry," Journal of Applied Electrochemistry, vol. 32, pp. 641-646, (2002).

Prior Clinicals, Boston Scientific memo, pp. 1-2, (more than a year prior to May 23, 2007).

Prokopowicz et al., "Synthesis and Application of Doxorubicin-Loaded Silica Gels as Solid Materials for Spectral Analysis," Talanta, vol. 65, pp. 663-671, (2005).

Prokopowicz et al., "Utilization of Standards Generated in the Process of Thermal Decomposition Chemically Modified Silica Gel or a Single Point Calibration of a GC/FID System," Talanta, vol. 44, pp. 1551-1561, (1997).

Pulsed Laser Deposition, (http://www.physandtech.net), pp. 1-7, Apr. 28, 2001.

PVD Materials—Materials Available for Physical Vapour Deposition (PVD) from Williams Advanced Materials. (www.azom.com), pp. 1-8, [first downloaded Apr. 28, 2006].

Qasem et al., "Kinetics of Paclitaxel 2'-N-Methylpyridinium Mesylate Decomposition," AAPS PharmaSciTech, vol. 4, No. 2, Article 21, pp. 1-8, (2003).

Qian et al., "Preparation, characterization and enzyme inhibition of methylmethacrylate copolymer nanoparticles with different hydrophilic polymeric chains," European Polyer Journal, vol. 42, pp. 1653-1661, (2006).

Qiang et al., "Hard coatings (TiN, Ti$\chi$All-$\chi$N) deposited at room temperature by energetic cluster impact," Surface and Coatings Technology, 100-101, pp. 27-32, (1998).

Qiu et al., "Self-assembled growth of MgO nanosheet arrays via a micro-arc oxidations technique," Applied Surface Science vol. 253, pp. 3987-3990, (2007).

Radin et al., "Biocompatible and Resorbable Silica Xerogel as a Long-Term Controlled Release Carrier of Vancomycin," Orthopaedic Research Society, 47th Annual Meeting, Feb. 25-28, 2001, San Francisco, CA.

Radin et al., "Silica sol-gel for the controlled release of antibiotics. I. Synthesis, characterization, and in vitro release," Journal of Biomedical Materials Research, vol. 27, No. 2, pp. 313-320, Nov. 2001.

Radin, S. et al., "In vitro bioactivity and degradation behavior of silica xerogels intended as controlled release materials," Biomaterials. vol. 23, No. 15, pp. 3113-3122, Aug. 2002.

Radtchenko et al., "A Novel Method for Encapsulation of Poorly Water-Soluble Drugs: precipitation in Polyelectrolyte multilayer shells", International Journal of Pharmaceutics, vol. 242, pp. 219-223, (2002).

Razzacki et al., "Integrated microsystems for controlled drug delivery," Advanced Drug Delivery Reviews, vol. 56, pp. 185-198, (2004).

Rees et al., "Glycoproteins in the Recognition of Substratum by Cultured Fibroblasts," Symposia of the Society for Experimental Biology: Cell-Cell Recognition, No. 32, pp. 241-260 (1978).

Reyna-Gonzales et al., "Influence of the acidity level on the electropolymerization of N-vinylcarbazole: Electrochemical study and characterization of poly(3,6-N-vinylcarbazole)," Polymer, vol. 47, pp. 6664-6672, (2006).

Rice, "Limitations of pore-stress concentrations on the mechanical properties of porous materials," Journal of Material Science, vol. 32, pp. 4731-4736, (1997).

Ristoscu, "Thin Films and Nanostructured Materials." pp. 1-2, [first downloaded Jul. 3, 2003], (http://www.. fisica.unile.it/radiazioni/ThinY02O films%20 and%20nanostmctured%20materi als.htm).

Robbie et al., "Advanced techniques for glancing angle deposition," Journal of Vacuum Science and Technology B, vol. 16, No. 3, pp. 1115-1122, (May/Jun. 1998).

Robbie et al., "Sculptured thin films and glancing angle deposition: Growth mechanics and applications," Journal of Vacuum Science Technology: A., vol. 15, pp. 1460-1465, (1997).

Roder et al., "Tuning the microstructure of pulsed laser deposited polymer-metal nanocomposites," Applied Physics A. vol. 85, pp. 15-20 (2006).

Rosen et al., "Fibrous Capsule Formation and Fibroblast Interactions at Charged Hydrogel Interfaces," Hydrogels or Medical and Related Applications, Chapter 24, pp. 329-343, Jun. 1, 1976.

Rossi et al., "Pulsed Power Modulators for Surface Treatment by Plasma Immersion Ion Impantation," Brazilian Journal of Physics, vol. 34, No. 4B, pp. 1565-1571, Dec. 2004.

Routkevitch, "Nano- and Microfabrication with Anodic Alumina: A Route to Nanodevices," Foresight Institute 9th Conference on Molecular Nanotechnology, pp. 1-20, Nov. 8-11, 2001, Santa Clara, CA.

Ryu et al., "Biomimetic apatite induction on Ca-containing titania," Current Applied Physics, vol. 5, pp. 512-515, (2005).

Santos et al., "Si-Ca-P xerogels and bone morphogenetic protein act synergistically on rat stromal marrow cell differentiation in vitro," Journal of Biomedical Materials Research, vol. 41, No. 1, pp. 87-94, Jul. 1998.

Santos et al., "Sol-Gel Derived Carrier for the Controlled Release of Proteins," Biomaterials, vol. 20, pp. 1695-1700, (1999).

Sardella et al., "Plasma-Aided Micro- and Nanopatterning Processes for Biomedical Applications," Plasma Processes and Polymers, vol. 3, pp. 456-469, (2006).

Sasahara et al., "Macroporous and nanosized ceramic films prepared by modified sol-gel methods with PMMA microsphere templates," Journal of the European Ceramic Society, vol. 24, pp. 1961-1967, (2004).

Sawitowski, "Nanoporous alumina for implant coating—A novel approach towards local therapy," NanoMed 3rd Workshop, Medical Applications of Nanotechnology, Berlin, 1 page, Feb. 17-18, 2003.

Sawyer et al., "The Role of Electrochemical Surface Properties in Thrombosis at Vascular Interfaces: Cumulative Experience of Studies in Animals and Man," Bulletin of the New York Academy of Medicine, Second Series, vol. 48, No. 2, pp. 235-256, (1972).

Sawyer, "Electrode-Biologic Tissue Interreactions at Interfaces—A Review;" Biomat. Med. Dev. Art. Org., 12(3-4), pp. 161-196 (1984).

Schetsky, "Shape Memory Alloys", Encyclopedia of Chemical Technology (3rd ed.), John Wiley & Sons, vol. 20, pp. 726-736, (1982).

Schlottig et al., "Characterization of nanoscale metal structures obtained by template synthesis," Fresenius' Journal of Analytical Chemistry, vol. 361, pp. 684-686, (1998).

Schneider, "Laser Cladding with Powder: Effect of some machining parameters on clad properties," Doctoral Thesis—University of Twente, The Netherlands, pp. 1-176, ISBN 9036510988, Mar. 1998.

Schnitzler et al., "Organic/Inorganic Hybrid Materials Formed From TiO2 Nanoparticles and Polyaniline," Journal of Brazilian Chemistry Society, vol. 15, No. 3, pp. 378-384, (2004).

Selective laser sintering, from Wikipedia, (http://en.wikipedia.org/wiki/Selective_laser_sintering), pp. 1-2, downloaded on Sep. 28, 2007.

Senior et al., "Synthesis of tough nanoporous metals by controlled electrolytic dealloying," Nanotechnology, vol. 17, pp. 2311-2316, (2006).

Serra et al., "Preparation of functional DNA microarrays through laser-induced forward transfer," Applied Physics Letters, vol. 85, No. 9, pp. 1639-1641, Aug. 30, 2004.

Serruys et al., "The Effect of Variable Dose and Release Kinetics on Neointimal Hyperplasia Using a Novel Paclitaxel—Eluting Stent Platform," Journal of the American College of Cardiology, vol. 46, No. 2, pp. 253-260, Jul. 19, 2005.

Sgura et al., The Lunar Stent: characteristics and clinical results, Herz, vol. 27, pp. 1 -14, (2002).

Shabalovskaya et al., "Surface Conditions of Nitinol Wires, Tubing, and As-Cast Alloys. The Effect of Chemical Etching, Aging in Boiling Water, and Heat Treatment," Wiley Periodicals, Inc., Journal of Biomedical Materials Research Part B: Appiled Biomaterials, vol. 65B: pp. 193-203, (2003).

Shamiryan et al., "Comparative study of SiOCH low-k films with varied porosity interacting with etching and cleaning plasma," Journal of Vacuum Science Technology B, vol. 20, No. 5, pp. 1923-1928, Sep./Oct. 2002.

Shang et al., "Structure and photocatalytic characters of TiO2 film photocatalyst coated on stainless steel webnet," Journal of Molecular Catalysis A: Chemical, vol. 202, pp. 187-1995, (2003).

Shao et al., "Fiber mats of poly(vinyl alcohol)/silica composite via Electrospinning," Materials Letters, vol. 57, pp. 1579-1584, (2003).

Shchukin et al., "Micron-scale hollow polyelectrolyte capsules with naosized magnetic Fe3O4 inside," Materials Letters, vol. 57, pp. 1743-1747, (2003).

Shevchenko et al., "Porous Surface of NiTi Alloy Produced by Plasma Ion Implantation," Institute of Ion Beam Physics and Materials Research, 1 page, May 2005.

Shevchenko, "Formation of nonoporous structures on stainless steel surface," Report, pp. 1-6, Apr. 2007.

Shibli et al., "Development of phosphate inter layered hydroxyapatite coating for stainless steel implants", Applied Surface Science, vol. 254, pp. 4103-4110, (2008).

Shockravi et al., "Soluable and thermally stable polyamides bearing 1,1'-thiobis(2-naphthoxy) groups," European Polymer Journal, vol. 43, pp. 620-627, (2007).

Shustak et al., "n-Alkanoic Acid Monolayers on 316L Stainless Steel Promote the Adhesion of electropolymerized Polypyrrole Films," Langmuir, vol. 22, pp. 5237-5240, (2006).

Siegfried et al., "Reactive Cylindrical Magnatron Deposition of Titanium Nitride and Zirconium Nitride Films," Society of Vacuum Coaters, 39th Annual Technical Conference Proceedings, pp. 97-101, (1996).

Silber et al., "A new stainless-steel-free stent with a potential of artifact free magnetic resonance compatibility: first clinical experience (Ein neuer Edelstahl-freier Stent mit Potential zur artefaktfreien MR-Kompatibilität: Erste klinische Erfahrungen)," German Society for Cardiology—Heart and Cardiovascular Research (Deutche Gesellschaft fur Kardiologie—Herz and Kreislaufforschung), 1 page, Oct. 30, 2005.

Silber et al., "A new stainless-steel-free stent with a potential of artifact free magnetic resonance compatibility: first clinical experience," Abstract and Poster, pp. 1-3, May 2006.

Silber, "LUSTY-FIM Study: Lunar Starflex First in Man Study, " PowerPoint presentation at the Paris Course on Revascularization, pp. 1-11, May 2003.

Silber, "Ein edelstahfreier stent aus niobium mit iridiumoxyd (IrOx)-beschichtung: Erste Ergebnisse der LUSTY-studie" (Stainless steel-free Stent out of niobium with iridiumoxyd (IrOx)-coating: Initial results of the LUSTY-study), PowerPoint presentation, pp. 1-16, Oct. 15, 2004.

Silber, "LUSTY-FIM Study: Lunar Starflex First in Man Study," PowerPoint presentation, pp. 1- 16, 2003.

Silber, "Niobium/iridiumoxide Stents: LUSTY randomized trial, LUNAR ROX registry," PowerPoint presentation, pp. 1-33, 2003.

Silva et al., "Electrochemical characterisation of oxide films formed on Ti-6A1-4V alloy implanted with Ir for Bioengineering applications," Electrochimica Acta, vol. 43, Nos. 1-2, pp. 203-211, (1998).

Simon et al., "Influence of topography on endothelialization of stents: Clues for new designs,"Journal of Long-Term Of Medical Implants, Voo. 10m No. 1-2, pp. 143-151, (2000).

Singer, "Paclitaxel Poliglumex (XYOTAX, CT-2103): A Macromolecular Taxane," Journal of Controlled Release, vol. 109, 120-126, (2005).

Singh et al., "Review: Nano and macro-structured component fabrication by electron beam-physical vapor deposition (EB-PVD)," Journal of Materials Science, vol. 40, pp. 1-26, (2005).

Sniadecki et al., "Nanotechnology for Cell-Substrate Interactions," Annals of Biomedical Engineering, vol. 34, No. 1, pp. 59-74, Jan. 1, 2006.

Sofield et al., "Ion beam modification of polymers," Nuclear Instruments and Methods in Physics Research, vol. B67, pp. 432-437, (1992).

Soler-Illia et al., "Block Copolymer-Templated Mesoporous Oxides," Current Opinion in Colloid and Interface Science, vol. 8, pp. 109-126, (2003).

Song et al., "Biomimetic apatite coatings on micro-arc oxidized titania," Biomaterials, vol. 25, pp. 3341-3349, (2004).

Sousa et al., "New Frontiers in Cardiology: Drug-Eluting Stents: Part I," Circulation: Journal of the Americal Heart Associate, vol. 107, pp. 2274-2279, http/www.circ.ahajournals.org, (2003).

Spasova et al., "Magnetic and optical tunable microspheres with a magnetite/gold nanoparticle shell," Journal of Material Chemisty, vol. 115, pp. 2095-2098, (2005).

Sprague et al., "Endothelial cell migration onto metal stent surfaces under static and flow conditions," Journal of Long-Term Effects of Medical Implants, vol. 10, No. 1-2, pp. 97-110, (2000).

Startschuss fur "lusty" -studie, (Launch of "lusty" -study), Cardio News, 1 page, Oct. 2002.

Stucky "High Surface Area Materials," pp. 1-5, Published: Jan. 1998, WTEC Hyper-Librarian, (http://www.wtec.org/loyola/nano/US.Review/07_03.htm).

Studart et al., "Colloidal Stabilization of Nanoparticles in Concentrated Suspensions," Langmuir, vol. 23, pp. 1081-1090, (2007).

Sun et al., "Construction of Size-Controllable Hierarchical Nanoporous TiO2 Ring Arrays and Their Modifications," Chem. Mater, vol. 18, pp. 3774-3779, (2006).

Sun et al., "Non-Fouling Biomaterial Surfaces: II Protein Adsorption on Radiation Grafted Polyethylene Glycol Methacrylate Copolymers," Polymer Preprints, vol. 28, No. 1, pp. 292-294, Apr. 1987.

Sundararajan et al., "Mechanisms underlying the formation of thick alumina coatings through the Mao coating technology," Surface and Coatings Technolgy, vol. 167, pp. 269-277, (2003).

Sung et al., "Formation of Nanoporous and Nanocrystalline Anatase Films by Pyrolysis of PEO-Ti02 Hybrid Films," Journal of Crystal Growth, vol. 286, pp. 173-177, (2006).

Szycher et al., "Drug-Eluting Stents to Prevent Coronary Restenosis," CardioTech International, pp. 1-10, (2002).

Tabata et al., "Generalized Semiempirical Equations for the Extrapolated Range of Electronics," Nuclear Instruments and Methods, vol. 103, pp. 85-91, Mar. 28, 1972.

Takitani et al., "Desorption of Helium from Austenitic Stainless Steel Heavily Bombarded by Low Energy He Ions," Journal of Nuclear Materials, vol. 329-333, pp. 761-765, (2004).

Tamura et al., "Surface Hydroxyl Site Densities on Metal Oxides as a Measrure for the Ion-Exchange Capacity," Journal of Colloid and Interface Science, vol. 209, pp. 225-231, (1999).

Tan et al., "Corrosion and wear-corrosion behavior of NiTi modified by plasma source ion implantation," Biomaterials, vol. 24, pp. 3931-3939, (2003).

Tanaka et al., "Micrometer-scale fabrication and assembly using focused ion beam," Thin Solid Films, vol. 509, pp. 113-117, (2006).

Tang et al., "Electrochemical Study of a Polarized Electrochemical Vapor Deposition Process," Journal of the Electrochemical Society, vol. 147, No. 9, pp. 3338-3344, (2000).

Tang et al., "Fabrication of Macroporous Alumina with Tailored Porosity," Jornal of American Ceramic Society, vol. 86, No. 12, pp. 2050-2054, (2003).

Tang et al., "Preparation of Porous anatase titania film," Materials Letters, vol. 58, pp. 1857- 1860, (2004).

Tapphorn et al., "The Solid-State Spray Forming of Low-Oxide Titanium Components," Journal of Metals, vol. 50, No. 9, pp. 45-46,76, (1998).

Tassin et al., "Improvement of the Wear Resistance of 316 L Stainless Steel by Laser Surface Alloying," Surface and Coatings Technology, vol. 80, No. 9, pp. 207-210, (1996).

Terlingen, "Functionalization of Polymer Surfaces," Europlasma Technical Paper, pp. 1-29, May 8, 2004.

Terumo Europe, "Terumo Europe N. V. Enrols First Patient in Clinical Trial of the Nobori Drug-Eluting Coronary Stent," Press Release, 1 page, May 26, 2005, (http://www.temmoeurope.com/_press_release/may_262005.html.).

Thierry et al., "Bioactive Coatings of Endovascular Stents Based on Polyelectrolyte Multilayers," Biomacromolecules, vol. 4, pp. 1564-1571, (2003).

Thompson et al., "Tuning compliance of nanoscale polyelectrolyte multilayers to modulate cell adhesion," Biomaterials, vol. 26, pp. 6836-6845, (2005).

Tierno et al., "Using Electroless Deposition for the Preparation of Micron Sized Polymer/Metal Core/Shell Particles and Hollow Metal Spheres," Journal of Physics Chemistry B, vol. 110, pp. 3043-3050, (2006).

Tollon, "Fabrication of coated biodegradable polymer scaffolds and their effects on murin embryonic stem cells," Thesis presented to the University of Florida, pp. 1-7, (2005).

Tonosaki et al., "Nano-indentation testing for plasma-based ion-implanted surface of plastics," Surface and Coatings Technology, vol. 136, pp. 249-251, (2001).

Torres-Costa et al., "RBS Characterization of Porous Silicon Multilayer Interference Filters," Electrochemical and Solid-State Letters, vol. 7, No. 11, pp. G244-G249 (2004).

Toth et al., "AR+ laser-induced forward transfer (LIFT): a novel method for micrometer-size surface patterning," Applied Surface Science, vol. 69, pp. 317-320, (1993).

Tsyganov et al., "Blood compatibilty of titanium-bases coatings prepared by metal plasma immersion ion implantation and deposition," Applied Surface Science, vol. 235, pp. 156-163, (2004).

Tsyganov et al., "Structure and Properties of Titanium Oxide Layers prepared by Metal Plasma Immersion Ion Implantation and Deposition," Surface & Coatings Technology, vol. 174-175, pp. 591-596, (2003).

Tsyganov et al., "Correlation between blood compatibility and physical surface properties of titanium-based coatings," Surface & Coatings Technology, vol. 200, pp. 1041-1044, (2005).

Uchida et al., "Apatite-forming ability of a zirconia/alumina nanocomposite induced by chemical treatment," Journal of Biomedical Materials Research, vol. 60, No. 2, pp. 277-282, May 2002.

University of Wisconsin, "Effect of Nano-Scale Textured Biomimetic Surfaces on Proliferation and Adhesion of Corneal Epithelial Cells," Materials Research Science and Engineering Center, pp. 12, (1997), (http://mrsec.wisc.edu/Past_proiects/seedproi4/Seedproi4.html).

Uyama et al., "Surface Modifications of Polymers by Grafting," Advances in Polymer Science, vol. 139, pp. 1-39, (1998).

Valsesia et al., "Selective immobilization of protein clusters on polymeric nanocraters," Advanced Functional Materials, vol. 16, pp. 1242-1246, (2006).

Valsesia, A. et al., "Fabrication of nanostructured polymeric surfaces for biosensing devices," Nanoletters, vol. 4, No. 6, pp. 1047-1050, (2004).

Van Alsten, "Self-Assembled Monolayers on Engineering Metals: Structure, Derivatization, and Utility," Langmuir, vol. 15, pp. 7605-7614, (1999).

Van Den Berg, "Nano particles play with electrons," pp. 1-9, [first downloaded on Nov. 12, 2003], (http://www.delftoutlook.tudelft.nl/info/index21fd.html?hoofdstuk=Article&ArtID=2243).

van der Eijk et al., "Metal Printing Process Development of a New Rapid Manufacturing Process for Metal Parts," Proceedings of the World PM2004 Conference held in Vienna, pp. 1-5, Oct. 1721, 2004.

Van Steenkiste et al., "Kinetic spray coatings," Surface & Coatings Technology, vol. 111, pp. 62- 71, (1999).

Vayssieres, "On the design of advanced metal oxide nanomaterials," International Journal of Nanotechnology, vol. 1, Nos. 1/2, pp. 1-41, (2004).

Velev et al., "Colloidal crystals as templates for porous materials," Current Opinion in Colloid & Interface Science, vol. 5, pp. 56-63, (2000).

Velev et al., "Porous silica via colloidal crystallization," Nature, vol. 389, pp. 447-448, Oct. 2, 1997.

Verheye et al., "Reduced Thrombus Formation by Hyaluronic Acid Coating of Endovascular Devices," Arteriosclerosis, Thrombosis, and Vascular Biology: Journal of The American Heart Association, vol. 20, pp. 1168-1172, (2000).

Vidal et al., "Electropolymerization of pyrrole and immobilization of glucose oxidase in a flow system: influence of the operating conditions on analytical performance," Biosensors & Bioelectronics, vol. 13, No. 3-4, pp. 371-382, (1998).

Vigil et al., "TiO2 Layers Grown from Flowing Precursor Solutions Using Microwave Heating," Langmuir, vol. 17, pp. 891-896, (2001).

Viitala et al., "Surface properties of in vitro bioactive and non-bioactive sol-gel derived materials," Biomaterials, vol. 23, pp. 3073-3086, (2002).

Vitte et al., "Is there a predictable relationship between surface physical-chemical properties and cell behaviour at the interface?" European Cells and Materials, vol. 7, pp. 52-63, (2004).

Volkel et al., "Electrodeposition of coppeer and cobalt nanostructures using self-assembled monolayer templates," Surface Science, vol. 597, pp. 32-41, (2005).

Vu et al., "Eletrophoretic deposition of nanocomposites formed from polythiophene and metal oxides," Electrochimica Acta, vol. 51, pp. 1117-1124, (2005).

Vuković et al., "Anodic stability and electrochromism of electrodeposited ruthenium-iridium coatings on titanium," Journal of Electroanalytical Chemisty, vol. 330, pp. 663-673 (1992).

Walboomers et al., "Effect of microtextured surfaces on the performance of percutaneous devices," Journal of Biomedical Materials Research Part A, Vol. 74A, No. 3, pp. 381-387, (2005).

Wang et al., "Deposition of in-plane textured MgO on amorphous Si3N4 substrates by ion-beam-assisted deposition and comparisons with ion-beam-assistend deposidted yttria-stabilized-zirconia," Applied Physics Letters, vol. 71, No. 17, Issue 20, pp. 2955-2957, Nov. 17, 1997.

Wang et al., "Effect of substrate temperature on structure and electrical resistivity of laser ablated IrO2 thin films," Applied Surface Science, vol. 253, pp. 2911-2914, (2006).

Wang et al., "Effect of the discharge pulsating on microarc oxidation coating formed on Ti6A14V alloy," Materials Chemistry and Physics, vol. 90, pp. 128-133, (2005).

Wang et al., "Novel Poly(3-nonylthiophene)-TiO2 Hybrid Materials for Photovoltaic Cells," Synthetic Metals, vol. 155, pp. 677-680, (2005).

Wang et al., "Polyelectrolyte-Coated Colloid Spheres as Templates for Sol-Gel Reactions," Chem. Mater., vol. 14, pp. 1909-1913, (2002).

Wang et al., "Pulsed laser deposition of organic thin films," This Solid Films, vol. 363, pp. 58-60, (2000).

Wang et al., "Synthesis of Macroporous Titania and Inorganic Composite Materials from Coated Colloidal Spheres—a Novel Route to Tune Pore Morphology," Chem. Mater., vol. 13, pp. 364-371, (2001).

Webster et al." Enhanced functions of osteoblasts on nanophase ceramics," Biomaterials, vol. 21, No. 17, pp. 1803-1810, Sep. 2000.

Webster et al., "Increased osteoblast adhesion on nanophase metals: Ti, Ti6A14V, and CoCrMo," Biomaterials, vol. 25, No. 19, pp. 4731-4739, (2004).

Webster et al., "Specific proteins mediate enhanced osteoblast adhesion on nanophase ceramics," Journal of Biomedical Materials Research, vol. 5, No. 51, pp. 475-483, Sep. 2000.

Wei et al., "Structural Characterisation of Doped and Undoped Nanocrystalline Zinc Oxides Deposited by Ultrasonic Spray Assisted Chemical Vapour Deposition," Journal of Physics: Conference Series, vol. 26, pp. 183-186 (2006).

Wells, "Patterned Plasma Immersion Exposure of Insulating Materials for the Purpose of Modifying Optical Properties," thesis submitted to the college of William and Mary, Williamsburg, Vriginia, pp. 1-59, Apr. 2000.

Wesolowski et al., "Surface Charge and Ion Adsorption on Metal Oxides to 290°C," Division of Chemical Sciences, Geosciences, and Biosciences, Office of Basic Energy Sciences, U.S. Department of Energy, pp. 1-6, (2001).

Wessling et al., "RF-sputtering of iridium oxide to be used as stimulation material in functional medical implants," Journal of Micromechanics and Microengineering, vol. 16, pp. S142-S148 (2006).

Whelan, "Targeted Taxane Therapy for Cancer," Drug Discovery Today, vol. 7, No. 2, pp. 90-92, Jan. 2002.

Which stent is right for you? pp. 1-3, (circa 2004).

Wieneke et al., "Synergistic Effects of a Novel Nanoporous Stent Coating and Tacrolimus on Intima Proliferation in Rabbits," Catheterization and Cardiovascular Interventions, vol. 60, pp. 399-407, (2003).

Wilkinson et al., "Nanofabrication in cellular engineering," Journal of Vacuum Science & Technology B, vol. 16, No. 6, pp. 3132-3136, (1998).

Wilkinson et al., "The use of materials patterned on a nano- and micro-metric scale in cellular engineering," Materials Science & Engineering C, vol. 19, No. 1-2, pp. 263-269, (2002).

Wilson et al., "Mediation of biomaterial-cell interactions by adsorbed proteins: a review," Tissue Engineering, vol. 11, No. 1-2, pp. 1-18, (2005).

Wong et al., "Balance of chemistry, topography, and mechanics at the cell-biomaterial interface: Issues and challenges for assessing the role of substrate mechanics on cell response," Surface Science, vol. 570, No. 1-2, pp. 119-133, (2004).

Wong et al., "Polymer segmental alignment in polarized pulsed laser-induced periodic surface structures," Applied Physics A, vol. 65, pp. 519-523, (1997).

Wood, "Next-generation drug-eluting stents tackle shortcomings of Cypher, Taxus," Heart Wire, pp. 1-6, Feb. 7, 2006, (http://www.theheart.org/article/641591.do.).

World Reference definition, "Interconnected," WorldReference.com, 1 page, [downloaded Jan. 21, 2010].

Wu et al., "Characterization of Mesoporous Nanocrystalline TiO2 Photocatalysts Synthesized Via a Sol-Solvothermal Process at a Low Temperature," Journal of Solid State Chemistry, vol. 178, pp. 321-328, (2005).

Wu et al., "Chitosan-Mediated and Spatially Selective Electrodeposition of Nanoscale Particles," Langmuir, vol. 21, pp. 3641-3646, (2005).

Wu et al., "Corrosion resistance of BaTiO3 films prepared by plasma electrolytic oxidation," Surface and Coatings Technology, vol. 166, pp. 31-36, (2002).

Wu et al., "Design of Doped Hybrid Xerogels for a Controlled Release of Brilliant Blue FCF," Journal of Non-Crystalline Solids, vol. 342, pp. 46-53, (2004).

Wu et al., "The effects of cathodic and anodic voltages on the characteristics of purous nanocrystalline titania coatings fabricated by microarc oxidation," Materials Letters, vol. 59, pp. 370-375, (2005).

Xia et al., "Monodispersed Colloidal Spheres: Old Materials with New Applications," Advanced Materials, vol. 12, No. 10, pp. 693-713, (2000).

Xu et al., "An Improved Method to Strip Aluminum from Porous Anodic Alumina Films," Langmuir, vol. 19, pp. 1443-1445, (2003).

Xu et al., "Cold spay deposition of thermoplastic powder," Surface & Coatings Technology, vol. 2001, pp. 3044-3050, (2006).

Xu et al., "Synthesis of porosity controlled ceramic membranes," Journal of Material Research, vol. 6, No. 5, pp. 1073-1081, May 1991.

Yamato et al. "Nanofabrication for micropatterned cell arrays by combining electron beam-irradiated polymer grafting and localized laser ablation," Journal of Biomedical Materials Research, vol. 67, No. 4, pp. 1065-1071, Dec. 15, 2003.

Yan et al., "New MOCVD precursor for iridium thin films deposition," Materials Letters, vol. 61, pp. 216-218, (2007).

Yan et al., "Sol-gel Processing," Handbook of Nanophase and Nanostructured Materials, vol. 1: Synthesis, Chapter 4, pp. 1-27, (2003).

Yang et al., "Laser spray cladding of porous NiTi coatings on NiTi substrates," The Hong Kong Polytechnic University, 1 page, Dec. 28, 2006.

Yang et al., "Poly(L,L-lactide-co-glycolide)/tricalcium phosphate composite scaffold and its various changes during degradation in vitro," Polymer Degradation and Stability, vol. 91 pp. 3065-3073, (2006).

Yang et al., "Thermal oxidation products and kinetics of polyethylene composites," Polymer Degradation and Stability, vol. 91, pp. 1651-1657, (2006).

Yang et al., "Solution phase synthesis of magnesium hydroxide sulfate hydrate nanoribbons", Nanotechology, vol. 15, pp. 1625-1627, (2004).

Yankov et al., "Reactive plasma immersion ion implantation for surface passivation," Surface and Coatings Technology, vol. 201, pp. 6752-6758, (2007).

Yap et al., "Protein and cell micropatterning and its integration with micro/nanoparticles assembley," Biosensors and Bioelectronics, vol. 22, pp. 775-788, (2007).

Yerokhin et al., "Kinetic aspects of aluminium titanate layer formation on titanium alloys by plasma electrolytic oxidation," Applied Surface Science, vol. 200, pp. 172-184, (2002).

Yerokhin et al., "Plasma electrolysis for surface engineering," Surface Coatings Technology, vol. 122, pp. 73-93, (1999).

Yim et al., "Nanopattern-induced changes in morphology and motility of smooth muscle cells," Biomaterials, vol. 26, pp. 5405-5413, (2005).

Yim et al., "Significance of synthetic nanostructures in dictating cellular response," Nanomedicine: Nanotechnology, Biology and Medicine, vol. 1, No. 1, pp. 10-21, Mar. 1, 2005.

Yoldi et al., "Electrophoretic deposition of colloidal crystals assisted by hydrodynamic flows," Journal of Materials Science, vol. 41, pp. 2964-2969, (2006).

Yoshida et al., "Impact of Low Energy Helium Irradiation on Plasma Facing Metals," Journal of Nuclear Materials, vol. 337-339, pp. 946-950, (2005).

Young et al., "Polarized electrochemical vapor deposition for cermet anodes in solid oxide fuel cells," Solid State Ionics, vol. 135, pp. 457-462, (2000).

Yu et al., "Encapsulated cells: an atomic force microscopy study," Biomaterials, vol. 25, pp. 3655-3662, (2004).

Yu et al., "Enhanced photocatalytic activity of mesoporous and ordinary TiO2 thin films by sulfuric acid treatment," Applied Catalysis B: Environmental, vol. 36, pp. 31-43, (2002).

Yu et al., "Enhanced photoinduced super-hydrophilicity of the sol-gel-derived TiO2 thin films by Fe-doping," Materials Chemistry and Physics, vol. 95, pp. 193-196, (2006).

Yu et al., "Light-induced super-hydrophilicity and photocatalytic activity of mesoporous TiO2 thin films," Journal of Photochemistry and Photobiology A: Chemistry, vol. 148, pp. 331-339, (2002).

Yun et at., "Low-Temperature Coating of Sol-Gel Anatase Thin Films," Materials Letters, vol. 58, pp. 3703-3706, (2004).

Zakharian et al., "A Fullerene- Paclitaxel Chemotherapeutic: Synthesis, Characterization, and Study of Biological Activity in Tissue Culture," Journal of American Chemistry Society, vol. 127, pp. 12508-12509, (2005).

Zbroniec et al., "Laser ablation of iron oxide in various ambient gases," Applied Surface Science, vol. 197-198, pp. 883-886, (2002).

Zeng et al., "Biodegradable electrospun fibers for drug delivery," Journal of Controlled Release, vol. 92, pp. 227-231, (2003).

Zhang et al., "Surface analyses of micro-arc oxidized and hydrothermally treated titanium and effect on osteoblast behavior," Journal of Biomedical Materials Research, vol. 68A, pp. 383-391, (2004).

Zhang et al., "Surface treatment of magnesium hydroxide to improve its dispersion in organic phase by the ultrasonic technique", Applied Surface Science, vol. 253, pp. 7393-7397, (2007).

Zhao et al., "Coating deposition by the kinetic spray process," Surface & Coatings Technology, vol. 200, pp. 4746-4754, (2006).

Zhao et al., "Designing Nanostructions by Glancing Angle Deposition," Proceedings of SPIE, vol. 5219: Nanotubes and Nanowires, pp. 59-73, (2003).

Zhao et al., "Formulation of a ceramic ink for a wide-array drop-on-demand ink jet printer," Ceramics International, vol. 29, pp. 887-892, (2003).

Zheng et al., "Substrate temperature dependent morphology and resistivity of pulsed laser deposited iridium oxide thin films," Thin Solid Films, vol. 496, pp. 371-375, (2006).

Zheng et al., "Synthesis of Mesoporous Silica Materials via Nonsurfactant Templated Sol-Gel Route Using Mixture of Organic Compounds as Template," Journal of Sol-Gel Science and Technology, vol. 24. pp. 81-88, (2002).

Zhitomirsky et al., "Cathodic electrodeposition of MnOx films for electrochemical supercapacitors," Electrochimica Acta, vol. 51, pp. 3039-3045, (2006).

Zhitomirsky et al., "Electrodeposition of composite hydroxyapatite-chitosan films," Materials Chemistry and Physics, Vol. 94, pages 245-251, (2005).

Zhou et al., "Branched Ta nanocolumns grown by glancing angle deposition," Applied Physics Letters, vol. 88, p. 203-117, (2006).

Zoppi et al., "Hybrid Films of Poly(ethylene oxide-b-amide 6) Containing Sol-Gel Silicon or Titanium Oxide as Inorganic Fillers: Effect of Morphology and Mechanical Properties on Gas Permeability," Polymer, vol. 41, pp. 5461-5470, (2000).

Zou et al., "Highly textural lamellar mesostructured magnesium hydroxide via a cathodic electrodeposition process", Materials Letters, vol. 61, pp. 1990-1993, (2007).

US 6,533,715, 03/2003, Hossainy et al. (withdrawn)

* cited by examiner

MEDICAL DEVICE WITH A POROUS SURFACE FOR DELIVERY OF A THERAPEUTIC AGENT

RELATED APPLICATIONS

This application claims priority to U.S. Provisional Application No. 60/904,674, filed Mar. 1, 2007.

FIELD OF THE INVENTION

The present invention is generally directed to implantable medical devices for delivering therapeutic agents to the body tissue of a patient and methods for making such medical devices. In particular, the present invention is directed to implantable medical devices, such as intravascular stents, having a surface that includes a plurality of cavities and a plurality of pores and a composition disposed in the pores and/or cavities, as well as, implantable medical devices, such as intravascular stents, having a surface that has a coating composition disposed on the surface, wherein the coating composition includes a plurality of cavities and a plurality of pores and another coating composition disposed in the pores and/or cavities.

BACKGROUND

Medical devices have been used to deliver therapeutic agents locally to the body tissue of a patient. For example, stents having a coating containing a therapeutic agent, such as an anti-restenosis agent, can be effective in treating or preventing restenosis. Currently, such medical device coatings include a therapeutic agent alone or a combination of a therapeutic agent and a polymer. Both of these types of coatings suffer from certain limitations.

Coatings containing a therapeutic agent without a polymer are generally impractical since such coatings offer little or no control over the rate of release of the therapeutic agent. Therefore, many medical device coatings include a therapeutic agent and a polymer.

Though the use of polymers can provide control over the rate of release of the therapeutic agent, the use of such polymers in coatings may pose certain other limitations. For example, some polymer coating compositions do not actually adhere to the surface of the medical device. In order to ensure that the coating compositions remain on the surface, the area of the medical device that is coated, such as a stent strut, is encapsulated with the coating composition. However, since the polymer does not adhere to the medical device, the coating composition is susceptible to deformation and damage during loading, deployment and implantation of the medical device. Any damage to the polymer coating may alter the therapeutic agent release profile and can lead to an undesirable increase or decrease in the therapeutic agent release rate. Also, polymer in the coatings may react with the blood and cause late stage thrombosis.

For instance, balloon expandable stents must be put in an unexpanded or "crimped" state before being delivered to a body lumen. During the crimping process coated stent struts are placed in contact with each other and can possibly adhere to each other. When the stent is expanded or uncrimped, the coating on the struts that have adhered to each other can be damaged, torn-off or otherwise removed. Moreover, if the polymer coating is applied to the inner surface of the stent, it may stick or adhere to the balloon used to expand the stent when the balloon contacts the inner surface of the stent during expansion. Such adherence to the balloon may prevent a successful deployment of the medical device.

Similar to balloon-expandable stents, polymer coatings on self-expanding stents can also interfere with the delivery of the stent. Self-expanding stents are usually delivered using a pull-back sheath system. When the system is activated to deliver the stent, the sheath is pulled back, exposing the stent and allowing the stent to expand itself. As the sheath is pulled back it slides over the outer surface of the stent. Polymer coatings located on the outer or abluminal surface of the stent can adhere to the sheath as it is being pulled back and disrupt the delivery of the stent.

An alternative to coating or encapsulating the surface of a medical device is to create pores within the surface of the medical device and dispose a therapeutic agent within the pores. Though the use of a porous surface overcomes certain limitations of using a polymer coating, due to the small size of the pores the therapeutic agent may only penetrate to a certain depth of the porous coating. Such insufficient penetration can result in a limited amount of the therapeutic agent that can be loaded onto the medical device, as well as, an unwanted rate of release where the therapeutic agent is released over a short period of time. Also due to the limited surface area of the surface of the medical device, a limited number of pores and therefore, a limited amount of a therapeutic agent can be loaded onto the surface of the medical device.

Accordingly, there is a need for medical devices and coatings for medical devices that have little or no polymer and that can release an effective amount of a therapeutic agent in a controlled release manner while avoiding the disadvantages of current coatings for medical devices. Also, there is a need for coatings that can release an effective amount of a therapeutic agent in a controlled release manner that can be selectively applied to the surfaces of a medical device, such as the surfaces that contact the body tissue of a patient. Additionally, there is a need for methods of making such medical devices and coatings for medical devices.

SUMMARY

As used herein, and unless otherwise indicated, the terms "controlled release," "sustained release", "modulated release" and "modified release" can be used interchangeably and are used to describe the release profile of a therapeutic agent that is not an immediate release profile.

These and other objectives are accomplished by the present invention. The present invention provides a coating for a medical device, such as an intravascular stent, that is capable of releasing an effective amount of a therapeutic agent in a controlled release manner, without the limitations associated with current coatings, including polymer coatings. The coatings of the present invention can be applied to select surfaces of a medical device such as the medical device surfaces that contact the surface of a body lumen of a patient. Such selective application of the coatings of the present invention can increase the accuracy and economical use of a therapeutic agent.

In certain embodiments of the present invention, the coatings of the present invention include a first coating composition having a metal, a metal oxide, ceramic oxide, or inert carbon and a plurality of cavities and a plurality of pores within the first coating composition. At least some of the pores are formed on the surface of the cavities. The coatings also include a second coating composition having a therapeutic agent disposed in at least one of the pores.

For example, the present invention includes an implantable stent comprising a stent sidewall structure, such as a tubular stent sidewall structure, having a surface and a coating that includes a first coating composition disposed on at least a portion of the surface of the stent sidewall structure. The first coating composition has an exposed surface and includes a metal, a metal oxide, ceramic oxide, or inert carbon having a plurality of cavities therein. Some of the cavities are in fluid communication with the exposed surface and at least one of the cavities is defined by a cavity surface having a plurality of pores therein. The coating also includes a second coating composition comprising a first therapeutic agent, wherein the second coating composition is disposed within at least one of the pores.

In the above example, at least one of the pores of the first coating composition can be in fluid communication with the cavity surface. Additionally, the pores can be distributed throughout the first coating composition. In certain embodiments the pores can be homogenously distributed throughout the first coating composition.

Also, in the above described example, the second coating composition can also be disposed within at least one of the cavities. In certain embodiments, the second coating composition further includes a polymer.

The coatings of the present invention can further include a third coating composition having a second therapeutic agent, a polymer or both a therapeutic agent and a polymer. The third coating composition can also be disposed in at least one of the cavities.

Suitable stents for the embodiments described herein can have a sidewall structure having an abluminal surface having a plurality of struts and openings in the sidewall structure. In certain embodiments, the surface of the stent sidewall is the abluminal surface. The first composition, second composition or third coating composition can conform to the surface of the stent so that the openings in the stent sidewall structure are preserved. Examples of such suitable stents include, but are not limited to, intravascular stents such as intravascular balloon-expandable stents and intravascular self-expanding stents.

The first coating composition can be free of any polymer. Additionally, the first coating composition can be radiopaque. For the first coating composition, suitable metal oxides or ceramic oxides include but are not limited to, iridium oxide, titanium oxide, titanium dioxide, iron oxide, hydroxyapatite, calcium phosphates, alumina, zirconia, zirconium, silica based glasses, or a combination thereof. For the first coating composition, suitable metals include but are not limited to, gold tantalum, platinum, titanium, Nitinol or a combination thereof.

The first coating composition can have a thickness of about 1 micron to about 30 microns. The diameter or width of the pores in the first coating composition can be less than or equal to about one micron. The size of the cavities in the first coating composition can be greater than or equal to about one micron.

In other embodiments of the present invention, the present invention includes, an implantable stent having a stent sidewall structure, such as a tubular stent sidewall structure having a surface, wherein the stent sidewall structure includes a metal, a metal oxide, ceramic oxide or inert carbon having a plurality of cavities therein. At least some of the cavities can be in fluid communication with the surface and at least one cavity is defined by a cavity surface having a plurality of pores therein. The stent also includes a first composition that includes a first therapeutic agent, wherein the first composition is disposed within at least some of the pores.

In the above embodiments, at least one of the pores can be in fluid communication with the cavity surface. The pores can be distributed throughout the stent sidewall structure. For example, the pores can be homogenously distributed throughout the stent sidewall structure.

The diameter or width of the pores in the cavity surface can be less than or equal to about one micron. The size of the cavities in the stent sidewall structure can be greater than or equal to about one micron. The stent sidewall structure can be radiopaque. Suitable metal oxides or ceramic oxides for the stent sidewall structure include, but are not limited, iridium oxide, titanium oxide, titanium dioxide, iron oxide, hydroxyapatite, calcium phosphates, alumina, zirconia, zirconium, silica based glasses, or a combination thereof. For the first coating composition, suitable metals include but are not limited to Suitable metals for the stent sidewall structure include but are not limited to, gold, tantalum, platinum, titanium, Nitinol or a combination thereof.

The first composition can also be disposed in at least one of the cavities. The first coating composition can further include a polymer. Alternatively, the stents of the present invention can further include a second composition having a second therapeutic agent, a polymer or both a therapeutic agent and a polymer, wherein the second composition is disposed in at least some of the cavities. Also, the second composition can also be disposed within at least one of the pores.

Polymers in any of the above discussed embodiments of the coatings of the present invention can include biostable and bioabsorbable polymers. Suitable polymers include, but are not limited to, styrene-isobutylene-styrene, polylactic-co-glycolic acid (PLGA), polybutyl methacrylate (PBMA), polyvinylidene fluoride (PVDF), or a combination thereof.

Suitable stents for the embodiments described herein can have a sidewall structure having an abluminal surface having a plurality of struts and openings in the sidewall structure. In certain embodiments, the first composition and/or second composition can conform to the surface of the stent so that the openings in the stent sidewall structure are preserved. Examples of such suitable stents include, but are not limited to intravascular stents such as intravascular balloon-expandable stents and intravascular self-expanding stents.

Suitable therapeutic agents that can be included in the coatings of the present invention include, but are not limited, to anti-thrombogenic agents, anti-angiogenesis agents, anti-proliferative agents, antibiotic, anti-restenosis agents, growth factors, immunosuppressants or radiochemicals. In some preferred embodiments the therapeutic agent is an anti-restenosis agent. More specifically, suitable therapeutic agents include, but are not limited to, paclitaxel, sirolimus, tacrolimus, pimecrolimus, zotarolimus or everolimus. When the embodiments of the present invention include a first and second therapeutic agent the first therapeutic agent and second therapeutic agent can be the same or different.

The present invention is also directed to methods of coating a medical device having a surface. For example the present invention includes a method of coating an implantable stent having a surface that includes the steps of (a) disposing a first coating composition on the surface, wherein the first coating composition includes a metal, a metal oxide, ceramic oxide or inert carbon; (b) creating a plurality of cavities in the first coating composition, wherein the cavities have a cavity surface; (c) creating a plurality of pores within the cavity surface; and (d) disposing a second coating composition within at least one of the pores, wherein the second coating composition comprises a first therapeutic agent.

The methods of the present invention also include a method of coating an implantable stent having a surface that includes the steps of (a) disposing a first coating composition on the surface, wherein the first coating composition includes a metal, a metal oxide, ceramic oxide or inert carbon, and wherein the first coating composition comprises a plurality of pores therein; (b) creating a plurality of cavities in the first coating composition; and (c) disposing a second coating composition within at least one of the pores, wherein the second coating composition comprises a first therapeutic agent. The plurality of pores can be formed or created or they can be naturally occurring in the metal, metal oxide, ceramic oxide or inert carbon.

The above described methods can further include disposing the second coating composition within at least some of the cavities. The second coating composition can also include a polymer. In certain embodiments the above methods can further include disposing a third coating composition within at least some of the cavities, wherein the third coating composition comprises a second therapeutic agent, a polymer or both a second therapeutic agent and a polymer. The cavities can be formed by laser ablation, drilling, chemical etching or a combination thereof.

The methods of the present invention also include, for example, a method of coating an implantable stent having a surface that includes a metal, a metal oxide, ceramic oxide or inert carbon having a plurality of pores therein, the method includes the steps of (a) creating a plurality of cavities in the surface, wherein the cavities have a cavity surface and wherein at least some of the pores are in fluid communication with a portion of the cavity surface; and (b) disposing a first composition comprising a first therapeutic agent within at least some of the pores. The plurality of pores can be formed or created or they can be naturally occurring in the metal, metal oxide, ceramic oxide or inert carbon.

The methods of the present invention also include a method of coating an implantable stent having a surface that includes a metal, a metal oxide, ceramic oxide or inert carbon, the method includes the steps of: (a) creating a plurality of cavities in the metal, metal oxide, ceramic oxide or inert carbon, wherein the cavities have a cavity surface; (b) creating a plurality of pores in the metal, metal oxide, ceramic oxide or inert carbon and wherein at least some of the pores are in fluid communication with a portion of the cavity surface; and (c) disposing a first composition having a first therapeutic agent within at least some of the pores.

The above described methods can further include disposing the first composition within at least some of the cavities. The first composition can further include a polymer. Alternatively, the methods can further include disposing a second composition within at least some of the cavities, wherein the second composition includes a second therapeutic agent, a polymer or a second therapeutic agent and a polymer. The cavities can be formed by laser ablation, drilling, chemical etching or a combination thereof.

BRIEF DESCRIPTION OF THE DRAWINGS

The present invention will be explained with reference to the following drawings.

DETAILED DESCRIPTION

In certain embodiments, the medical devices of the present invention have a surface that has a coating disposed thereon. The coating includes a first coating composition that includes a metal, a metal oxide, ceramic oxide or inert carbon having a plurality of cavities therein. Also, when the first coating composition is disposed on the surface, the first coating composition has an exposed surface that is in fluid communication with some of the cavities. At least one of the cavities is defined by a cavity surface having a plurality of pores therein. The coatings further include a second coating composition having a first therapeutic agent disposed within at least one of the pores.

Figure 1:
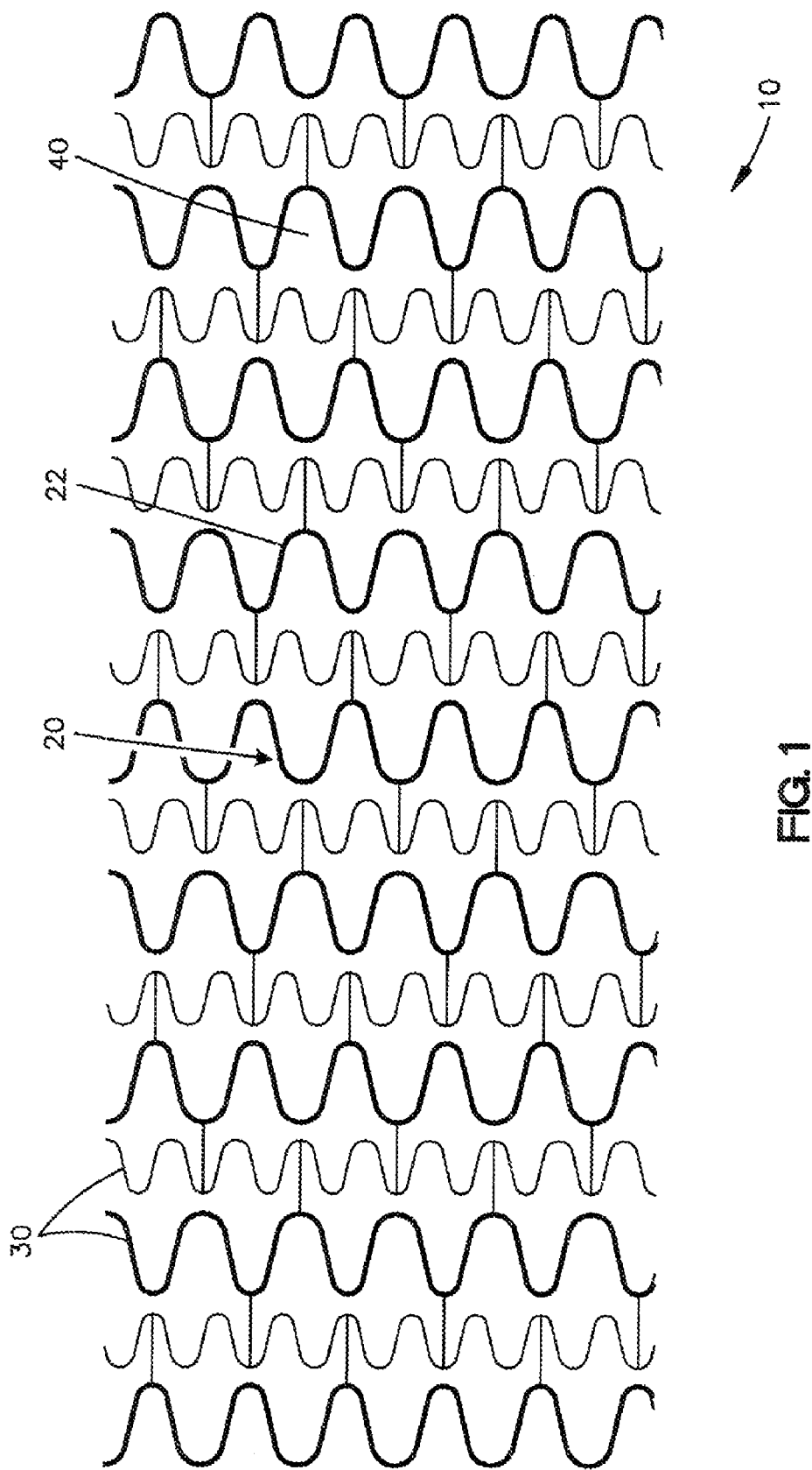
FIG. 1 shows an example of a medical device that is suitable for use in the present invention.

FIG. 1 shows an example of a medical device that is suitable for use in the present invention. This figure shows an implantable intravascular stent 10. As shown in FIG. 1 intravascular stent 10 is unrolled, but is generally cylindrical in shape. Stent 10 includes a sidewall 20 which comprises a plurality of struts 30 and at least one opening 40 in the sidewall 20. Generally, the opening 40 is disposed between adjacent struts 30. Also, the stent sidewall structure 20 may have a first sidewall surface 22 and an opposing second sidewall surface 54, which is not shown in FIG. 1 but can be seen in FIG. 2. The first sidewall surface 22 can be an outer or abluminal sidewall surface, which faces a body lumen wall when the stent is implanted, or an inner or luminal sidewall surface, which faces away from the body lumen surface. Likewise, the second sidewall surface can be an abluminal sidewall surface or a luminal sidewall surface.

When the coatings of the present invention are applied to a stent having openings in the stent sidewall structure, in certain embodiments, it is preferable that the coatings conform to the surface of the stent so that the openings in the sidewall stent structure are preserved, e.g. the openings are not entirely or partially occluded with coating material.

Figure 2:
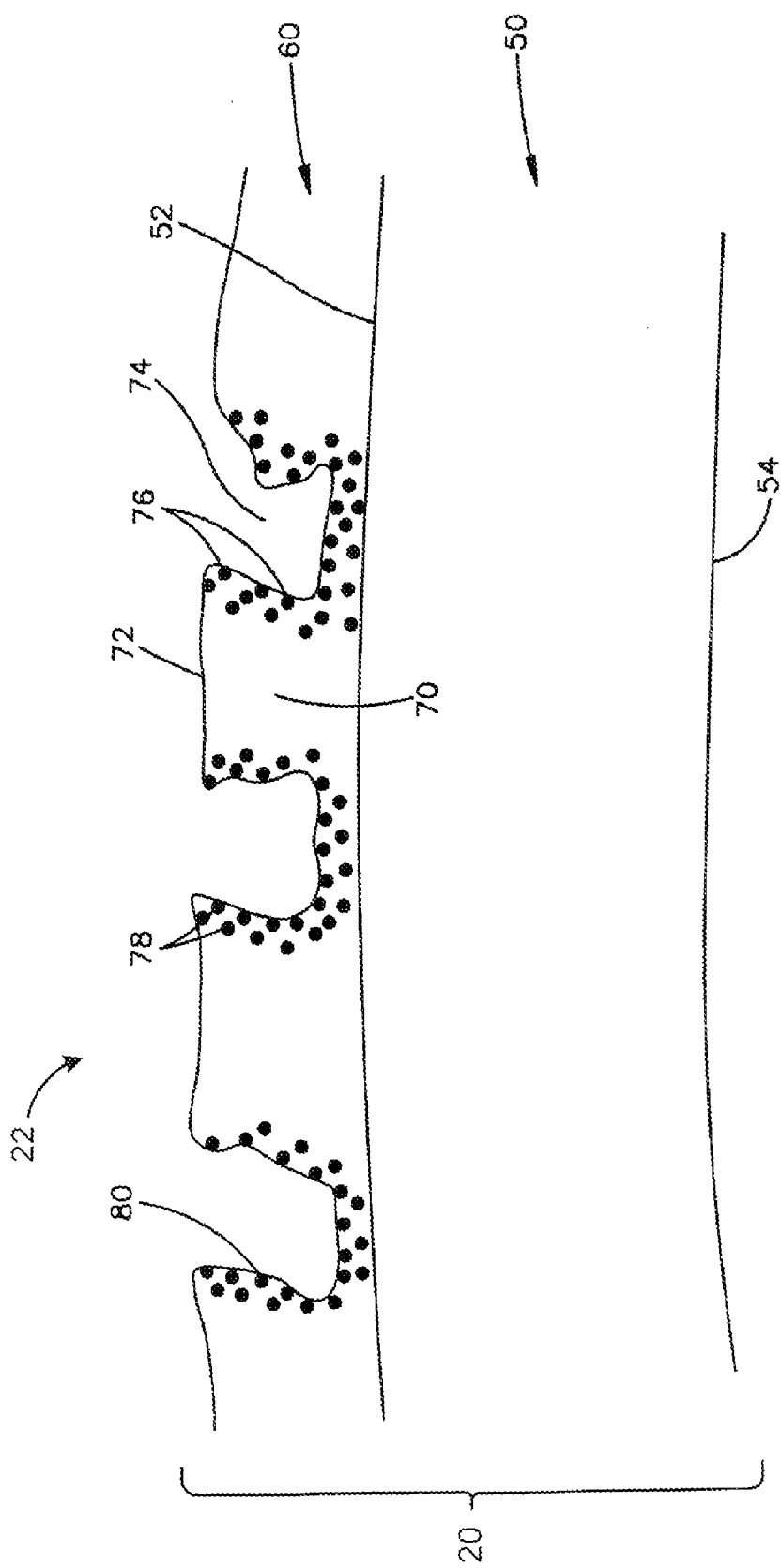
FIG. 2 shows a cross-sectional view of an embodiment of a coating composition having cavities and pores disposed on a portion of a stent.

FIG. 2 shows a cross-sectional view of an embodiment of a coating of the present invention disposed on a stent strut. Stent strut 50 has a surface, such as an abluminal surface 52 and a luminal surface 54. In this embodiment, coating 60 is disposed on the abluminal surface 52 of stent strut 50. Coating 60 comprises a first coating composition 70 comprising a metal, a metal oxide, ceramic oxide or an inert carbon. In certain embodiments, the first coating composition is free of any polymer, or substantially free of any polymer, i.e. contains less than 50% polymer by weight of the first coating composition. The first coating composition 70 has an exposed surface 72. An exposed surface is an outer surface that is capable of contacting body tissue when the device is inserted or implanted and is not covered by another material. The first coating composition 70 also includes a plurality of cavities 74 therein, in which at least some of the cavities are in fluid communication with the exposed surface 72. When the cavities are in fluid communication with the exposed surface, materials or fluids placed in the cavity can come into contact with the exposed surface. The cavities 74 have a cavity surface 76, i.e. a surface that defines the cavity. Additionally, the first coating composition includes a plurality of pores 78, at least some of which are in fluid communication with cavity surface 76. When the pores are in fluid communication with the cavity surface, materials or fluids placed in the pores can come into contact with the cavity surface. As shown in this embodiment, the pores are disposed on or near the cavity surface. Disposed within some of the pores 78 is a second coating composition comprising a therapeutic agent 80. The cavities increase the surface area of the coating and allow the therapeutic agent to penetrate deeper into the coating.

Figure 3:
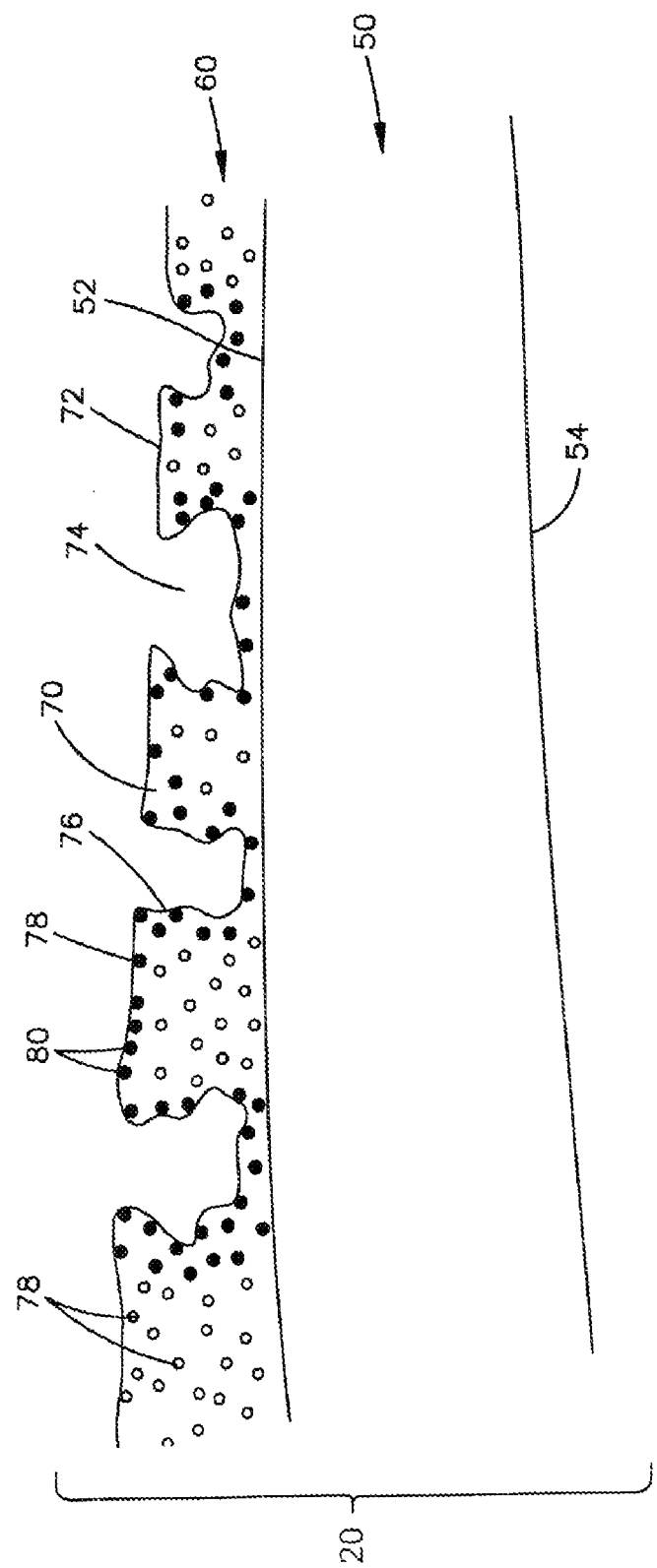
FIG. 3 shows a cross-sectional view of another embodiment of a coating composition having cavities and pores disposed on a portion of a stent.

FIG. 3 shows a cross-sectional view of a coating of the present invention disposed on a surface of a stent strut. As shown in FIG. 3, stent strut 50 has an abluminal surface 52 and a luminal surface 54. In this embodiment, coating 60 is disposed on the abluminal surface 52 of stent strut 50. Coating 60 comprises a first or surface coating composition 70 comprising a metal, a metal oxide, ceramic oxide or an inert carbon, wherein the first coating composition 70 has an exposed surface 72. The first coating composition 70 also has a plurality of cavities 74 at least some of which are in fluid communication with the exposed surface 72. The cavities 74 have a cavity surface 76. Additionally, the first coating composition includes a plurality of pores 78 positioned throughout the first coating composition, some of which are in fluid communication with cavity surface 76. Disposed within some of the pores 78 is a second coating composition 79 comprising a therapeutic agent 80.

The location and number of pores can vary depending on the desired amount of therapeutic agent that is to be loaded onto the coating as well as the desired therapeutic agent release profile. Pores can be in a discreet area such as on or near the cavity surface, as shown in FIG. 2 or throughout the first coating composition, as shown in FIG. 3. In certain embodiments, pores can be homogeneously, i.e. evenly, distributed throughout the first coating composition. In other embodiments, the pores may be disposed in a pattern. Patterns can be random or uniform.

Figure 4:
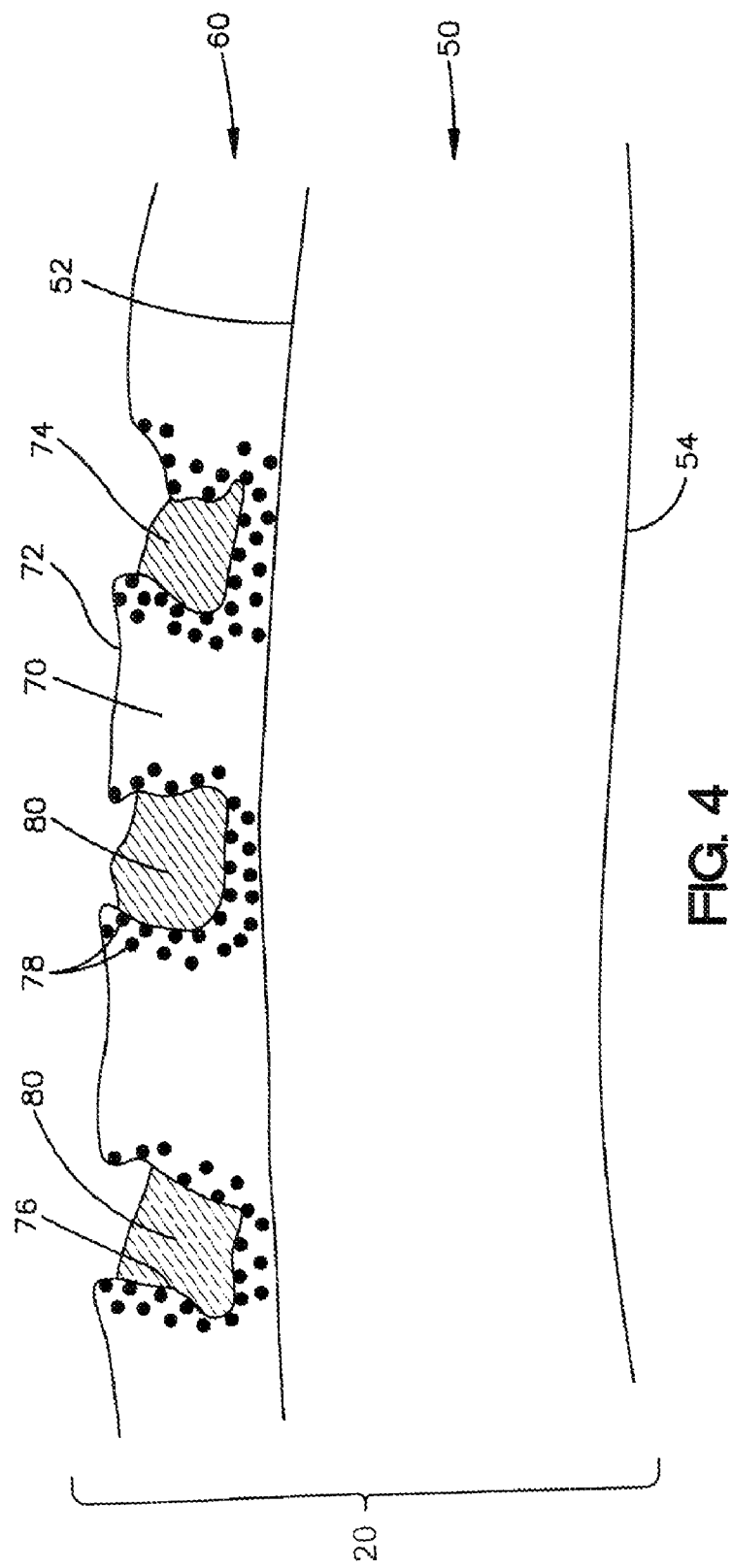
FIG. 4 shows a cross-sectional view of an embodiment of a first coating composition having cavities and pores disposed on a portion of a stent, wherein the pores and cavities contain a second coating composition.

FIG. 4 shows a cross-sectional view of a coating of the present invention disposed on a surface of a stent strut. The stent strut 50 has an abluminal surface 52 and a luminal surface 54. In this embodiment, coating 60 is disposed on the abluminal surface 52 of stent strut 50. Coating 60 comprises a first coating composition 70 comprising a metal, a metal oxide, ceramic oxide or an inert carbon, wherein the first coating composition 70 has an exposed surface 72. The first coating composition 70 also has a plurality of cavities 74 at least some of which are in fluid communication with the exposed surface 72. The cavities 74 have a cavity surface 76. Additionally, the first coating composition includes a plurality of pores 78, some of which are in fluid communication with a cavity surface 76. As shown in this embodiment, disposed within some of the cavities 74 and pores 78 is a second coating composition comprising a therapeutic agent 80. The benefit to disposing the therapeutic agent in both the cavities and the pores is to allow for a therapeutic agent release profile that has a quick release and a controlled release profile. The therapeutic agent in the cavities can release quickly into the body lumen, thus displaying a "burst effect." After the therapeutic agent has released from the cavities the therapeutic agent disposed in the pores can then release more slowly displaying a more controlled release profile. Additionally, once the release of the therapeutic agent is complete, having the cavities in communication with the exposed surface can aid in vascularization and cell coverage for long-term non-inflammation.

Figure 5:
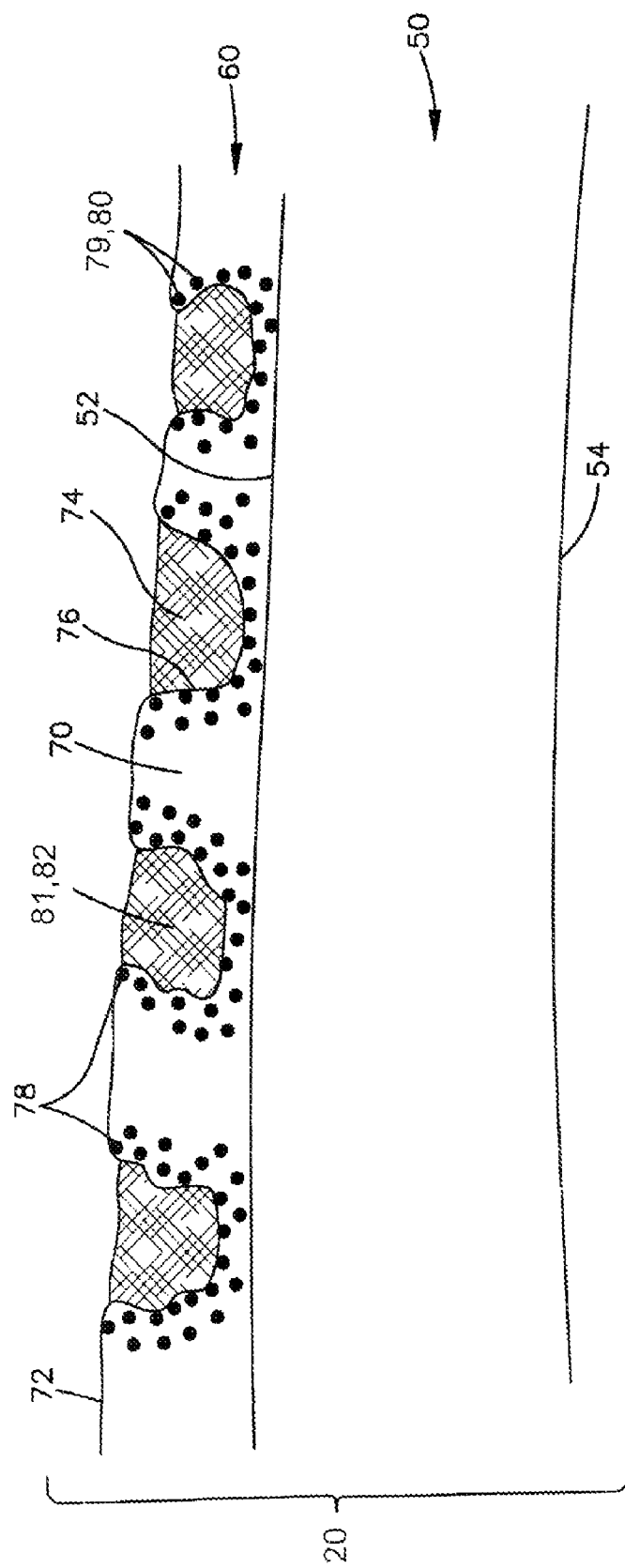
FIG. 5 shows a cross-sectional view of another embodiment of a first coating composition having cavities and pores disposed on a portion of a stent, wherein the pores and cavities contain a second coating composition.

FIG. 5 shows a cross-sectional view of a coating of the present invention disposed on a surface of a stent strut. As shown in FIG. 5, stent strut 50 has an abluminal surface 52 and a luminal surface 54. In this embodiment, coating 60 is disposed on the abluminal surface 52 of stent strut 50. Coating 60 comprises a first coating composition 70 comprising a metal, a metal oxide, ceramic oxide or an inert carbon, wherein the first coating composition 70 has an exposed surface 72. The first coating composition 70 also has a plurality of cavities 74 at least some of which are in fluid communication with the exposed surface 72. The cavities 74 have a cavity surface 76. Additionally, the first coating composition includes a plurality of pores 78, some of which are in fluid communication with a cavity surface 76. As shown in this embodiment, disposed within some of the pores 78 is a second coating composition 79 comprising a first therapeutic agent 80 and disposed within some of the cavities 76 is a third coating composition 81 comprising a second therapeutic agent 82. In other embodiments, the third coating composition can comprise at least one therapeutic agent, a polymer, or alternatively a therapeutic agent and a polymer. In FIG. 5, the third coating composition comprises a second therapeutic agent 82, wherein the first therapeutic agent and the second therapeutic agent are different.

Though, in FIGS. 2 through FIG. 5, the coating is disposed on the abluminal surface, which is the portion of the surface of the stent that faces a lumen wall, the coatings of the present invention can be applied to any surface of a medical device. In alternative embodiments, the coating can be disposed on a portion of a surface of a medical device that does not contact a lumen wall. Such embodiments can be useful when, in addition to administering a therapeutic agent to a lumen wall, it is also beneficial to introduce a therapeutic agent into the blood stream. For example, an intravascular stent having an abluminal and luminal surface can have the coating of the present invention disposed on both the abluminal and luminal surfaces. A coating on the abluminal surface can administer a therapeutic agent to a lumen wall and a coating on the luminal surface can introduce a therapeutic agent into the blood stream.

When a coating is disposed on both the abluminal and luminal surfaces of a stent, the coating disposed on the abluminal surface can be the same as or different from the coating disposed on the luminal surface of the stent. Also, the therapeutic agent disposed in the cavities of the coating on the abluminal and luminal sides can be the same or different.

Though the coatings of the present invention can provide controlled release of a therapeutic agent without the need for a polymer matrix, as shown in the coatings in FIGS. 1-5, in certain embodiments a polymer may be included in the coating compositions of the present invention. In some embodiments, the second coating composition can include a polymer. For example, a bioabsorbable polymer can be used to slow the release of the therapeutic agent disposed in the pores. A bioabsorbable polymer is capable of releasing the therapeutic agent as the polymer is being absorbed. A biostable polymer, which is not absorbed into the body, can also be used. For example, a biostable polymer can also be used to slow the release rate of the therapeutic agent by forcing the therapeutic agent to travel through the porous network to the coating surface.

Figure 6:
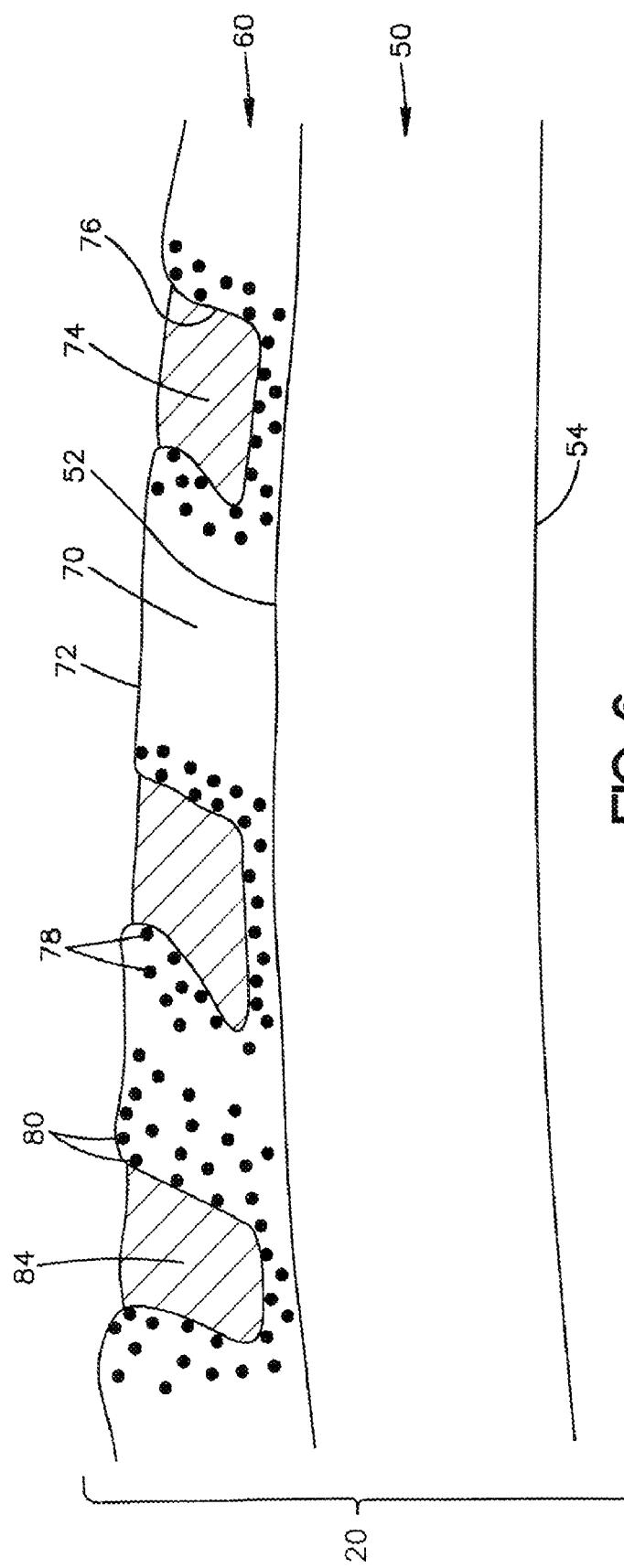
FIG. 6 shows a cross-sectional view of still another embodiment of a first coating composition having cavities and pores disposed on a portion of a stent, wherein the pores and cavities contain a second coating composition.

In some embodiments, as shown in FIG. 6, the coatings of the present invention can further include a third coating composition, disposed in the cavities, wherein the third coating composition includes a polymer. FIG. 6 shows a cross-sectional view of a coating of the present invention disposed on a surface of a stent strut. As shown in FIG. 6, stent strut 50 has an abluminal surface 52 and a luminal surface 54. In this embodiment, coating 60 is disposed on the abluminal surface 52 of stent strut 50. Coating 60 includes a first coating composition 70 having a metal, a metal oxide, ceramic oxide or inert carbon, wherein the first coating composition 70 has an exposed surface 72. The first coating composition 70 also has a plurality of cavities 74, at least some of which are in fluid communication with the exposed surface 72. The cavities 74 have a cavity surface 76. Additionally, the first coating composition includes a plurality of pores 78, some of which are in fluid communication with a cavity surface 76. As shown in this embodiment, disposed within some of the pores 78 is a second coating composition comprising a first therapeutic agent 80 and disposed within some of the cavities 76 is a third coating composition that includes a polymer 84. In other embodiments, the third coating composition can also include a therapeutic agent, wherein the therapeutic agent can be the same or a different therapeutic agent than that included in the first coating composition.

Figure 7:
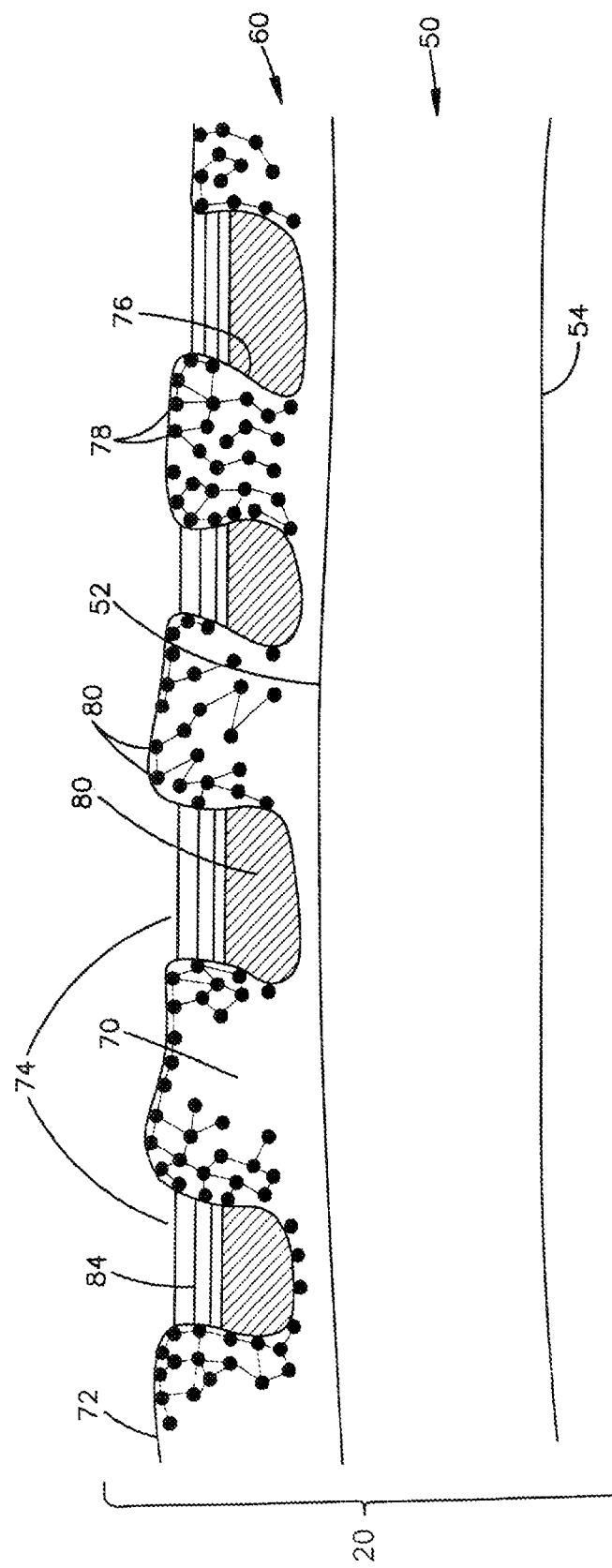
FIG. 7 shows a cross-sectional view of still another embodiment of a first coating composition having cavities and pores disposed on a portion of a stent, wherein the pores and cavities contain a second coating composition.

In some embodiments, as shown in FIG. 7, the coatings of the present invention can further include a third coating composition, disposed in a portion of the cavities, wherein the third coating composition includes a polymer. FIG. 7 shows a cross-sectional view of a coating of the present invention disposed on a surface of a stent strut. As shown in FIG. 7, stent strut 50 has an abluminal surface 52 and a luminal surface 54. In this embodiment, coating 60 is disposed on the abluminal surface 52 of stent strut 50. Coating 60 includes a first coating composition 70 having a metal, a metal oxide, ceramic oxide or inert carbon, wherein the first coating composition 70 has an exposed surface 72. The first coating composition 70 also has a plurality of cavities 74, at least some of which are in fluid communication with the exposed surface 72. The cavities 74 have a cavity surface 76. Additionally, the first coating composition includes a plurality of interconnected pores 78, some of which are in fluid communication with a cavity surface 76. As shown in this embodiment, disposed within some of the pores 78 and within a portion of some of the cavities 74 is a second coating composition that includes a first therapeutic agent 80. Also disposed within a portion of some of the cavities 76 is a third coating composition that includes a polymer 84. The therapeutic agent 80 disposed in a portion of at least some of the cavities 74 can serve as a reservoir while the third coating composition that includes a polymer 84 can serve as a cap, forcing the therapeutic agent 80 to travel through the porous network to the coating surface 72.

Figure 8:
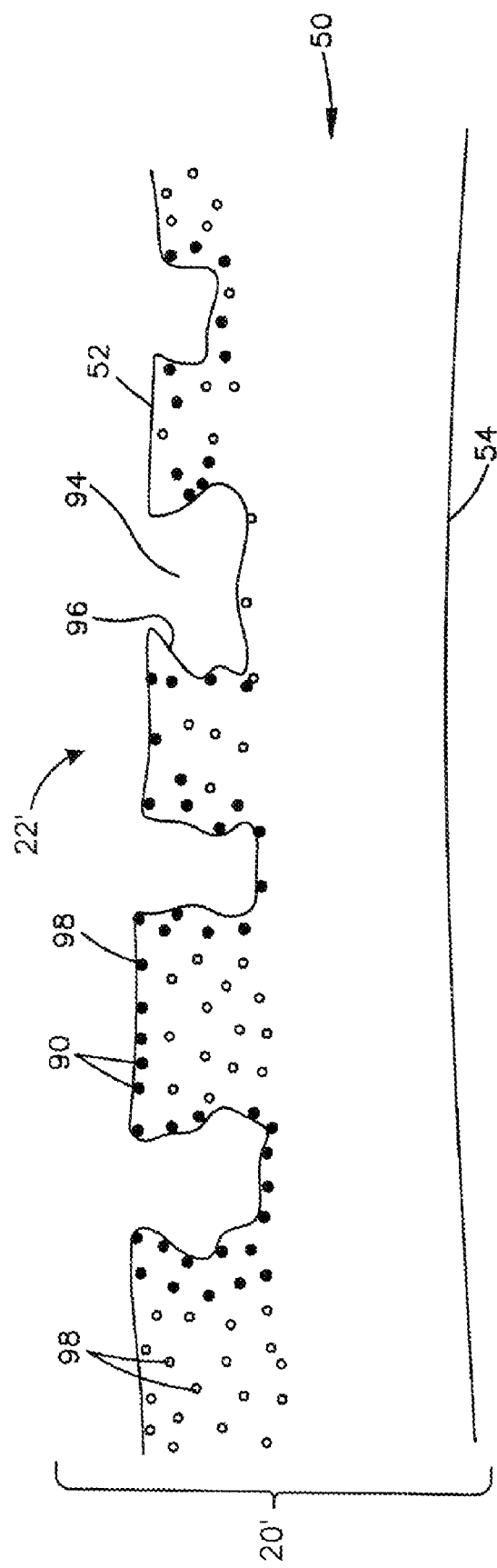
FIG. 8 shows a cross-sectional view of a portion of a stent strut having cavities and pores therein.

FIG. 8 shows a cross-sectional view of another embodiment where the cavities and pores are disposed in the surface 22' of a stent strut. As shown in FIG. 8, stent strut 50 has an abluminal surface 52 and a luminal surface 54. In this embodiment, stent strut 50 includes a metal, a metal oxide, ceramic oxide or inert carbon. The stent sidewall structure 20' of stent strut 50 also has a plurality of cavities 94 in fluid communication with the surface 52. The cavities 94 have a cavity surface 96. Additionally, the stent strut includes a plurality of pores 98, some of which are in fluid communication with a cavity surface 96. As shown in this embodiment, disposed within some of the pores 98 is a first composition comprising or including a therapeutic agent 100.

Additionally, embodiments of the present invention wherein the cavities and pores are disposed in the surface of the stent can also include coating compositions that include a therapeutic agent, a polymer, or both a therapeutic agent and a polymer like those described in FIGS. 2-7.

In accordance with the present invention, the cavities can have any shape. For example, the cavities can be shaped like cylinders or hemispheres. Cavities can also have non-circular cross-sectional shapes. Cavities can also be shaped like conduits, channels or void pathways. In certain embodiments the cavities can have cross-sectional shapes that are narrow at the top, near the exposed surface of the coating and then become broader near the surface of the medical device. Varying the shape can be used to maximize or optimize the surface area of the cavity surface which will determine the number of pores that can be in fluid communication with the cavity wall. Cavities having a cavity surface with a greater surface area will allow for a greater number of pores to be in fluid communication with the cavity surface. A greater number of pores will allow a greater amount of therapeutic agent to be loaded onto the medical device.

The cavities can be any size that will allow a sufficient number of pores to be formed in the cavity surface. For example, the cavities can be about 0.1 microns to about 20 microns in diameter or width. Preferably, the cavities can be about 1 micron to about 10 microns in diameter or width. Additionally, the cavities can be about 0.1 microns to about 20 microns deep. Preferably, the cavities can be about 1 micron to about 10 microns deep. In certain embodiments the cavities can be in fluid communication with the exposed surface of the medical device. Alternatively, in other embodiments the cavities may not be in fluid communication with the exposed surface of the medical device. Some or all of the cavities can be interconnected to other cavities.

Additionally, the pores can have any shape. For example, the pores can be shaped like cylinders, spheres or hemispheres. Pores can also have non-circular cross-sectional shapes. Pores can also be shaped like conduits, channels or void pathways. Varying the shape of the pores can be used to maximize or optimize that amount of therapeutic agent that can be loaded onto the surface of the medical device as well as the rate of release of the therapeutic agent. For example, pores having a larger width will allow the therapeutic agent to be released more quickly than pores with a smaller width. Also, the number of pores can be adjusted to control the release rate of the therapeutic agent. For example, the presence of more pores per unit area of the cavity surface or unit volume of the first coating material can increase the release rate of the therapeutic agent.

The pores are preferably smaller in size than the cavities and can be any size so long as at least some of the pores can be disposed on the cavity surface. For example, the pores can be about 0.001 microns to about 10 microns in diameter or width. Preferably, the pores can be about 0.01 microns to about 0.05 microns in diameter or width. Additionally, the pores can be about 0.001 microns to about 10 microns deep. Preferably, the pores can be about 0.01 microns to about 0.05 microns deep. In certain embodiments, some of the pores can be in fluid communication with the surface of the medical device and the cavity surface. Alternatively, in other embodiments the pores may not be in fluid communication with the surface of the medical device. Some or all of the pores can be interconnected to other pores.

A. Medical Devices

Suitable medical devices for the present invention include, but are not limited to, stents, surgical staples, cochlear implants, catheters, such as central venous catheters and arterial catheters, guidewires, cannulas, cardiac pacemaker leads or lead tips, cardiac defibrillator leads or lead tips, implantable vascular access ports, blood storage bags, blood tubing, vascular or other grafts, intra-aortic balloon pumps, heart valves, cardiovascular sutures, total artificial hearts and ventricular assist pumps, extra-corporeal devices such as blood oxygenators, blood filters, hemodialysis units, hemoperfusion units or plasmapheresis units.

Medical devices which are particularly suitable for the present invention include any stent for medical purposes, which are known to the skilled artisan. Suitable stents include, for example, vascular stents such as self-expanding stents and balloon expandable stents. Examples of self-expanding stents are illustrated in U.S. Pat. Nos. 4,655,771 and 4,954,126 issued to Wallsten and 5,061,275 issued to Wallsten et al. Examples of appropriate balloon-expandable stents are shown in U.S. Pat. No. 5,449,373 issued to Pinchasik et al. In preferred embodiments, the stent suitable for the present invention is an Express stent. More preferably, the Express stent is an Express™ stent or an Express2™ stent (Boston Scientific, Inc. Natick, Mass.).

The framework of the suitable stents may be formed through various methods as known in the art. The framework may be welded, molded, laser cut, electro-formed, or consist of filaments or fibers which are wound or braided together in order to form a continuous structure.

Medical devices that are suitable for the present invention may be fabricated from metallic, ceramic, polymeric or composite materials or a combination thereof. Preferably, the materials are biocompatible. Metallic material is more preferable. Suitable metallic materials include metals and alloys based on titanium (such as nitinol, nickel titanium alloys, thermo-memory alloy materials); stainless steel; tantalum, nickel-chrome; or certain cobalt alloys including cobalt-chromium-nickel alloys such as Elgiloy® and Phynox®; PERSS (Platinum EnRiched Stainless Steel) and Niobium. Metallic materials also include clad composite filaments, such as those disclosed in WO 94/16646.

Suitable ceramic materials include, but are not limited to, oxides, carbides, or nitrides of the transition elements such as titanium, hafnium, iridium, chromium, aluminum, and zirconium. Silicon based materials, such as silica, may also be used.

Suitable polymers for forming the medical devices may be biostable. Also, the polymer may be biodegradable. Suitable polymers include, but are not limited to, styrene isobutylene styrene, polyetheroxides, polyvinyl alcohol, polyglycolic acid, polylactic acid, polyamides, poly-2-hydroxy-butyrate, polycaprolactone, polylactic-co-glycolic acid, and Teflon.

Polymers may be used for forming the medical device in the present invention include without limitation isobutylene-based polymers, polystyrene-based polymers, polyacrylates, and polyacrylate derivatives, vinyl acetate-based polymers and its copolymers, polyurethane and its copolymers, silicone and its copolymers, ethylene vinyl-acetate, polyethylene terephtalate, thermoplastic elastomers, polyvinyl chloride, polyolefins, cellulosics, polyamides, polyesters, polysulfones, polytetrafluoroethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Other polymers that are useful as materials for medical devices include without limitation dacron polyester, poly (ethylene terephthalate), polycarbonate, polymethylmethacrylate, polypropylene, polyalkylene oxalates, polyvinylchloride, polyurethanes, polysiloxanes, nylons, poly (dimethyl siloxane), polycyanoacrylates, polyphosphazenes, poly(amino acids), ethylene glycol I dimethacrylate, poly (methyl methacrylate), poly(2-hydroxyethyl methacrylate), polytetrafluoroethylene poly(HEMA), polyhydroxyalkanoates, polytetrafluorethylene, polycarbonate, poly(glycolide-lactide) co-polymer, polylactic acid, poly(γ-caprolactone), poly(γ-hydroxybutyrate), polydioxanone, poly(γ-ethyl glutamate), polyiminocarbonates, poly(ortho ester), polyanhydrides, alginate, dextran, chitin, cotton, polyglycolic acid, polyurethane, or derivatized versions thereof, i.e., polymers which have been modified to include, for example, attachment sites or cross-linking groups, e.g., RGD, in which the polymers retain their structural integrity while allowing for attachment of cells and molecules, such as proteins, nucleic acids, and the like.

Medical devices may also be made with non-polymers. Examples of useful non-polymers include sterols such as cholesterol, stigmasterol, β-sitosterol, and estradiol; cholesteryl esters such as cholesteryl stearate; $C_{12}$-$C_{24}$ fatty acids such as lauric acid, myristic acid, palmitic acid, stearic acid, arachidic acid, behenic acid, and lignoceric acid; $C_{18}$-$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$-$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; sphingomyelins such as stearyl, palmitoyl, and tricosanyl sphingomyelins; ceramides such as stearyl and palmitoyl ceramides; glycosphingolipids; lanolin and lanolin alcohols; and combinations and mixtures thereof. Non-polymers may also include biomaterials such as stem sells, which can be seeded into the medical device prior to implantation. Preferred non-polymers include cholesterol, glyceryl monostearate, glycerol tristearate, stearic acid, stearic anhydride, glyceryl monooleate, glyceryl monolinoleate, and acetylated monoglycerides.

B. Coating Composition Materials

Metals, Metal Oxides, Ceramic Oxides and Carbons

When the first coating composition comprises a plurality of cavities and a plurality of pores, the first coating composition can include a metal, a metal oxide, ceramic oxide or inert carbon. The first coating composition can also be radiopaque and/or have MRI compatibility. Also, the first coating composition can have the same or some of the same materials that are used to make the medical device, specifically the medical device surface, on which the first coating composition is applied to.

Suitable metals include, but are not limited to, alkali metals, alkaline earth metals, transition metals, metal alloys and metalloids. Examples of metals include, but are not limited to, titanium, scandium, stainless steel, tantalum, nickel, Nitinol, chrome, cobalt, chromium, manganese, iron, platinum, iridium, niobium, vanadium, zirconium, tungsten, rhodium, ruthenium, gold, copper, zinc, yttrium, molybdenum, technetium, palladium, cadmium, hafnium, rhenium and combinations thereof. In certain embodiments, preferred metals include without limitation, gold tantalum, platinum, titanium, Nitinol or a combination thereof.

Suitable metal oxides and ceramic oxides include but are not limited to, platinum oxides, tantalum oxides, titanium oxides, zinc oxides, iron oxides, magnesium oxides, aluminum oxides, iridium oxides, niobium oxides, zirconium oxides, tungsten oxides, rhodium oxides, ruthenium oxides, hydroxyapatite, calcium phosphates, alumina, zirconia, zirconium, silicone oxides such as silica based glasses and silicon dioxide, or combinations thereof. In certain embodiments, preferred metal oxides or ceramic oxides include without limitation, iridium oxide, titanium oxide, titanium dioxide, iron oxide, hydroxyapatite, calcium phosphates, alumina, zirconia, zirconium, silica based glasses, or a combination thereof.

In other embodiments, the first coating composition can include inert carbon. Suitable forms of inert carbon can include with out limitation, pyrolitic carbon, porous vitreous carbon, diamond-like carbon, graphite and physical vapor deposition (PVD) carbon. Use of porous carbon can help prevent thrombosis and encourage endothelial cell growth.

In some embodiments, the metal, metal oxide, ceramic oxide or inert carbon can comprise at least 5%, at least 10%, at least 20%, at least 30%, at least 40%, at least 50%, at least 60%, at least 70%, at least 80%, at least 90%, at least 95%, at least 97%, at least 99% or more by weight of the coating composition. Preferably, the metal, metal oxide, ceramic oxide or inert carbon is about 10% to about 70% by weight of the coating composition.

The first coating composition may be of any thickness. In some embodiments, the first coating composition preferably has a thickness of about 1 to about 30 microns. In some instances, a relatively thicker film may be preferred to incorporate deeper cavities with more cavity surface.

Therapeutic Agents

The term "therapeutic agent" as used in the present invention encompasses therapeutic agents, genetic materials, and biological materials and can be used interchangeably with "biologically active material". In one embodiment, the therapeutic agent is an anti-restenotic agent. In other embodiments, the therapeutic agent inhibits smooth muscle cell proliferation, contraction, migration or hyperactivity. Non-limiting examples of suitable therapeutic agent include heparin, heparin derivatives, urokinase, dextrophenylalanine proline arginine chloromethylketone (PPack), enoxaprin, angiopeptin, hirudin, acetylsalicylic acid, tacrolimus, everolimus, zotarolimus, rapamycin (sirolimus), pimecrolimus, zotarolimus, amlodipine, doxazosin, glucocorticoids, betamethasone, dexamethasone, prednisolone, corticosterone, budesonide, sulfasalazine, rosiglitazone, mycophenolic acid, mesalamine, paclitaxel, 5-fluorouracil, cisplatin, vinblastine, vincristine, epothilones, methotrexate, azathioprine, adriamycin, mutamycin, endostatin, angiostatin, thymidine kinase inhibitors, cladribine, lidocaine, bupivacaine, ropivacaine, D-Phe-Pro-Arg chloromethyl ketone, platelet receptor antagonists, anti-thrombin antibodies, anti-platelet receptor antibodies, aspirin, dipyridamole, protamine, hirudin, prostaglandin inhibitors, platelet inhibitors, trapidil, liprostin, tick antiplatelet peptides, 5-azacytidine, vascular endothelial growth factors, growth factor receptors, transcriptional activators, translational promoters, antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin, cholesterol lowering agents, vasodilating agents, agents which interfere with endogenous vasoactive mechanisms, antioxidants, probucol, antibiotic agents, penicillin, cefoxitin, oxacillin, tobranycin, angiogenic substances, fibroblast growth factors, estrogen, estradiol (E2), estriol (E3), 17-beta estradiol, digoxin, beta blockers, captopril, enalopril, statins, steroids, vitamins, paclitaxel (as well as its derivatives, analogs or paclitaxel bound to proteins, e.g. Abraxane™) 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, 2'-O-ester with N-(dimethylaminoethyl) glutamide hydrochloride salt, nitroglycerin, nitrous oxides, nitric oxides, antibiotics, aspirins, digitalis, estrogen, estradiol and glycosides. In one embodiment, the therapeutic agent is a smooth muscle cell inhibitor or antibiotic. In a preferred embodiment, the therapeutic agent is taxol (e.g., Taxol®), or its analogs or derivatives. In another preferred embodiment, the therapeutic agent is paclitaxel, (i.e. paclitaxel, its analogs or derivatives). In yet another preferred embodiment, the therapeutic agent is an antibiotic such as erythromycin, amphotericin, rapamycin, adriamycin, etc.

The term "genetic materials" means DNA or RNA, including, without limitation, of DNA/RNA encoding a useful protein stated below, intended to be inserted into a human body including viral vectors and non-viral vectors.

The term "biological materials" include cells, yeasts, bacteria, proteins, peptides, cytokines and hormones. Examples for peptides and proteins include vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factors (CGF), platelet-derived growth factor (PDGF), hypoxia inducible factor-1 (HIF-1), stem cell derived factor (SDF), stem cell factor (SCF), endothelial cell growth supplement (ECGS), granulocyte macrophage colony stimulating factor (GM-CSF), growth differentiation factor (GDF), integrin modulating factor (IMF), calmodulin (CaM), thymidine kinase (TK), tumor necrosis factor (TNF), growth hormone (GH), bone morphogenic protein (BMP) (e.g., BMP-2, BMP-3, BMP-4, BMP-5, BMP-6 (Vgr-1), BMP-7 (PO-1), BMP-8, BMP-9, BMP-10, BMP-11, BMP-12, BMP-14, BMP-15, BMP-16, etc.), matrix metalloproteinase (MMP), tissue inhibitor of matrix metalloproteinase (TIMP), cytokines, interleukin (e.g., IL-1, IL-2, IL-3, IL-4, IL-5, IL-6, IL-7, IL-8, IL-9, IL-10, IL-11, IL-12, IL-15, etc.), lymphokines, interferon, integrin, collagen (all types), elastin, fibrillins, fibronectin, vitronectin, laminin, glycosaminoglycans, proteoglycans, transferrin, cytotactin, cell binding domains (e.g., RGD), and tenascin. Currently preferred BMP's are BMP-2, BMP-3, BMP-4, BMP-5, BMP-6, BMP-7. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can be formulated as needed to maintain cell function and viability. Cells include progenitor cells (e.g., endothelial progenitor cells), stem cells (e.g., mesenchymal, hematopoietic, neuronal), stromal cells, parenchymal cells, undifferentiated cells, fibroblasts, macrophage, and satellite cells.

Other non-genetic therapeutic agents include:
anti-thrombogenic agents such as heparin, heparin derivatives, urokinase, and PPack (dextrophenylalanine proline arginine chloromethylketone);
anti-proliferative agents such as enoxaprin, angiopeptin, or monoclonal antibodies capable of blocking smooth muscle cell proliferation, hirudin, acetylsalicylic acid, tacrolimus, everolimus, amlodipine and doxazosin;
anti-inflammatory agents such as glucocorticoids, betamethasone, dexamethasone, prednisolone, corticosterone, budesonide, estrogen, sulfasalazine, rosiglitazone, mycophenolic acid and mesalamine;
anti-neoplastic/anti-proliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, cladribine, taxol and its analogs or derivatives;
anesthetic agents such as lidocaine, bupivacaine, and ropivacaine;
anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory therapeutic agent), dipyridamole, protamine, hirudin, prostaglandin inhibitors, platelet inhibitors, antiplatelet agents such as trapidil or liprostin and tick antiplatelet peptides;
DNA demethylating therapeutic agents such as 5-azacytidine, which is also categorized as a RNA or DNA metabolite that inhibit cell growth and induce apoptosis in certain cancer cells;
vascular cell growth promoters such as growth factors, vascular endothelial growth factors (VEGF, all types including VEGF-2), growth factor receptors, transcriptional activators, and translational promoters;
vascular cell growth inhibitors such as anti-proliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;
cholesterol-lowering agents, vasodilating agents, and agents which interfere with endogenous vasoactive mechanisms;
anti-oxidants, such as probucol;
antibiotic agents, such as penicillin, cefoxitin, oxacillin, tobranycin, rapamycin (sirolimus);
angiogenic substances, such as acidic and basic fibroblast growth factors, estrogen including estradiol (E2), estriol (E3) and 17-beta estradiol; therapeutic agents for heart failure, such as digoxin, beta-blockers, angiotensin-converting enzyme (ACE) inhibitors including captopril and enalopril, statins and related compounds; and
macrolides such as sirolimus, everolimus, tacrolimus, pimecrolimus or zotarolimus.

Preferred biological materials include anti-proliferative therapeutic agents such as steroids, vitamins, and restenosis-inhibiting agents. Preferred restenosis-inhibiting agents include microtubule stabilizing agents such as Taxol®, paclitaxel (i.e., paclitaxel, paclitaxel analogs, or paclitaxel derivatives, and mixtures thereof). For example, derivatives suitable for use in the present invention include 2'-succinyl-taxol, 2'-succinyl-taxol triethanolamine, 2'-glutaryl-taxol, 2'-glutaryl-taxol triethanolamine salt, 2'-O-ester with N-(dimethylaminoethyl) glutamine, and 2'-O-ester with N-(dimethylaminoethyl) glutamide hydrochloride salt.

Other suitable therapeutic agents include tacrolimus; halofuginone; inhibitors of HSP90 heat shock proteins such as geldanamycin; microtubule stabilizing agents such as epothilone D; phosphodiesterase inhibitors such as cliostazole; Barkct inhibitors; phospholamban inhibitors; and Serca 2 gene/proteins.

Other preferred therapeutic agents include nitroglycerin, nitrous oxides, nitric oxides, aspirins, digitalis, estrogen derivatives such as estradiol and glycosides.

In one embodiment, the therapeutic agent is capable of altering the cellular metabolism or inhibiting a cell activity, such as protein synthesis, DNA synthesis, spindle fiber formation, cellular proliferation, cell migration, microtubule formation, microfilament formation, extracellular matrix synthesis, extracellular matrix secretion, or increase in cell volume. In another embodiment, the therapeutic agent is capable of inhibiting cell proliferation and/or migration.

In certain embodiments, the therapeutic agents for use in the medical devices of the present invention can be synthesized by methods well known to one skilled in the art. Alternatively, the therapeutic agents can be purchased from chemical and pharmaceutical companies.

In certain embodiments, when the cavities and pores are disposed in a coating composition, the therapeutic agent comprises at least 5%, at least 10%, at least 20%, at least 30%, at least 40%, at least 50%, at least 60%, at least 70%, at least 80%, at least 90%, at least 95%, at least 97%, at least 99% or more by weight of the coating composition. Preferably, the therapeutic agent is about 5% to about 35% by weight of the coating composition. More preferably, the therapeutic agent is about 8% to about 20% by weight of the second or third coating composition.

In other embodiments, when the cavities and pores are disposed in the stent, the therapeutic agent comprises at least 5%, at least 10%, at least 20%, at least 30%, at least 40%, at least 50%, at least 60%, at least 70%, at least 80%, at least 90%, at least 95%, at least 97%, at least 99% or more by weight of the composition. Preferably, the therapeutic agent is about 5% to about 35% by weight of the first or second composition. More preferably, the therapeutic agent is about 8% to about 20% percent by weight of the composition.

Polymers

Polymers useful in the present invention should be ones that are biocompatible, particularly during insertion or implantation of the device into the body and avoids irritation to body tissue. Examples of such polymers include, but not limited to, polyurethanes, polyisobutylene and its copolymers, silicones, and polyesters. Other suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxyethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers.

In certain embodiment hydrophobic polymers can be used. Examples of suitable hydrophobic polymers or monomers include, but not limited to, polyolefins, such as polyethylene, polypropylene, poly(1-butene), poly(2-butene), poly(1-pentene), poly(2-pentene), poly(3-methyl-1-pentene), poly(4-methyl-1-pentene), poly(isoprene), poly(4-methyl-1-pentene), ethylene-propylene copolymers, ethylene-propylene-hexadiene copolymers, ethylene-vinyl acetate copolymers, blends of two or more polyolefins and random and block copolymers prepared from two or more different unsaturated monomers; styrene polymers, such as poly(styrene), poly(2-methylstyrene), styrene-acrylonitrile copolymers having less than about 20 mole-percent acrylonitrile, and styrene-2,2,3, 3-tetrafluoropropyl methacrylate copolymers; halogenated hydrocarbon polymers, such as poly(chlorotrifluoroethylene), chlorotrifluoroethylene-tetrafluoroethylene copolymers, poly(hexafluoropropylene), poly(tetrafluoroethylene), tetrafluoroethylene, tetrafluoroethylene-ethylene copolymers, poly(trifluoroethylene), poly(vinyl fluoride), and poly (vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), poly(heptafluoroisopropoxypropylene), and poly(methacrylonitrile); acrylic polymers, such as poly (n-butyl acetate), poly(ethyl acrylate), poly(1-chlorodifluoromethyl)tetrafluoroethyl acrylate, poly di(chlorofluoromethyl)fluoromethyl acrylate, poly(1,1-dihydroheptafluorobutyl acrylate), poly(1,1-dihydropentafluoroisopropyl acrylate), poly(1,1-dihydropentadecafluorooctyl acrylate), poly (heptafluoroisopropyl acrylate), poly 5-(heptafluoroisopropoxy)pentyl acrylate, poly 11-(heptafluoroisopropoxy)undecyl acrylate, poly 2-(heptafluoropropoxy)ethyl acrylate, and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyesters, such a poly (ethylene terephthalate) and poly(butylene terephthalate); condensation type polymers such as and polyurethanes and siloxane-urethane copolymers; polyorganosiloxanes, i.e., polymers characterized by repeating siloxane groups, represented by Ra SiO 4-a/2, where R is a monovalent substituted or unsubstituted hydrocarbon radical and the value of a is 1 or 2; and naturally occurring hydrophobic polymers such as rubber.

In alternative embodiments, hydrophilic polymers can be used. Examples of suitable hydrophilic polymers or monomers include, but not limited to; (meth)acrylic acid, or alkaline metal or ammonium salts thereof; (meth)acrylamide; (meth)acrylonitrile; those polymers to which unsaturated dibasic, such as maleic acid and fumaric acid or half esters of these unsaturated dibasic acids, or alkaline metal or ammonium salts of these dibasic adds or half esters, is added; those polymers to which unsaturated sulfonic, such as 2-acrylamido-2-methylpropanesulfonic, 2-(meth)acryloylethanesulfonic acid, or alkaline metal or ammonium salts thereof, is added; and 2-hydroxyethyl (meth)acrylate and 2-hydroxypropyl (meth)acrylate.

Polyvinyl alcohol is also an example of hydrophilic polymer. Polyvinyl alcohol may contain a plurality of hydrophilic groups such as hydroxyl, amido, carboxyl, amino, ammonium or sulfonyl ($-SO_3$). Hydrophilic polymers also include, but are not limited to, starch, polysaccharides and related cellulosic polymers; polyalkylene glycols and oxides such as the polyethylene oxides; polymerized ethylenically unsaturated carboxylic acids such as acrylic, mathacrylic and maleic acids and partial esters derived from these acids and polyhydric alcohols such as the alkylene glycols; homopolymers and copolymers derived from acrylamide; and homopolymers and copolymers of vinylpyrrolidone.

Additional suitable polymers include, but are not limited to, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66 and polycaprolactone, alkyd resins, polycarbonates, polyoxymethylenes, polyimides, polyethers, polyether block amides, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (ethylene-propylene-diene) rubbers, fluoropolymers, fluorosilicones, polyethylene glycol, polysaccharides, phospholipids, and combinations of the foregoing.

Other polymers which can be used include ones that can be easily dissolved in water or organic solvents, cured or polymerized in the cavities of the first coating composition, have relatively low melting points and/or can be blended with therapeutic agents. Also bioabsorbable polymers may be used wherein the therapeutic agent is release as the polymer is absorbed into the body. An additional advantage of using a bioabsorbable material is that once the polymer is absorbed, the empty cavities can help prevent thromboses and encourage endothelial cell growth.

In certain embodiments preferred polymers include, but are not limited to, styrene-isobutylene-styrene, polylactic-co-glycolic acid (PLGA), polybutyl methacrylate (PBMA), polyvinylidene fluoride (PVDF), or a combination thereof.

C. Methods of Making the Coatings

In certain embodiments, the medical devices of the present invention are made by a method that includes the steps of disposing a first coating composition on at least a portion of a surface of a medical device wherein the first coating composition includes a metal, metal oxide, ceramic oxide or inert carbon; forming a plurality of cavities in the first coating composition, wherein the cavities have a cavity surface; forming a plurality of pores within the cavity surface; and disposing a second coating composition in the pores wherein the second coating composition includes a therapeutic agent.

In other embodiments, the medical device coatings of the present invention can be made by a method including the steps of disposing a first coating composition on at least a portion of a surface of a medical device wherein the first coating composition includes a metal, metal oxide, ceramic oxide or inert carbon; forming a plurality of pores within the first coating composition; thereafter forming a plurality of cavities in the first coating composition, wherein the cavities have a cavity surface and wherein at least some of the pores are in fluid communication with at least a cavity surface; and disposing a second coating composition in the pores wherein the second coating composition includes a therapeutic agent.

In the above methods, the first coating composition can be disposed on at least a portion of the surface of the medical device by any suitable method such as, but not limited to, dipping, spraying, painting, electroplating, evaporation, plasma vapor deposition, physical vapor deposition, cathodic-arc deposition, sputtering, ion implantation, electrostatically, electrochemically or a combination thereof.

The cavities and/or the pores in the first coating composition can be formed by any method known in the art as well. These methods include, but are not limited to, laser ablation, drilling, or chemical etching, microcontact printing, inkjet printing, screen printing, replica molding, microtransfer molding, micromolding in capillaries, solvent-assisted micromolding, proximal probe lithography, photolithography, scanning probe lithography, and embossing techniques.

Additionally, cavities and/or the pores in the first coating composition can be formed by removing a secondary material from the first coating composition. Techniques for removing a secondary material include, but are not limited to, dealloying or anodization processes. For example, a first coating composition containing a secondary material is disposed on a portion of a surface of a medical device. The first coating composition comprises a metal, metal oxide, ceramic oxide or inert carbon. The secondary material can be any material so long as it can be removed from the first coating composition. For example, the secondary material can be more electrochemically active than other metals in the coating composition. Preferably, the secondary material is a metal. Suitable metals include, but are not limited to, silver, gold, tantalum, platinum, bismuth, iridium, zirconium, iodine, titanium, and barium. After the first coating composition with the secondary material is disposed on the surface of the medical device, a plurality of cavities and/or pores are formed in the first coating composition by removing the secondary material.

The secondary material can be removed from the first coating composition by a dealloying process such as selective dissolution of the secondary material. In this method, the first coating composition and the secondary material are exposed to an acid which removes the secondary metal. Thus, the first coating composition is preferably one that will not dissolve when exposed to the acid, while the secondary metal is one that will dissolve. Any suitable acid can be used to remove the second metal. One of ordinary skill in the art would recognize the appropriate concentration and reaction conditions to use to remove the second metal. For example, if the secondary material is silver, nitric acid may be used at a concentration of up to 35% and a temperature up to 120° F. Also, a nitric acid and sulfuric acid mixture (95%/5%) immersion process at 80° F. may be used. The reaction conditions may be varied to vary the geometry, distribution, and depth of the coating layer.

Alternatively, the secondary material can be removed anodically. For example, silver may be removed anodically using a dilute nitric acid bath comprising up to 15% nitric acid, wherein the anode is the plated stent, and the cathode is platinum. Voltages up to 10V DC can be applied across the electrodes. The bath chemistry, temperature, applied voltage, and process time may be varied to vary the geometry, distribution, and depth of the coating layer. In another example, a Technic Envirostrip Ag 10-20 amps per square foot may be used with a stainless steel cathode.

In another embodiment, the present invention includes a method of coating a medical device that includes the steps of masking a portion of a surface of a medical device, such as a stent, with a masking material; disposing a first coating composition on the surface of the medical device, wherein the first coating composition includes a metal, metal oxide, ceramic oxide or inert carbon; forming a plurality of pores in the first coating composition; removing the masking material, creating a plurality of cavities; and disposing a second coating composition in the pores wherein, the second coating composition comprises a therapeutic agent.

For example, before the first coating composition is disposed on a portion of the surface of the medical device, polymer droplets can be applied to a portion of a surface of a medical device to mask the portion of the surface which that will comprise the cavities. The polymer droplets can be applied by methods such as inkjet printing and lithography. Once the first coating composition is disposed on the surface of the medical device, the polymer is removed, forming a plurality of cavities.

In the embodiments where the first coating composition includes cavities and pores, a second coating composition can be disposed in the pores. The second coating composition can include a therapeutic agent. Alternatively, the second coating composition can further include a polymer. The second coating composition can be disposed in the pores or cavities of the first coating composition in any suitable way known in the art. Such methods include, but are not limited to, inkjet printing or vacuum impregnation. Additional methods include coating the medical device with the second coating composition and removing the excess. For example, the second coating composition can be applied to a portion of a surface of a medical device by such methods as dipping, spraying, painting, roll coating, or a combination thereof and then removing the excess.

To facilitate disposing the second coating composition within the pores, a solution or suspension can be formed by dissolving or suspending the therapeutic agent in an organic or aqueous solvent, which is then disposed in at least some of the pores and the solvent is removed.

The above methods can further include disposing the second coating composition within at least some of the cavities. Alternatively, in other embodiments of the methods of the present invention, the methods can further include disposing a third coating composition within the cavities. The third coating composition can include a second therapeutic agent, wherein the second therapeutic agent is the same or different therapeutic agent than the first therapeutic agent. Alternatively, the third therapeutic agent can include a polymer or a polymer and a second therapeutic agent.

In general, when the coating compositions of the present invention includes polymer or a therapeutic agent and a polymer, a monomer can be mixed together and disposed in the pores and/or cavities with an initiator. Once in the pores and/or cavities the monomer can be polymerized by such methods as exposure to UV radiation or heat. The degree of polymerization, monomer and initiator used will be determined by the desired rate of release of the therapeutic agent.

Also encompassed in the present invention are methods of making an implantable stent having a surface including a metal, a metal oxide, ceramic oxide or inert carbon, wherein the method includes the steps of forming a plurality of pores in the metal oxide, ceramic oxide or inert carbon surface; forming a plurality of cavities in the metal, metal oxide, ceramic oxide or inert carbon surface, wherein the cavities have a cavity surface and wherein at least some of the pores are in fluid communication with the cavity surface; and disposing a first composition having a first therapeutic agent within at least some of the pores.

Alternatively, in certain embodiments of the methods of the present invention include methods of making an implantable stent having a surface having a metal, a metal oxide, ceramic oxide or inert carbon, the method comprising forming a plurality of cavities in the metal, metal oxide, ceramic oxide or inert carbon surface, wherein the cavities have a cavity surface thereafter; forming a plurality of pores in the metal, metal oxide, ceramic oxide or inert carbon surface, wherein at least some of the pores are in fluid communication with the cavity surface; and disposing a first composition having a first therapeutic agent within at least some of the pores.

Cavities and pores can be formed in the metal, metal oxide, ceramic oxide or inert carbon surface of a stent by any methods known in the art. For example, the cavities and the pores can be formed by the methods used to form the cavities and pores in the first coating composition discussed above.

Once cavities and pores are formed in the metal, metal oxide, ceramic oxide or inert carbon surface of the stent, a first composition can be disposed in the pores. The first composition can include a therapeutic agent. Alternatively, the first composition can further include a polymer. The first composition can be disposed in the pores of the surface of the stent in any suitable way known in the art. Such methods include, but are not limited to, inkjet printing or vacuum impregnation. Additional methods include coating the medical device with the first composition and removing the excess. For example, the first composition can be applied to a portion of a surface of a medical device by such methods as dipping, spraying, painting, roll coating, or a combination thereof and then removing the excess.

To facilitate disposing the first composition within the pores in the metal, metal oxide, ceramic oxide or inert carbon surface of the sent, a solution or suspension can be formed by dissolving or suspending a therapeutic agent in an organic or aqueous solvent which is then deposited in at least some of the pores and then the solvent is removed. The first composition can also be disposed within at least some of the cavities.

The medical devices and stents of the present invention may be used for any appropriate medical procedure. Delivery of the medical device can be accomplished using methods well known to those skilled in the art.

The following examples are for purposes of illustration and not for purposes of limitation.

EXAMPLE 1

A stainless steel stent is coated with a porous carbon coating having pores of nanometer size. The coating is applied using a PVD process. Cavities are ablated in the carbon coating using a UV laser, excimer or DPSS laser focused to a small size (<10 microns). The stent is then sprayed with a solution of paclitaxel in a toluene/TFH solvent system.

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

What is claimed is:

1. An implantable stent comprising:
  a stent sidewall structure comprising
  (a) a stent strut body having a surface defined by the stent strut body or by a surface coating on the stent strut body, the surface comprising a metal, a metal oxide, a ceramic oxide, or inert carbon;
  (b) the surface defining a plurality of cavities therein, at least some of the cavities being in fluid communication with the surface and at least one cavity being defined by a cavity surface having a plurality of pores therein;
  (c) a second coating composition comprising a first therapeutic agent, wherein the second coating composition is disposed within a portion of at least one of the cavities; and
  (d) a cap disposed in the at least one of the cavities and covering the second coating composition, wherein the cap is within the at least one of the cavities and wherein at least some of the pores in the cavity surface being not covered by the cap and being in fluid communication with the surface,
  thereby causing the first therapeutic agent to release through the pores to the surface and to not substantially release from the cavity directly to the surface.

2. The implantable stent of claim 1, wherein:
  the stent sidewall structure comprises the stent strut body and the surface coating on the stent strut, the surface is a surface of the surface coating, and the cavities are defined by the surface coating.

3. The stent of claim 1, wherein the sidewall structure comprises a plurality of struts and openings in the sidewall structure.

4. The stent of claim 2, wherein the surface is on an abluminal side of the stent strut body.

5. The stent of claim 3, wherein the surface coating conforms to a surface of the stent strut body so that the openings of the stent sidewall structure are preserved, and wherein the surface of the sidewall structure comprises an abluminal surface.

6. The stent of claim 1, wherein the stent is an intravascular balloon-expandable stent.

7. The stent of claim 1, wherein the stent is an intravascular self-expanding stent.

8. The stent of claim 2, wherein the surface coating composition is radiopaque.

9. The stent of claim 2, wherein the surface coating composition is free of any polymer.

10. The stent of claim 2, wherein the pores are distributed throughout the surface coating.

11. The stent of claim 10, wherein the pores are homogenously distributed throughout the surface coating.

12. The stent of claim 1, wherein the second coating composition is also disposed within at least one of the pores.

13. The stent of claim 1, wherein the second coating composition further comprises a polymer.

14. The stent of claim 13, wherein the polymer is biostable.

15. The stent of claim 13, wherein the polymer is bioabsorbable.

16. The stent of claim 13, wherein the polymer comprises styrene-isobutylene-styrene, polylactic-co-glycolic acid (PLGA), polybutyl methacrylate (PBMA), polyvinylidene fluoride (PVDF), or a combination thereof.

17. The stent of claim 1, wherein the metal oxide or ceramic oxide comprises iridium oxide, titanium oxide, titanium dioxide, iron oxide, hydroxyapatite, calcium phosphates, alumina, zirconia, zirconium, silica based glasses, or a combination thereof.

18. The stent of claim 1, wherein the metal comprises gold, tantalum, platinum, titanium, Nitinol or a combination thereof.

19. The stent of claim 1, wherein the surface coating is about 1 micron to about 30 microns thick.

20. The stent of claim 1, wherein the diameter of the pores is less than or equal to one micron.

21. The stent of claim 1, wherein the width of the cavities is greater than or equal to one micron.

22. The stent of claim 1, wherein the stent sidewall structure further comprises a third coating composition comprising a second therapeutic agent and, wherein the third coating composition is disposed within the pores.

23. The stent of claim 22, wherein the first therapeutic agent and second therapeutic agent are different.

24. The stent of claim 1, wherein the first therapeutic agent comprises an anti-thrombogenic agent, anti-angiogenesis agent, anti-proliferative agent, antibiotic, anti-restenosis agent, growth factor, immunosuppressant, or radiochemical.

25. The stent of claim 1, wherein the first therapeutic agent comprises an anti-restenosis agent.

26. The stent of claim 1, wherein the first therapeutic agent comprises paclitaxel.

27. The stent of claim 1, wherein the first therapeutic agent comprises sirolimus, tacrolimus, pimecrolimus, zotarolimus, or everolimus.

28. The stent of claim 1, wherein the cap comprises a polymer.

29. The stent of claim 1, wherein the stent sidewall structure further comprises a third coating composition comprising a second therapeutic agent, wherein the third coating composition is disposed in at least some of the pores.

30. The stent of claim 29, wherein the first therapeutic agent and second therapeutic agent are different.

31. The stent of claim 29, wherein the third coating composition further comprises a polymer.

32. The implantable stent of claim 1, wherein the stent sidewall structure comprises the stent strut body and the surface is a surface of the stent strut body.

33. The stent of claim 32, wherein the surface of the stent strut body is an abluminal surface.

34. The stent of claim 32, wherein the pores are distributed throughout the stent strut body.

35. The stent of claim 32, wherein the pores are homogenously distributed throughout the stent strut body.

36. A method of coating an implantable stent having a stent sidewall structure, the stent sidewall structure comprising a stent strut body having a surface defined by the stent strut body or by a surface coating on the stent strut body, the surface coating comprising a surface coating composition comprising a metal, a metal oxide or a ceramic oxide, or inert carbon, the stent sidewall structure defining a plurality of pores therein and, the method comprising:
 (a) creating a plurality of cavities in the surface, wherein the cavities have a cavity surface and wherein at least some of the pores are in fluid communication with a portion of the cavity surface;
 (b) disposing a second composition comprising a first therapeutic agent within a portion of at least one of the cavities; and
 (c) forming a cap in the at least one of the cavities to cover the second coating composition, wherein the cap is within the at least one of the cavities and wherein at least some of the pores in the cavity surface being not covered by the cap and being in fluid communication with the surface,
 thereby causing the first therapeutic agent to release through the pores to the surface and to not substantially release from the cavity directly to the surface.

37. The method of claim 36, wherein the stent sidewall structure comprises the stent strut body with the surface coating and the cavities are created in the surface coating composition.

38. The method of claim 36, further comprising disposing the second coating composition within at least some of the pores.

39. The method of claim 37, further comprising disposing a third coating composition within at least some of the pores, wherein the third coating composition comprises a second therapeutic agent.

40. The method of claim 36, wherein the cap comprises a polymer.

41. The method of claim 36, wherein the second coating composition further comprises a polymer.

42. The method of claim 36, wherein the cavities are created by laser ablation, drilling, chemical etching or a combination thereof.

43. The method of claim 36, further comprising disposing a third coating composition within at least some of the pores, wherein the third coating composition comprises a second therapeutic agent.

44. The method of claim 36, wherein the surface of the stent sidewall structure is a surface of the stent strut body, the pores are defined in the stent strut body, and the cavities are created in the stent strut body.

45. A method of coating an implantable stent having a stent sidewall structure, the stent sidewall structure comprising a strut and a surface coating comprising a surface coating composition comprising a metal, a metal oxide or a ceramic oxide, or inert carbon, the method comprising:
 (a) creating a plurality of cavities in the metal or ceramic oxide or inert carbon, wherein the cavities have a cavity surface;
 (b) creating a plurality of pores in the metal or ceramic oxide or inert carbon and wherein at least some of the pores are in fluid communication with a portion of the cavity surface; and
 (c) disposing a second composition comprising a first therapeutic agent within a portion of at least one of the cavities; and
 (d) forming a cap in the at least one of the cavities to cover the second coating composition, wherein the cap is within the at least one of the cavities and wherein at least some of the pores in the cavity surface being not covered by the cap and being in fluid communication with the surface, thereby causing the first therapeutic agent to release through the pores to the surface and to not substantially release from the cavity directly to the surface.

46. The method of claim 45, further comprising disposing the second composition within at least some of the pores.

47. The method of claim 45, further comprising disposing a third coating composition within at least some of the pores, wherein the third coating composition comprises a second therapeutic agent.

48. The method of claim 45, wherein the cap comprises a polymer.

49. The method of claim 45, wherein the cavities are formed by laser ablation, drilling, chemical etching or a combination thereof.

50. The implantable stent of claim 1, wherein the cap is within the at least one of the cavities and at least some of the pores in the cavity surface being not covered by the cap and being in fluid communication with the surface.

* * * * *

UNITED STATES PATENT AND TRADEMARK OFFICE
CERTIFICATE OF CORRECTION

| | |
|---|---|
| PATENT NO. | : 8,070,797 B2 |
| APPLICATION NO. | : 12/072666 |
| DATED | : December 6, 2011 |
| INVENTOR(S) | : Flanagan et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 163 days.

Signed and Sealed this
Twenty-fourth Day of April, 2012

David J. Kappos
*Director of the United States Patent and Trademark Office*